US011104887B2

(12) United States Patent
Rudolph et al.

(10) Patent No.: US 11,104,887 B2
(45) Date of Patent: Aug. 31, 2021

(54) ORNITHINE TRANSCARBAMYLASE CODING POLYRIBONUCLEOTIDES AND FORMULATIONS THEREOF

(71) Applicant: ethris GmbH, Planegg (DE)

(72) Inventors: Carsten Rudolph, Krailling (DE); Rebekka Kubisch-Dohmen, Munich (DE); Manish Kumar Aneja, Munich (DE); Johannes Geiger, Munich (DE); Marino Schuhmacher, Munich (DE)

(73) Assignee: ethris GmbH, Planegg (DE)

( * ) Notice: Subject to any disclaimer, the term of this patent is extended or adjusted under 35 U.S.C. 154(b) by 0 days.

(21) Appl. No.: 16/475,678

(22) PCT Filed: Dec. 15, 2017

(86) PCT No.: PCT/EP2017/082963
§ 371 (c)(1),
(2) Date: Jul. 2, 2019

(87) PCT Pub. No.: WO2018/127382
PCT Pub. Date: Jul. 12, 2018

(65) Prior Publication Data

US 2020/0308556 A1 Oct. 1, 2020

(30) Foreign Application Priority Data

Jan. 3, 2017 (EP) .................................... 17150143

(51) Int. Cl.
*C12N 9/10* (2006.01)
*C07K 14/47* (2006.01)

(52) U.S. Cl.
CPC ........... *C12N 9/1018* (2013.01); *C07K 14/47* (2013.01); *C12Y 201/03003* (2013.01)

(58) Field of Classification Search
CPC .................. C12N 9/1018; C07K 14/47; C12Y 201/03003
See application file for complete search history.

(56) References Cited

U.S. PATENT DOCUMENTS

| | | | | |
|---|---|---|---|---|
| 8,431,692 | B2 * | 4/2013 | Alpert | A61P 27/16 536/24.5 |
| 9,890,365 | B2 * | 2/2018 | Wang | C12Y 201/03003 |
| 10,017,826 | B2 * | 7/2018 | Von Der Mulbe | C12N 15/1003 |
| 2012/0195936 | A1 | 8/2012 | Rudolph et al. | |
| 2015/0291678 | A1 * | 10/2015 | Rudolph | A61K 38/1816 514/44 R |
| 2016/0130567 | A1 * | 5/2016 | Chivukula | C07K 14/4717 424/450 |
| 2018/0163213 | A1 * | 6/2018 | Aneja | C12N 9/22 |

FOREIGN PATENT DOCUMENTS

| | | | |
|---|---|---|---|
| WO | WO 2013/151666 | 10/2013 | |
| WO | WO 2015/138357 | 9/2015 | |
| WO | WO 2016/070166 | 5/2016 | |
| WO | WO 2017/167910 A1 * | 10/2017 | C12N 15/67 |

OTHER PUBLICATIONS

International Preliminary Report on Patentability issued in International Application No. PCT/EP2017/082963, dated Jul. 18, 2019.

* cited by examiner

*Primary Examiner* — Ganapathirama Raghu
(74) *Attorney, Agent, or Firm* — Morse, Barnes-Brown & Pendleton, P.C.; Lisa M. Warren, Esq.; Erin E. Bryan, Esq.

(57) ABSTRACT

In certain aspects, the disclosure relates to compositions comprising modified Ornithine transcarbamylase (OTC) polyribonucleotides and methods of use.

18 Claims, 15 Drawing Sheets

Specification includes a Sequence Listing.

| vehicle | 4 mg/kg |
| --- | --- |
| Q.DIHLGVNESLT.D | Q.DIHLGVNESLT.D |
| A.DAVLARVYKQS.D | T.DTARVLSSMA.D |
| A.DAVLARVYKQSDL.D | A.DAVLARVYKQS.D |
| | N.DPLEAAHGGNVLIT.D |
| | T.DYSPQLQKPKF.- |

underlined = human specific

```
NM_000531.5    ATGCTGTTTAATCTGAGGATCCTGTTAAACAATGCAGCTTTTAGAAATGGTCACAACTTC    60
hOTC-CO        ATGCTGTTCAACCTGCGGATCCTGCTGAACAACGCCGCCTTCCGGAACGGCCACAACTTC    60
               ******** ** *** ******** * ***** **  *  * ** ** ** *********

NM_000531.5    ATGGTTCGAAATTTTCGGTGTGGACAACCACTACAAAATAAAGTGCAGCTGAAGGGCCGT    120
hOTC-CO        ATGGTGCGCAACTTCAGATGCGGCCAGCCCCTGCAGAACAAGGTGCAGCTGAAAGGCCGG    120
               ***** ** ** ** * * ** ** ** ** ** *  ** ** ** *********  ****

NM_000531.5    GACCTTCTCACTCTAAAAAACTTTACCGGAGAAGAAATTAAATATATGCTATGGCTATCA    180
hOTC-CO        GACCTGCTGACCCTGAAGAACTTCACCGGCGAAGAGATCAAGTACATGCTGTGGCTGAGC    180
               ***** ** ** ** ** ***** ***** ***** ** ** ** ***** ***** :  .

NM_000531.5    GCAGATCTGAAATTTAGGATAAAACAGAAAGGAGAGTATTTGCCTTTATTGCAAGGGAAG    240
hOTC-CO        GCCGACCTGAAGTTCCGGATCAAGCAGAAGGGCGAGTACCTGCCCCTGCTGCAGGGAAAG    240
               ** ** ***** **  **** ** ***** ** *****  **** *  ****** ****

NM_000531.5    TCCTTAGGCATGATTTTTGAGAAAAGAAGTACTCGAACAAGATTGTCTACAGAAACAGGC    300
hOTC-CO        TCCCTGGGCATGATCTTCGAGAAGCGGAGCACCCGGACCCGGCTGTCTACCGAGACAGGA    300
               *** * ******** ** *****  ** ** ** *  **  ** ******* *******.

NM_000531.5    TTTGCACTTCTGGGAGGACATCCTTGTTTTCTTACCACACAAGATATTCATTTGGGTGTG    360
hOTC-CO        TTTGCCCTGCTGGGCGGCCACCCTTGCTTTCTGACCACCCAGGATATCCACCTGGGCGTG    360
               ***** ** ***** ** ** ***** ***** ***** ** ***** **  ***** ***

NM_000531.5    AATGAAAGTCTCACGGACACGGCCCGTGTATTGTCTAGCATGGCAGATGCAGTATTGGCT    420
hOTC-CO        AACGAGAGCCTGACCGACACAGCCAGAGTGCTGAGCAGCATGGCCGATGCCGTGCTGGCC    420
               ** ** ** ** ** ** ** ***  **  ** ** : **  ******** ***** **  ****

NM_000531.5    CGAGTGTATAAACAATCAGATTTGGACACCCTGGCTAAAGAAGCATCCATCCCAATTATC    480
hOTC-CO        AGAGTGTACAAGCAGAGCGACCTGGACACCCTGGCCAAAGAGGCCAGCATCCCCATCATC    480
               .******* ** **  :   ** *********** ***** **  : ****** ** ***

NM_000531.5    AATGGGCTGTCAGATTTGTACCATCCTATCCAGATCCTGGCTGATTACCTCACGCTCCAG    540
hOTC-CO        AACGGCCTGTCCGACCTGTACCACCCCATCCAGATCCTGGCCGACTACCTGACCCTGCAG    540
               ** ** ***** **  ***** ** ** ************ ** ***** ** ** ***

NM_000531.5    GAACACTATAGCTCTCTGAAAGGTCTTACCCTCAGCTGGATCGGGGATGGGAACAATATC    600
hOTC-CO        GAACACTACAGCAGCCTGAAGGGCCTGACACTGAGCTGGATCGGCGACGGCAACAACATC    600
               ******** ***:  ***** ** ** ** ** *********** ** ** ***** ***

NM_000531.5    CTGCACTCCATCATGATGAGCGCAGCGAAATTCGGAATGCACCTTCAGGCAGCTACTCCA    660
hOTC-CO        CTGCACTCTATCATGATGAGCGCCGCCAAGTTCGGCATGCATCTGCAGGCCGCCACCCCC    660
               ******** ************** ** ** ***** ***** ** ***** ** ** **.
```

FIG. 10

```
NM_000531.5      AAGGGTTATGAGCCGGATGCTAGTGTAACCAAGTTGGCAGAGCAGTATGCCAAAGAGAAT      720
hOTC-CO          AAGGGCTATGAGCCTGATGCCAGCGTGACCAAGCTGGCCGAGCAGTACGCCAAAGAGAAC      720
                 ***** ******** ***** ** **.****** ****.******** ***********

NM_000531.5      GGTACCAAGCTGTTGCTGACAAATGATCCATTGGAAGCAGCGCATGGAGGCAATGTATTA      780
hOTC-CO          GGCACCAAGCTGCTGCTGACCAACGACCCTCTGGAAGCCGCCCACGGCGGCAATGTGCTG      780
                 ** ********* *******.** ** **: *******.** ** **.********. *.

NM_000531.5      ATTACAGACACTTGGATAAGCATGGGACAAGAAGAGGAGAAGAAAAAGCGGCTCCAGGCT      840
hOTC-CO          ATCACCGATACCTGGATCAGCATGGGCCAGGAAGAGGAAAAGAAGAAGCGGCTGCAGGCC      840
                 ** **.** ** *****.********.**.********.*****.******** *****

NM_000531.5      TTCCAAGGTTACCAGGTTACAATGAAGACTGCTAAAGTTGCTGCCTCTGACTGGACATTT      900
hOTC-CO          TTCCAGGGCTACCAAGTGACCATGAAGACCGCCAAAGTGGCCGCCAGCGACTGGACCTTC      900
                 *****.** *****.** **.******** ** ***** ** ***:  ********.**

NM_000531.5      TTACACTGCTTGCCCAGAAAGCCAGAAGAAGTGGATGATGAAGTCTTTTATTCTCCTCGA      960
hOTC-CO          CTGCACTGCCTGCCCAGAAAGCCCGAAGAGGTGGACGACGAGGTGTTCTACAGCCCCCGG      960
                  *.****** *************.*****.***** ** **.** ** ** :  ** **.

NM_000531.5      TCACTAGTGTTCCCAGAGGCAGAAAACAGAAAGTGGACAATCATGGCTGTCATGGTGTCC      1020
hOTC-CO          TCCCTGGTGTTTCCCGAGGCCGAGAACCGGAAGTGGACCATCATGGCTGTGATGGTGTCT      1020
                 **.**.***** **.*****.**.***.*.********.*********** ********

NM_000531.5      CTGCTGACAGATTACTCACCTCAGCTCCAGAAGCCTAAATTTTGA     1065
hOTC-CO          CTGCTGACCGACTACTCCCCCCAGCTGCAGAAACCCAAGTTCTGA     1065
                 ********.** *****.** ***** *****.** **.** ***
```

Percent Identity Matrix - created by Clustal2.1

| | Pubmed | CO |
|---|---|---|
| NM_000531.5 | 100.00 | 76.90 |
| hOTC-CO | 76.90 | 100.00 |

FIG. 10 (cont.)

ORNITHINE TRANSCARBAMYLASE CODING POLYRIBONUCLEOTIDES AND FORMULATIONS THEREOF

RELATED APPLICATIONS

This application is a national stage filing under 35 U.S.C. 371 of International Application No.: PCT/EP2017/082963, filed Dec. 15, 2017, which claims priority to European Application No. 17150143.0 filed Jan. 3, 2017, the entire teachings of which are incorporated herein by reference. International Application No.: PCT/EP2017/082963 was published under PCT Article 21(2) in English.

SEQUENCE LISTING

The instant application contains a Sequence Listing which has been submitted electronically in ASCII format and is hereby incorporated by reference in its entirety. Said ASCII copy, created on Jan. 21, 2020, is named M1386481.txt and is 55,027 bytes in size.

BACKGROUND OF THE DISCLOSURE

Ornithine transcarbamylase (OTC) (also called ornithine carbamoyltransferase) is an enzyme that catalyzes the reaction between carbamoyl phosphate (CP) and ornithine (Orn) to form citrulline (Cit) and phosphate ($P_i$). In plants and microbes, OTC is involved in arginine biosynthesis, whereas in mammals it is located in the mitochondria and is part of the urea cycle. This cycle involves that ammonia is transported to the mitochondria where it is bound to $HCO_3$- and activated by phosphorylation into carbamoyl phosphate (CP) which is then transferred in the mitochondria by OTC to ornithine thereby producing citrulline. OTC is the central enzyme of the urea cycle. Citrulline can then be transported to the cytoplasm where it is further processed. Finally, urea is formed under the recovery of ornithine.

Individuals showing OTC deficiency show decreased citrulline and arginine concentrations and increased orotic acid levels (Jungermann, Histochem. Cell Biol. 103 (1995), 81-91) which is formed under conditions of accumulated carbamoyl phosphate. This biochemical phenotype (increased ammonia, low citrulline and increased orotic acid) is analyzed in plasma and urine samples and is characteristic for OTC deficiency, serving as a good biomarker for screening for therapeutic efficiency (Jungermann, loc. cit.).

In mammals, OTC deficiency is an X-chromosome-linked disease and the most common inborn error of urea synthesis in humans with a prevalence of about 1:40,000-1:80,000 births (Nagata et al., Am. J. Med. Gen. 40 (1991), 477-481). Current therapy for both neonatal onset and later onset OTC deficiency involves dietary nitrogen restriction combined with the stimulation of alternate pathways of waste nitrogen excretion using sodium phenylbutyrate (Batshaw et al., J. Pediatr. 108 (1986), 236-241). However, about half of hemizygous males with complete deficiencies die in infancy or early childhood and virtually all individuals who have had a sustained hyperammonemic encephalopathy event develop significant cognitive deficits (Brusilow and Horwich, In: Scriver, Beaudet, Sly and Valle, The Metabolic and Molecular Bases of Inherited Disease, McGraw-Hill, New York (1995), 1187-1232). The only other available treatment is liver transplantation.

According to an overview of a large number of individual OTC gene mutations and their clinical phenotype summarized by Tuchmann et al. (Hum. Mutat. 19(2) (2002), 93-107), it appears that OTC activity as low as 3% of wild-type activity would be sufficient to reverse the disease from a severe clinical phenotype to a mild phenotype. Accordingly, there is a need to provide methods and compositions to deliver OTC expression, as even a relatively low level of activity can be clinically and therapeutically meaningful.

SUMMARY OF THE DISCLOSURE

The present disclosure provides polyribonucleotides and polynucleotides, including modified polyribonucleotides and polynucleotides, in each case encoding ornithine transcarbamylase (OTC). Such polyribonucleotides and polynucleotides include DNA and RNA, such as mRNA, and may be provided in isolated and/or purified form. Moreover, polynucleotides of the disclosure may be provided in the context of a vector, plasmid, or longer polynucleotide, in each case, further comprising other sequences. Similarly, polyribonucleotides of the disclosure may be provided in the context of a longer nucleotide and may further comprise other sequences, such as 5'-UTR and/or 3'-UTR sequences. For example, in certain embodiments, a polyribonucleotide encoding OTC further includes a 5'-UTR derived from a human alpha-globin gene as described herein or a 5'-UTR and/or a 3'-UTR derived from a human CYBA gene as described herein.

Polyribonucleotides and polynucleotides of the disclosure have numerous uses, including in vitro or ex vivo uses in cells in culture, as well as in vivo uses in subjects.

In one aspect, the disclosure provides a polyribonucleotide comprising a sequence which encodes an ornithine transcarbamylase (OTC). Exemplary ornithine transcarbamylase (OTC) coding sequences are described herein, and can be readily selected for use in the claimed invention. In some embodiments, the polyribonucleotide, optionally modified, is codon optimized and encodes an ornithine transcarbamylase (OTC) described herein. In some embodiments, the polyribonucleotide is a modified polyribonucleotide comprising a combination of unmodified and modified ribonucleotides. For example, in some embodiments, 30-45% of the uridines in the polyribonucleotide are analogs of uridine and 5-10% of the cytidines in the polyribonucleotide are analogs of cytidine. Other percentages of modified uridines and cytidines are also contemplated, as described herein.

In another aspect, the disclosure provides a modified polyribonucleotide comprising a sequence which encodes an ornithine transcarbamylase (OTC) (as described above and herein), wherein the modified polyribonucleotide contains a combination of unmodified and modified ribonucleotides, wherein the modified polyribonucleotide is made using an input mixture of ribonucleotides, wherein 30-45% of uridines in said input mixture are analogs of uridine and 5-10% of cytidines in said input mixture are analogs of cytidine. Other percentages of modified uridines and cytidines are also contemplated, as described herein. Methods of producing such modified polyribonucleotides in vitro are also provided (e.g., via an in vitro transcription reaction in which the requisite percentage of a particular nucleotide analog is provided in the input mixture of nucleotides).

In some embodiments of any of the foregoing or other aspects and embodiments of the disclosure, the polyribonucleotide or modified polyribonucleotide comprises a primary sequence that encodes a polypeptide comprising an amino acid sequence which is at least 80% identical (e.g., at least 81, 82, 83, 84, 85, 86, 87, 88, 89, 90, 91, 92, 93, 94, 95, 96, 97, 98, 99 or 100% identical) to SEQ ID NO: 3 (amino acid sequence of the wildtype OTC) and which has the activity of an ornithine transcarbamylase (OTC). In some embodiments, the polyribonucleotide is a modified polyribonucleotide having a level of modification selected from any such level set forth herein.

The ornithine transcarbamylase (OTC) comprises a signal peptide which is translated and which is responsible for translocation to the mitochondria (Horwich et al., EMBO J. 4 (1985), 1129-1135). This signal peptide is represented by the first 32 amino acids as indicated in SEQ ID NO: 3. In certain embodiments, a polyribonucleotide of the disclosure encodes a wildtype OTC, such as set forth in SEQ ID NO: 3. In other embodiments, a polyribonucleotide of the disclosure encodes a wildtype OTC, in the absence of the signal sequence.

In some embodiments of any of the foregoing or other aspects and embodiments of the disclosure, the polyribonucleotide or modified polyribonucleotide comprises a primary sequence that is at least 95% identical (e.g., at least 95, 96, 97, 98, 99 or 100% identical) to SEQ ID NO: 1 (which represents the wildtype RNA sequence) (e.g., to the sequence set forth in SEQ ID NO: 1). In some embodiments, the polyribonucleotide is a modified polyribonucleotide having a level of modification selected from any such level set forth herein.

In some embodiments of any of the foregoing or other aspects and embodiments of the disclosure, the polyribonucleotide or modified polyribonucleotide comprises a primary sequence that is at least 75% identical (e.g., at least 75, 80, 85, 90, 95, 96, 97, 98, 99 or 100% identical) to SEQ ID NO: 4 (which represents a codon-optimized RNA sequence) (e.g., to the sequence set forth in SEQ ID NO: 4). In some embodiments, a polyribonucleotide or modified polyribonucleotide having any such level of sequence identity does not comprise the wildtype sequence (e.g., SEQ ID NO: 1). In some embodiments, the polyribonucleotide is a modified polyribonucleotide having a level of modification selected from any such level set forth herein.

In some embodiments of any of the foregoing or other aspects and embodiments of the disclosure, the polyribonucleotide or modified polyribonucleotide encodes an ornithine transcarbamylase (OTC) with altered activity relative to wildtype ornithine transcarbamylase (OTC), for example enhanced activity, in particular enhanced activity of catalyzing the reaction between carbamoyl phosphate (CP) and ornithine (Orn) to form citrulline (Cit) and phosphate ($P_i$). In other embodiments, the polyribonucleotide or modified polyribonucleotide encodes OTC with the same or substantially the same activity.

In some embodiments, the ornithine transcarbamylase (OTC) is human ornithine transcarbamylase (OTC).

In another aspect, the disclosure provides a polyribonucleotide or modified polyribonucleotide comprising a primary sequence at least 99% identical (e.g., 99% or 100% identical) to a sequence selected from the group consisting of SEQ ID NOs: 21-27 (in the presence or absence of a portion of promoter sequence). In certain embodiments, the disclosure provides a polyribonucleotide or modified polyribonucleotide comprising a primary sequence at least 99% identical (e.g., 99% or 100% identical) to a sequence selected from the group consisting of SEQ ID NOs: 21-27.

In certain embodiments the polyribonucleotide or modified polyribonucleotide comprises a primary sequence at least 99% identical (e.g., 99% or 100% identical) to the sequence of SEQ ID NO: 22 or SEQ ID NO: 25 which contain the wild-type coding region of human OTC and a codon-optimized version thereof, respectively, in combination with a UTR of the human alpha-globin gene.

In certain embodiments the polyribonucleotide or modified polyribonucleotide comprises a primary sequence at least 99% identical (e.g., 99% or 100% identical) to the sequence of SEQ ID NO: 23 or SEQ ID NO: 26 which contain the wild-type coding region of human OTC and a codon-optimized version thereof, respectively, in combination with a UTR of the human CYBA gene.

In certain embodiments the polyribonucleotide or modified polyribonucleotide comprises a primary sequence at least 99% identical (e.g., 99% or 100% identical) to the sequence of SEQ ID NO: 25 which contains a codon-optimized version of the coding region of human OTC in combination with a UTR of the human alpha-globin gene.

In certain embodiments the polyribonucleotide or modified polyribonucleotide comprises a primary sequence at least 99% identical (e.g., 99% or 100% identical) to the sequence of SEQ ID NO: 26 which contains a codon-optimized version the coding region of human OTC in combination with a UTR of the human CYBA gene.

In certain embodiments such primary sequence comprises or does not comprise sequences encoding a FLAG tag, a HA tag, or a similar epitope tag (e.g., optionally percent identity is determined without including such a tag). In some embodiment, the polyribonucleotide is a modified polyribonucleotide containing a combination of unmodified and modified ribonucleotides, wherein 5-50% of the uridines are analogs of uridine and 5-50% of the cytidines are analogs of cytidine.

In some embodiments of any of the foregoing or following aspects and embodiments, the polyribonucleotide encoding an ornithine transcarbamylase (OTC) is a modified polyribonucleotide containing a combination of unmodified and modified ribonucleotides, wherein 5-50% of the uridines are analogs of uridine and 5-50% of the cytidines are analogs of cytidine. In some embodiments, 25-45% of uridines are analogs of uridine and 5-20% of cytidines are analogs of cytidine. In some embodiments, 30-40% of uridines are analogs of uridine and 5-10% of cytidines are analogs of cytidine.

In another aspect, the disclosure provides a polyribonucleotide or a modified polyribonucleotide comprising a primary sequence at least 95% identical to SEQ ID NO: 1. In embodiments wherein the polyribonucleotide is a modified polyribonucleotide, the modified polyribonucleotide contains a combination of unmodified and modified ribonucleotides, wherein the modified polyribonucleotide is made using an input mixture of ribonucleotides, wherein 5-50% of uridines in the input mixture are analogs of uridine and 5-50% of cytidines in the input mixture are analogs of cytidine. In other embodiments, 25-45% of uridines in said mixture are analogs of uridine and 5-20% of cytidines in said mixture are analogs of cytidine. In other embodiments, 30-40% of uridines in said mixture are analogs of uridine and 5-10% of cytidines in said mixture are analogs of cytidine.

In some embodiments of any of the foregoing or following aspect and embodiments of the disclosure, the modified polyribonucleotide is codon-optimized for expression in mammalian cells.

Thus, in another aspect, the disclosure provides a polyribonucleotide or a modified polyribonucleotide comprising a primary sequence at least 95% identical to SEQ ID NO: 4. In embodiments wherein the polyribonucleotide is a modified polyribonucleotide, the modified polyribonucleotide contains a combination of unmodified and modified ribonucleotides, wherein the modified polyribonucleotide is made using an input mixture of ribonucleotides, wherein 5-50% of uridines in the input mixture are analogs of uridine and 5-50% of cytidines in the input mixture are analogs of cytidine. In other embodiments, 25-45% of uridines in said mixture are analogs of uridine and 5-20% of cytidines in said mixture are analogs of cytidine. In other embodiments, 30-40% of uridines in said mixture are analogs of uridine and 5-10% of cytidines in said mixture are analogs of cytidine.

In some embodiments a modified polyribonucleotide of the disclosure is sometimes also referred to as a SNIM® RNA (stabilized non-immunogenic mRNA) due to the fact that, in some embodiments, the modifications lead to a higher stability (expression) and lower immunogenicity of the polyribonucleotide molecules when administered in vivo.

In some embodiments of any of the foregoing or following aspect and embodiments of the disclosure, the polyribonucleotide or modified polyribonucleotide further comprises a 3' UTR, a 5' UTR, or a 3' UTR and a 5' UTR, and wherein the UTR(s) may optionally aid(s) in enhancing expression or increasing stability of the polyribonucleotide encoding an ornithine transcarbamylase (OTC) in cells.

In some embodiments of any of the foregoing or following aspect and embodiments of the disclosure, the 5' UTR comprises one or more sequences selected from the group consisting of SEQ ID NO: 11, SEQ ID NO: 13, SEQ ID NO: 15, SEQ ID NO: 17 and SEQ ID NO: 18, wherein the ribonucleotides of the 5' UTR are positioned upstream (5') of the ribonucleotides encoding the ornithine transcarbamylase (OTC), such as the ribonucleotides of SEQ ID NO: 1 or 4, and 3' from ribonucleotides corresponding to a portion of a promoter sequence, for example, directly 3' with less than 40 contiguous nucleotides intervening. In other embodiments, the 5' UTR is directly 3' from ribonucleotides corresponding to a portion of the promoter without any intervening nucleotides.

In some embodiments of any of the foregoing or following aspect and embodiments of the disclosure, the 5' UTR comprises one or more sequences selected from the group consisting of SEQ ID NO: 11, SEQ ID NO: 13, SEQ ID NO: 15, SEQ ID NO: 17 and SEQ ID NO: 18, wherein the ribonucleotides of the 5' UTR are positioned upstream (5') of the ribonucleotides encoding the ornithine transcarbamylase (OTC), such as the ribonucleotide of SEQ ID NO: 4, and 3' from ribonucleotides corresponding to a portion of a promoter sequence, for example, directly 3' with less than 40 contiguous nucleotides intervening. In other embodiments, the 5' UTR is directly 3' from ribonucleotides corresponding to a portion of the promoter without any intervening nucleotides.

In some embodiments of any of the foregoing or following aspect and embodiments of the disclosure, the 5' UTR comprises one or more sequences selected from the group consisting of SEQ ID NO: 13 and SEQ ID NO: 18, wherein the ribonucleotides of the 5' UTR are positioned upstream (5') of the ribonucleotides encoding the ornithine transcarbamylase (OTC), such as the ribonucleotides of SEQ ID NO: 1 or 4, and 3' from ribonucleotides corresponding to a portion of a promoter sequence, for example, directly 3' with less than 40 contiguous nucleotides intervening. In other embodiments, the 5' UTR is directly 3' from ribonucleotides corresponding to a portion of the promoter without any intervening nucleotides.

In some embodiments of any of the foregoing or following aspect and embodiments of the disclosure, the 5' UTR comprises one or more sequences selected from the group consisting of SEQ ID NO: 13 and SEQ ID NO: 18, wherein the ribonucleotides of the 5' UTR are positioned upstream (5') of the ribonucleotides encoding the ornithine transcarbamylase (OTC), such as the ribonucleotide of SEQ ID NO: 4, and 3' from ribonucleotides corresponding to a portion of a promoter sequence, for example, directly 3' with less than 40 contiguous nucleotides intervening. In other embodiments, the 5' UTR is directly 3' from ribonucleotides corresponding to a portion of the promoter without any intervening nucleotides.

In some embodiments of any of the foregoing or following aspect and embodiments of the disclosure, the 5' UTR and a portion of a promoter together comprise or consist essentially of SEQ ID NO: 10, SEQ ID NO: 12, SEQ ID NO: 14, SEQ ID NO: 20 or SEQ ID NO: 16.

In some embodiments of any of the foregoing or following aspect and embodiments of the disclosure, the 5' UTR and the portion of a promoter together comprise or consist essentially of SEQ ID NO: 12.

In some embodiments of any of the foregoing or following aspect and embodiments of the disclosure, the 5' UTR and the portion of a promoter together comprise or consist essentially of SEQ ID NO: 20.

In some embodiments of any of the foregoing or following aspect and embodiments of the disclosure, the 3' UTR comprises one or more copies of a 3' UTR sequence selected from the group consisting of SEQ ID NOs: 19 and SEQ ID NO: 30, wherein the ribonucleotides of the 3' UTR are positioned downstream (3') of the ribonucleotides encoding the ornithine transcarbamylase (OTC), such as the ribonucleotides of SEQ ID NO: 1 or 4, for example, directly downstream with less than 40 contiguous nucleotides intervening. In some embodiments, the ribonucleotides of the 3' UTR are positioned directly downstream (3') of the ribonucleotides encoding the ornithine transcarbamylase (OTC), such as the ribonucleotides of SEQ ID NO: 1 or 4, for example, with no nucleotides intervening.

In some embodiments of any of the foregoing or following aspect and embodiments of the disclosure, the 3' UTR comprises one copy of SEQ ID NO: 19, two copies of SEQ ID NO: 19, one copy of SEQ ID NO: 30, or two copies of SEQ ID NO: 30.

In some embodiments of any of the foregoing or following aspects and embodiments of the disclosure, the polyribonucleotide or modified polyribonucleotide further comprises a portion of a promoter sequence, wherein the ribonucleotides of the portion of a promoter sequence are positioned upstream (5') of the ribonucleotides of the 5' UTR and/or ornithine transcarbamylase (OTC) coding sequence(s). In some embodiments, the promoter sequence is selected from the group consisting of SEQ ID NOs: 6 to 9. In some embodiments, the sequence designated as promoter sequence may not include the final guanosine nucleotide, said guanosine nucleotide being the transcription start site and thus also part of the 5' UTR. In some embodiments, the sequence designated as promoter sequence may not include the single or several nucleotide(s) beginning with and following after the nucleotide that is the transcription start site, said single or several nucleotide(s) thus also being part of the 5' UTR. In some embodiments, the portion of the promoter sequence included in the 5' UTR corresponds to a region transcribed by a DNA-dependent RNA-polymerase.

In another aspect, the disclosure provides a polyribonucleotide comprising a primary polyribonucleotide sequence that is at least 99% or is 100% identical to a sequence selected from any of SEQ ID NO: 21-27, in the presence or absence of a polyribonucleotide encoding a FLAG tag, an HA tag or other epitope tag.

In some embodiments of any of the foregoing or following aspect and embodiments of the disclosure, the polyribonucleotide further comprises at least one 5' cap structure.

In some embodiments of any of the foregoing or following aspect and embodiments of the disclosure, the polyribonucleotide further comprises a polyA tail at the 3' end of the polyribonucleotide, and wherein the polyA tail comprises at least 100 bases.

In some embodiments of any of the foregoing or following aspect and embodiments of the disclosure, the polyribonucleotide is a modified polyribonucleotide, wherein the level of modification, the bases modified, and the potential analog are selected as described herein.

In another aspect, the disclosure provides a vector comprising a polynucleotide encoding a polyribonucleotide encoding an ornithine transcarbamylase (OTC), as described herein. Also provided is a host cell comprising the vector and a method of producing polyribonucleotides encoding an ornithine transcarbamylase (OTC).

In another aspect or in some embodiments of any of the foregoing or following, the disclosure provides a polyribonucleotide encoding a polypeptide comprising an amino acid sequence which is at least 80% identical (e.g., at least 81, 82, 83, 84, 85, 86, 87, 88, 89, 90, 91, 92, 93, 94, 95, 96, 97, 98, 99 or 100% identical) to SEQ ID NO: 3. In some embodiments, the polyribonucleotide is codon optimized. In some embodiments, the polyribonucleotide is a modified polyribonucleotide containing a combination of unmodified and modified ribonucleotides, wherein the modified polyribonucleotide is made using an input mixture of ribonucleotides, wherein 30-40% of uridines in said input mixture are analogs of uridine and 5-10% of cytidines in said input mixture are analogs of cytidine. Other percentages of modified ribonucleotides are similarly contemplated and disclosed herein.

In some embodiments of any of the foregoing or following aspects and embodiments of the disclosure, the modified polyribonucleotide is one or more beneficial properties as compared to an unmodified polyribonucleotide having the same primary sequence or compared to some other control or comparator. Exemplary beneficial properties may include increased translational efficiency, enhanced stability, and/or diminished immunogenicity.

In another aspect, the disclosure provides compositions comprising a polynucleotide or polyribonucleotide of the disclosure formulated with one or more pharmaceutically acceptable carriers and/or excipients.

In some embodiments of any of the foregoing or following aspects or embodiments, the modified polyribonucleotide is formulated in a nanoparticle or nanocapsule. In other embodiments, the modified polyribonucleotide is formulated in a cationic lipid, cationic polymer, or nanoemulsion.

In some embodiments of any of the foregoing or following aspects or embodiments, analogs are selected from amongst the analogs disclosed herein. In some embodiments, uridine analogs are selected from the group consisting of pseudouridine, 2-thiouridine, 5-iodouridine, and 5-methyluridine. In some embodiments, cytidine analogs are selected from the group consisting of 5-methylcytidine, 2'-amino-2'-deoxycytidine, 2'-fluoro-2'-deoxycytidine, and 5-iodocytidine.

In some embodiments of any of the foregoing or following aspects or embodiments, modified polyribonucleotides of the disclosure do not comprise 5-methylcytidine and/or pseudouridine and/or the analogs do not comprise 5-methylcytidine and/or pseudouridine.

In some embodiments of any of the foregoing or following aspects or embodiments, modified polyribonucleotide of the disclosure do not comprise analogs of adenosine and analogs of guanosine.

The disclosure contemplates all combinations of any of the foregoing aspects and embodiments, as well as combinations with any of the embodiments set forth in the detailed description and examples. The disclosure contemplates polynucleotides encoding an ornithine transcarbamylase (OTC) and, in some embodiments, modified polynucleotides encoding an ornithine transcarbamylase (OTC) that comprise or are derived from any one of the sequences corresponding to SEQ ID NOs: 1-27, as well as polyribonucleotide and modified polyribonucleotide sequences encoding all amino acid sequences listed herein.

The disclosure also contemplates polyribonucleotides which contain modified ribonucleotides as described herein and which comprise any of the sequences disclosed in the listing of sequences. Similarly, the disclosure also contemplates polynucleotides that can encode any of the ribonucleotides, as described herein, such as any of the sequences disclosed in the listing of sequences.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Modified polyribonucleotides were generated through in vitro transcription in the presence of 50% 5-iodouridine-5'-triphosphate and 30% 2'-fluoro-2'-deoxycytidine-5'-triphosphate of Constructs T7-hOTCcDNA (Table 9, SEQ ID NO: 31), T7-hOTCcDNA(CO) (Table 9, SEQ ID NO: 35), T7-hOTC (Table 9, SEQ ID NO: 32), T7-hOTC(CO) (Table 9, SEQ ID NO: 36), T7-5'ETH-hOTC-3'ETH (Table 9, SEQ ID NO: 34), T7-5'ETH-hOTC(CO)-3'ETH (Table 9, SEQ ID NO: 38), T7-5'hAg-hOTC (Table 9, SEQ ID NO: 33), and T7-5'hAg-hOTC(CO) (Table 9, SEQ ID NO: 37) respectively.

Figure 5A:
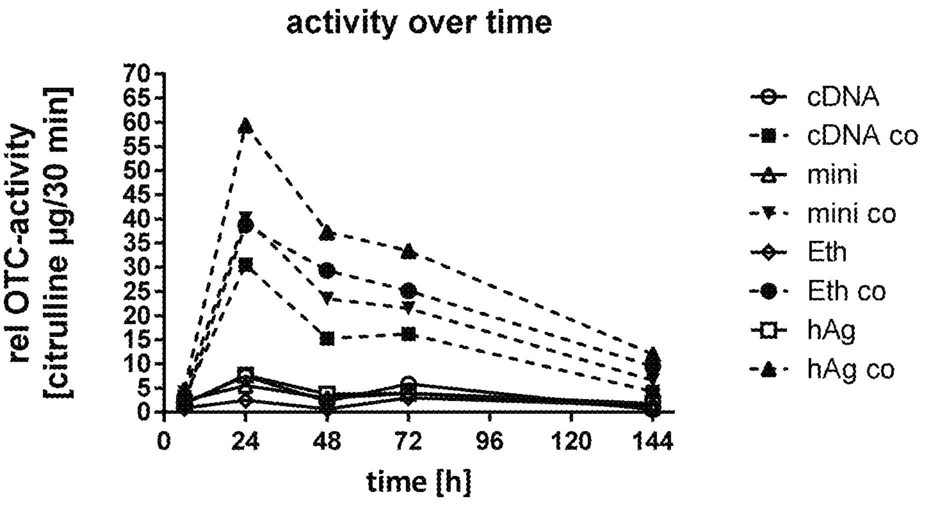

FIG. 5(A) shows OTC activity after transfection with OTC-SNIM® RNA in HepG2 cells. co=codon optimized; cDNA=cDNA; Minimal=mini, Ethris=Eth (=CYBA), α-Globin=hAg. Modified polyribonucleotides of the disclosure (e.g., OTC-SNIM®-RNA) were generated through in vitro transcription in the presence of 50% 5-iodouridine-5'-triphosphate and 30% 2'-fluoro-2'-deoxycytidine-5'-triphosphate of Constructs T7-hOTCcDNA (Table 9, SEQ ID NO: 31), T7-hOTCcDNA(CO) (Table 9, SEQ ID NO: 35), T7-hOTC (Table 9, SEQ ID NO: 32), T7-hOTC(CO) (Table 9, SEQ ID NO: 36), T7-5'ETH-hOTC-3'ETH (Table 9, SEQ ID NO: 34), T7-5'ETH-hOTC(CO)-3'ETH (Table 9, SEQ ID NO: 38), T7-5'hAg-hOTC (Table 9, SEQ ID NO: 33), and T7-5'hAg-hOTC(CO) (Table 9, SEQ ID NO: 37) respectively.

Figure 5B:
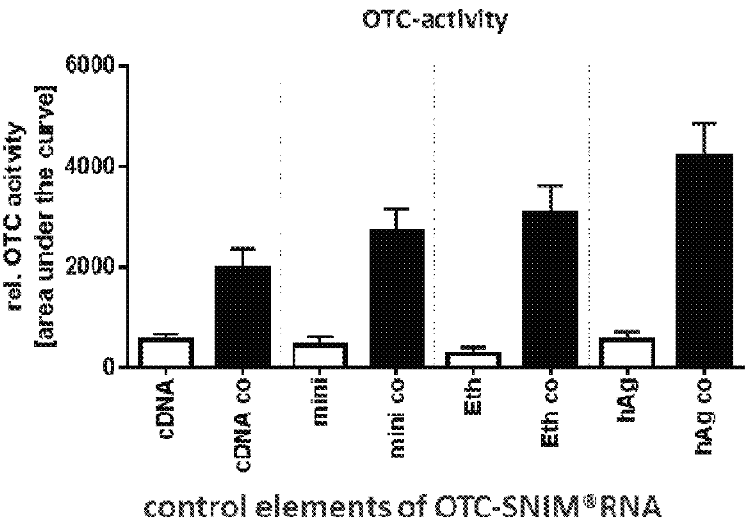

FIG. 5(B) shows OTC activity after transfection with OTC-SNIM® RNA in HepG2 cells co=codon optimized cDNA=cDNA; Minimal=mini, Ethris=Eth (=CYBA), α-Globin=hAg. Modified polyribonucleotides (e.g., SNIM®-RNAs) were generated through in vitro transcription in the presence of 50% 5-iodouridine-5'-triphosphate and 30% 2'-fluoro-2'-deoxycytidine-5'-triphosphate of Constructs T7-hOTCcDNA (Table 9, SEQ ID NO: 31), T7-hOTCcDNA(CO) (Table 9, SEQ ID NO: 35), T7-hOTC (Table 9, SEQ ID NO: 32), T7-hOTC(CO) (Table 9, SEQ ID NO: 36), T7-5'ETH-hOTC-3'ETH (Table 9, SEQ ID NO: 34), T7-5'ETH-hOTC(CO)-3'ETH (Table 9, SEQ ID NO: 38), T7-5'hAg-hOTC (Table 9, SEQ ID NO: 33), and T7-5'hAg-hOTC(CO) (Table 9, SEQ ID NO: 37) respectively.

Figure 5C:
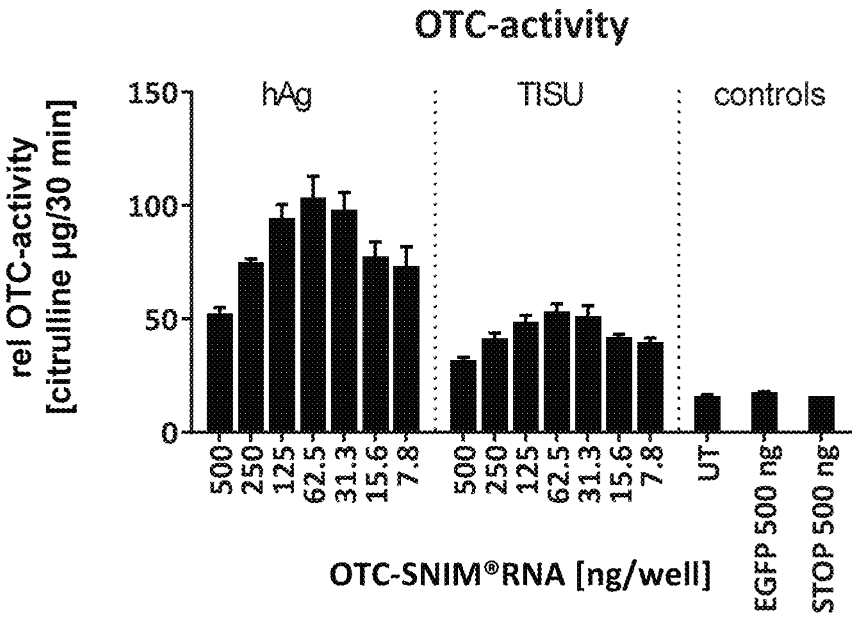

FIG. 5(C) shows OTC activity after exogenous expression of OTC protein by expressing modified polyribonucleotides encoding OTC (e.g., SNIM® RNA) in HepG2 cells. Modified polyribonucleotides (e.g., OTC SNIM® RNA) were generated by in vitro transcription in the presence of 35% 5-iodouridine-5'-triphosphate and 7.5% 5-iodocytidine-5'-triphosphate of Construct T7-5'hAg-hOTC(CO) (Table 9, SEQ ID NO: 37) or T7-TISU-hOTC(CO) (Table 9, SEQ ID NO: 39).

Figure 6:
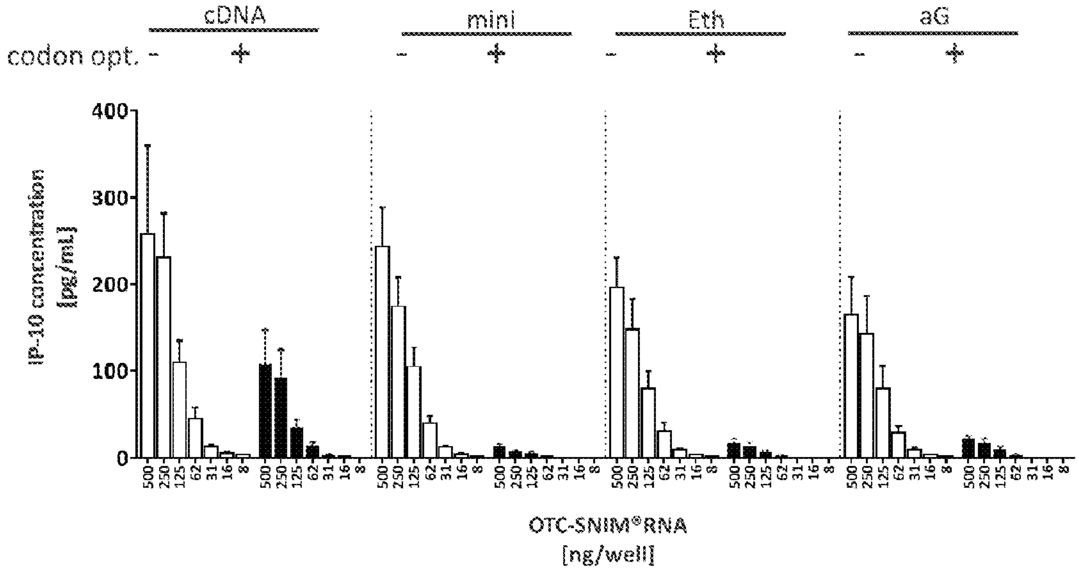

FIG. 6 shows that IP-10 induction is reduced in codon optimized OTC constructs. Modified polyribonucleotides encoding OTC (e.g., SNIM®-RNAs) were generated through in vitro transcription in the presence of 50% 5-iodouridine-5'-triphosphate and 30% 2'-fluoro-2'-deoxycytidine-5'-triphosphate of Constructs T7-hOTCcDNA (Table 9, SEQ ID NO: 31), T7-hOTCcDNA(CO) (Table 9, SEQ ID NO: 35), T7-hOTC (Table 9, SEQ ID NO: 32), T7-hOTC (CO) (Table 9, SEQ ID NO: 36), T7-5'ETH-hOTC-3'ETH (Table 9, SEQ ID NO: 34), T7-5'ETH-hOTC(CO)-3'ETH (Table 9, SEQ ID NO: 38), T7-5'hAg-hOTC (Table 9, SEQ ID NO: 33), and T7-5'hAg-hOTC(CO) (Table 9, SEQ ID NO: 37) respectively.

Figure 7A:
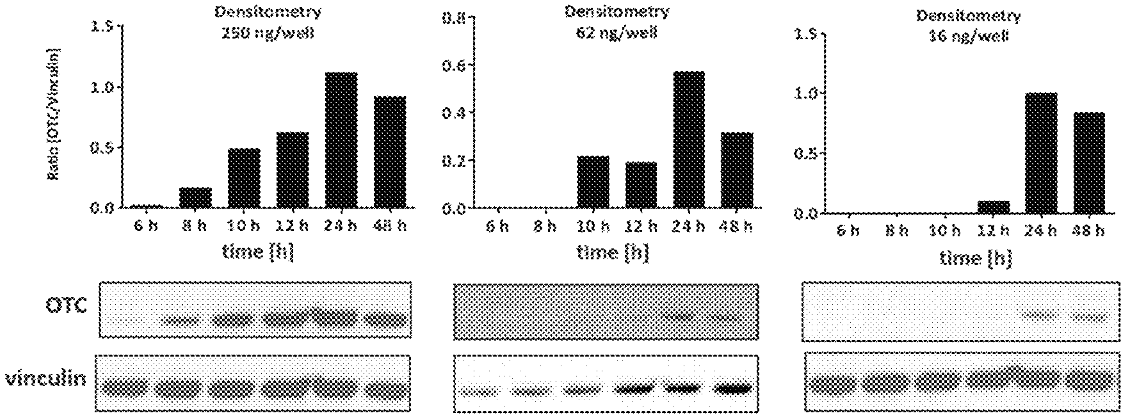

FIG. 7(A) shows the induction of OTC protein in HepG2 cells 8-12 h after transfection with SNIM® RNA generated by in vitro transcription in the presence of 35% 5-iodouridine-5'-triphosphate and 7.5% 5-iodocytidine-5'-triphosphate of construct T7-5'hAgOTC(CO) (Table 9, SEG ID NO: 37).

Figure 7B:
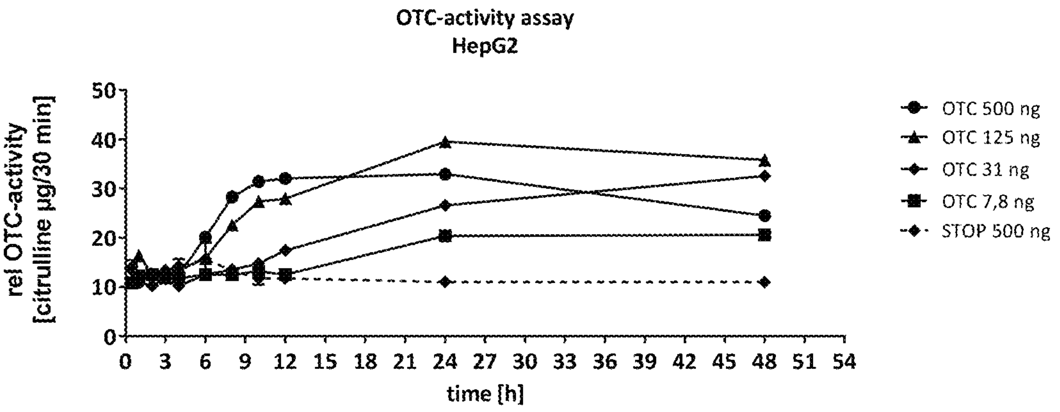

FIG. 7(B) shows OTC activity after transfection with OTC-SNIM® RNA generated by in vitro transcription in the presence of 35% 5-iodouridine-5'-triphosphate and 7.5% 5-iodocytidine-5'-triphosphate of construct T7-5'hAgOTC (CO) (Table9, SEG ID NO: 37) in HepG2 cells.

Figure 7C:
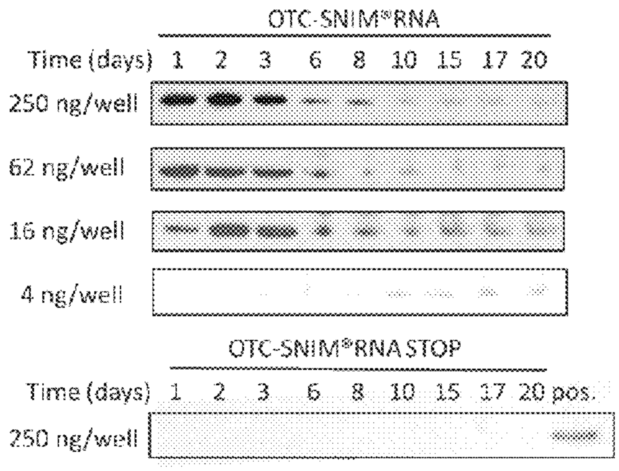

FIG. 7(C) shows that modified polyribonucleotides of the disclosure (e.g., SNIM® RNA) promotes/allows long term expression of OTC. SNIM® RNA was generated by in vitro transcription in the presence of 35% 5-iodouridine-5'-triphosphate and 7.5% 5-iodocytidine-5'-triphosphate of construct T7-5'hAgOTC(CO) (Table 9, SEG ID NO: 37). As a negative control a hOTC-STOP-RNA was used (SEQ ID NO: 44).

Figure 7D:
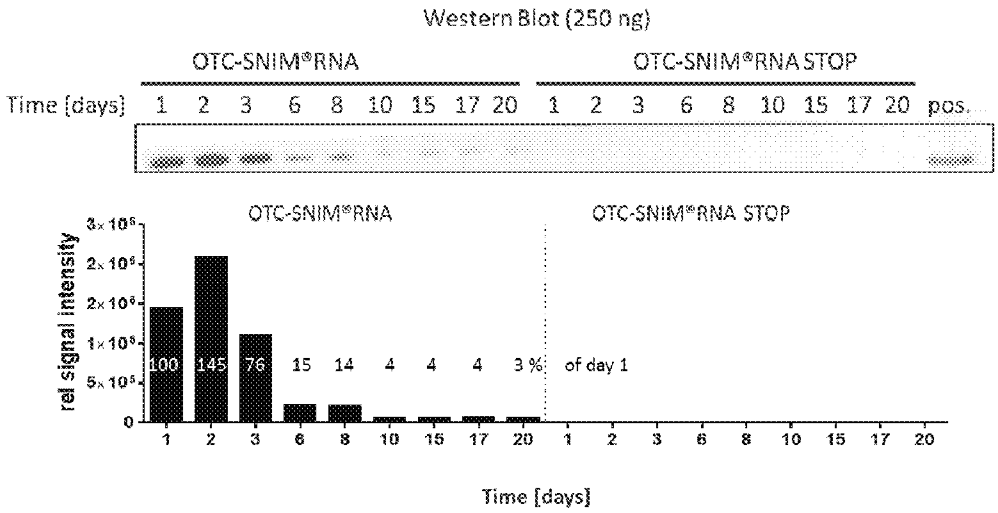

FIG. 7(D) shows OTC protein translation after transfection with OTC encoding modified polyribonucleotides of the disclosure (e.g., OTC-SNIM® RNA) in HepG2 cells. SNIM® RNA was generated by in vitro transcription in the presence 35% 5-iodouridine-5'-triphosphate and 7.5% 5-iodocytidine-5'-triphosphate of construct T7-5'hAgOTC(CO) (Table 9, SEG ID NO: 37). As a negative control a hOTC-STOP-RNA was used (SEQ ID NO: 44).

Figure 8:
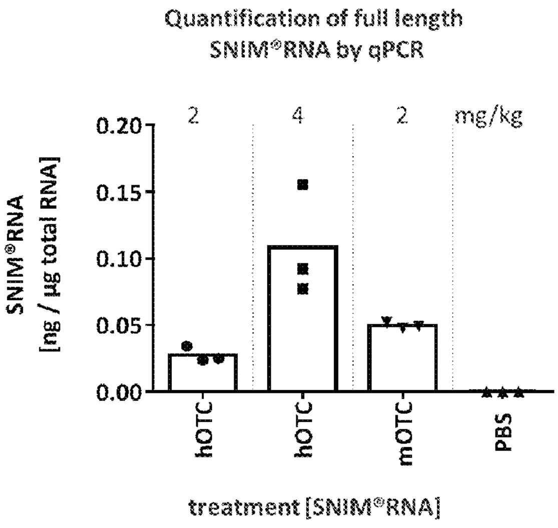

FIG. 8 shows the quantification of full length SNIM® RNA in vivo. SNIM® RNA was generated by in vitro transcription in the presence 50% 5-iodouridine-5'-triphosphate and 30% 2'-fluoro-2'-deoxycytidine-5'-triphosphate of construct T7-5'hAgOTC(CO) (Table 9, SEG ID NO: 37) for hOTC.

Figure 9A:
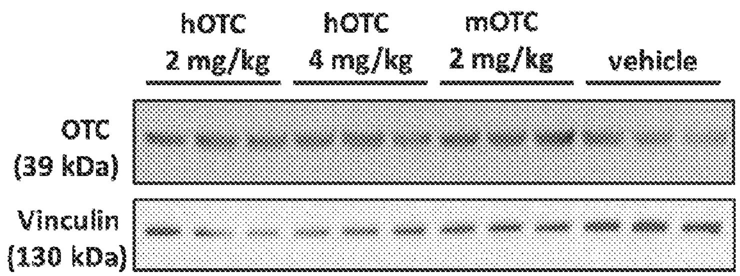

FIGS. 9(A) and (B) show an OTC Western Blot. SNIM® RNA was generated by in vitro transcription in the presence 50% 5-iodouridine-5'-triphosphate and 30% 2'-fluoro-2'-deoxycytidine-5'-triphosphate of construct T7-5'hAgOTC (CO) (Table 9, SEG ID NO: 37) for hOTC.

Figure 9B:
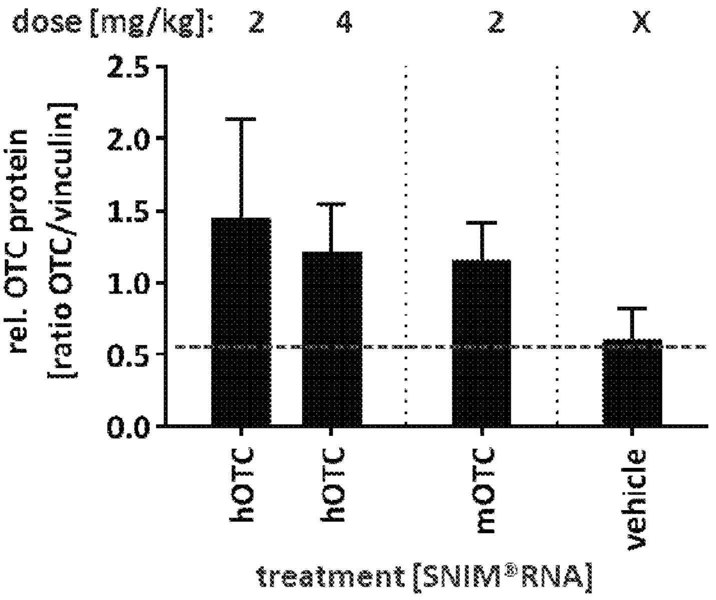
Figure 9C:
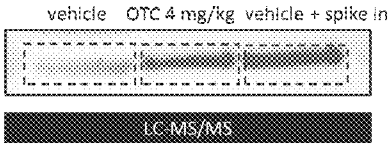

FIG. 9(C) shows an LC-MS/MS analysis of mouse liver samples (underlined=human specific).

FIG. 10 shows a CLUSTAL O(1.2.3) multiple sequence alignment between the wildtype human OTC coding region (NM_00531.5; SEQ ID NO: 2 and the codon optimized coding region (hOTC-CO); SEQ ID NO: 5). The two sequences are 76.90% identical to each other. The homology and percent identity matrix (as calculated by ClustalW) are provided below the alignment.

Figure 11:
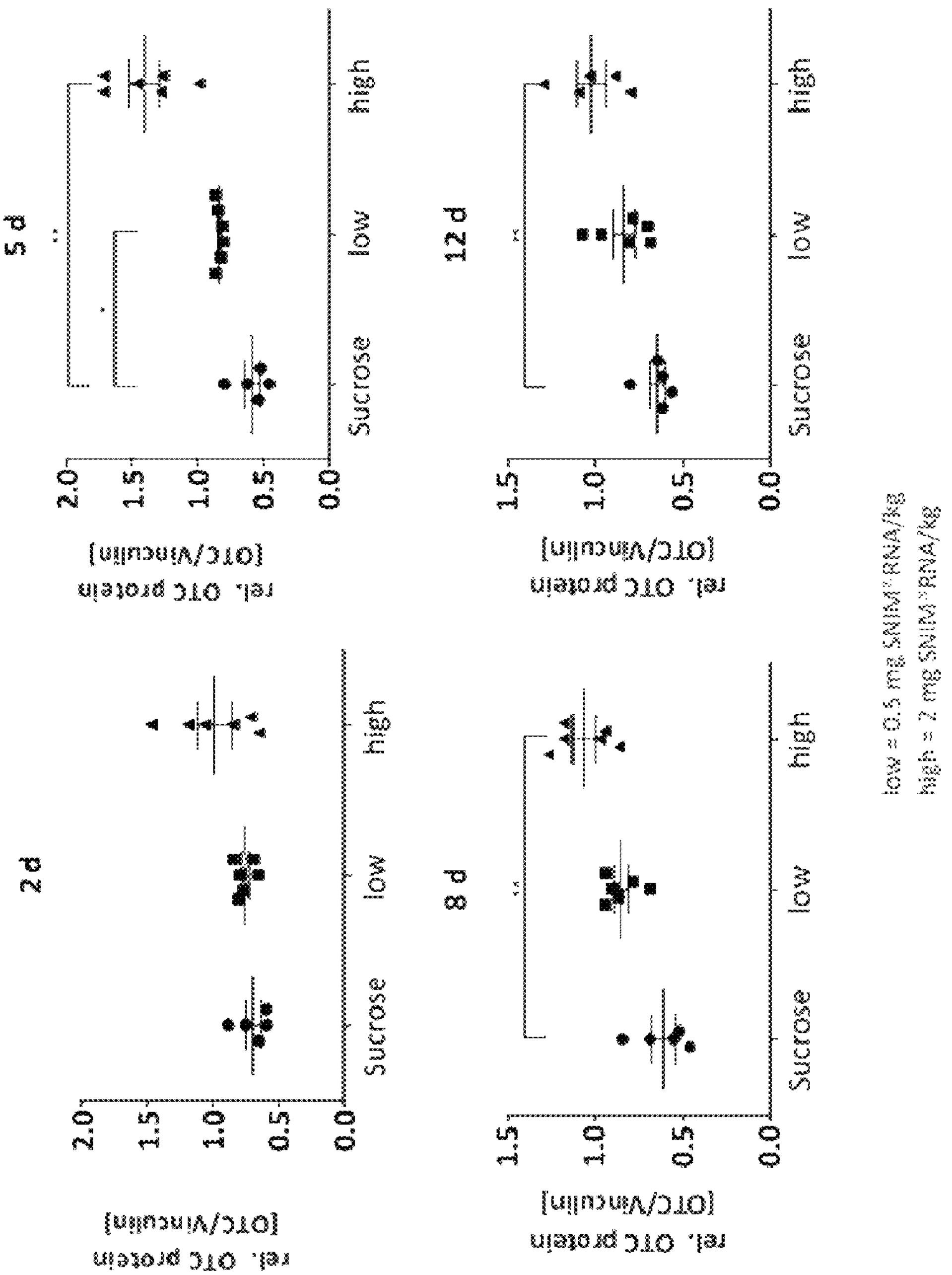

FIG. 11 shows the expression of human OTC protein in knockout mice ($OTC^{spf\ ash}$) after single application of human OTC SNIM® RNA as measured in a Western Blot analysis.

Figure 12:
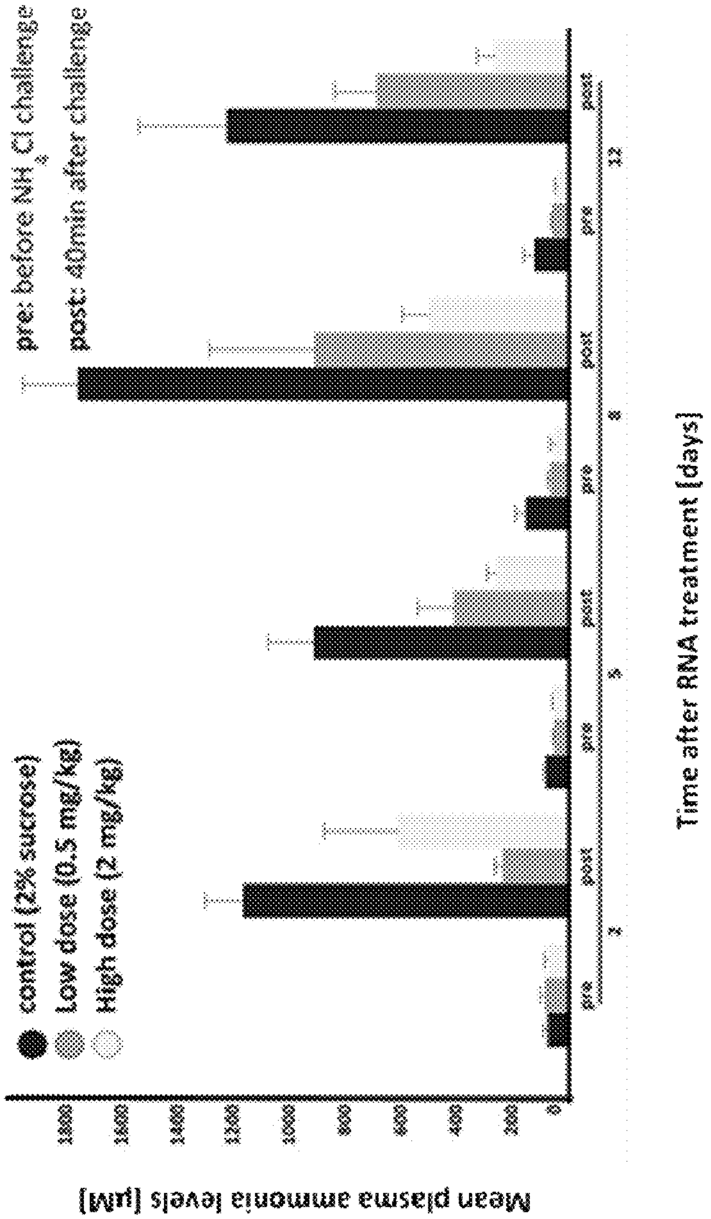

FIG. 12 shows the functionality of human OTC protein in knockout mice ($OTC^{spf\ ash}$) after single application of human OTC SNIM® RNA analysed by measuring blood ammonia levels at different time points post treatment.

Figure 13:
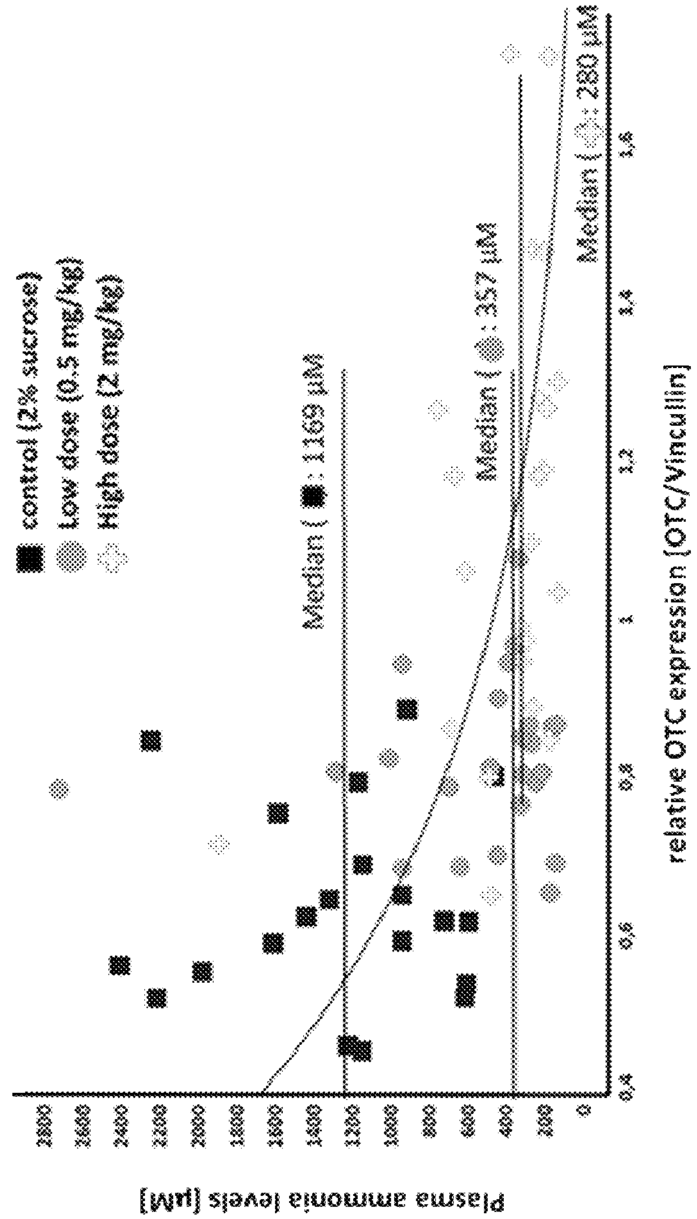

FIG. 13 shows a correlation analysis of the data shown in FIG. 11 and FIG. 12 using data points for all animals at all time points.

DETAILED DESCRIPTION OF THE DISCLOSURE

Overview

The present disclosure provides polyribonucleotides, polynucleotides and compositions that are useful for improving delivery of ornithine transcarbamylase (OTC) activity.

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

As used herein, the term "polynucleotide" is generally used to refer to a nucleic acid (e.g., DNA or RNA). When RNA, such as mRNA, is specifically being referred to, the term polyribonucleotide may be used. The terms polynucleotide, polyribonucleotide, nucleic acid, ribo nucleic acid, DNA, RNA, mRNA, and the like include such molecules that may be comprised of standard or unmodified residues; nonstandard or modified residues (e.g., analogs); and mixtures of standard and nonstandard (e.g., analogs) residues. In certain embodiments a polynucleotide or a polyribonucleotide is a modified polynucleotide or a polyribonucleotide.

For purposes of determining percentage identity of a first sequence relative to a second sequence, an analog (e.g., methylcytidine) matches the corresponding non-analog (e.g., cytidine), etc. In certain embodiments, the term "primary sequence" may be used to refer to a polynucleotide sequence without regard to whether or the level of modification, such that a primary sequence identical to CUCUCUA would include that sequence regardless of whether any or all of the recited nucleotides are modified (e.g., analogs of any one or more of C, U and A may be present and would be considered the same primary sequence).

Polynucleotides and polyribonucleotides of the disclosure refer, unless context indicates otherwise, to polynucleotides or polyribonucleotides encoding an ornithine transcarbamylase (OTC), preferably human ornithine transcarbamylase (OTC). Such polynucleotides and polyribonucleotides comprising an ornithine transcarbamylase (OTC) coding sequence may optionally comprise other nucleotide sequences, as described herein.

Polyribonucleotides

The present disclosure provides polyribonucleic acid molecules, preferably modified polyribonucleic acid molecules, which encode an ornithine transcarbamylase (OTC). The terms nucleic acid and polynucleotide are used interchangeably and include any compound and/or substance that comprises a polymer of nucleotides. The term nucleotide includes deoxynucleotides and ribonucleotides. The terms ribonucleic acid and polyribonucleotide are used interchangeably and, in certain embodiments, include any compound and/or substance that comprises a polymer of nucleotides wherein greater than 50% of the nucleotides are ribonucleotides. In certain embodiments, polyribonucletodies comprise a polymer of nucleotides wherein greater than 60%, 70%, 75%, 80%, 90%, greater than 95%, greater than 99% or 100% of the nucleotides are ribonucleotides. Polyribonucleotides wherein one or more nucleotides are modified nucleotides may be referred to as modified polyribonucleotides. However, the term polyribonucleotides may include modified polyribonucleotides.

The present disclosure also contemplates polyribonucleotides that may comprise one, several, or all of the features disclosed in the various embodiments herein. The present disclosure contemplates polyribonucleotides that may comprise one or more untranslated regions (UTRs) as disclosed herein. The present disclosure contemplates polyribonucleotides that encode an ornithine transcarbamylase (OTC). The present disclosure contemplates polyribonucleotides comprising ornithine transcarbamylase (OTC) coding sequences. The present disclosure contemplates polyribonucleotides comprising one or more analogs of the canonical nucleotides (i.e. analogs of cytidine, uridine, adenosine, and/or guanosine; modified nucleotides), naturally or non-naturally occurring; such polyribonucleotides contain a mixture of modified and unmodified nucleotides. In certain embodiments, the present disclosure contemplates polyribonucleotides wherein, for example, 30-50% or 30-45% of the uridines are analogs of uridine and 5-30% or 5-10% of the cytidines are analogs of cytidine. The present disclosure contemplates compositions comprising polyribonucleotides as described herein, and methods of formulating and using said compositions.

Polyribonucleotides and polynucleotides described herein that encode an ornithine transcarbamylase (OTC), alone or together with additional sequence, may be referred to as polynucleotides or polyribonucleotides of the disclosure. In certain embodiments, polyribonucleotides described herein may comprise ornithine transcarbamylase (OTC) coding sequences. In certain embodiments, polyribonucleotides described herein may comprise fragments of ornithine transcarbamylase (OTC) coding sequences. In certain embodiments, polyribonucleotides described herein may encode truncated variants of ornithine transcarbamylase (OTC) polypeptides.

The sequence of the polyribonucleotides can be derived from, for example, any suitable nucleic acid that comprises the genetic information of a gene of interest. Examples of nucleic acids include genomic DNA, RNA, or cDNA from any cell comprising the ornithine transcarbamylase (OTC) gene. The polynucleotides can be derived from nucleic acids carrying mutated genes and polymorphisms. Mutations and polymorphisms in the human ornithine transcarbamylase gene are described, e.g., in Tuchman et al. (Human Mutation 19 (2002), 93-107) and in Yamaguchi et al. (Human Mutation 27 (2006), 626-632). Caldovic et al. (J. Genet. Genomics 42 (2015), 181-194) provides an update of 417 disease-causing mutations in the OTC gene. Furthermore, this publication provides information about naturally occurring variations of the OTC gene in the general population and examination of the respective phenotype. A systematic computational approach has been performed to correlate different types of OTC mutations with the severity of the associated disease. A polyribonucleotide of the present disclosure comprises a sequence encoding an ornithine transcarbamylase (OTC) (e.g., a coding sequence). In certain embodiments, the sequence (e.g., DNA sequence and/or RNA sequence) is a codon optimized sequence, such as a codon optimized sequence to facilitate expression in a mammalian system. The polyribonucleotide may further comprise an untranslated sequence positioned upstream (5') of the ornithine transcarbamylase (OTC) encoding region's start codon, an untranslated sequence positioned downstream (3') of the ornithine transcarbamylase (OTC) encoding region's stop codon, or both an untranslated sequence positioned upstream (5') of the ornithine transcarbamylase (OTC) encoding region's start codon and an untranslated sequence positioned downstream (3') of the ornithine transcarbamylase (OTC) encoding region's stop codon. For each polyribonucleotide (RNA) sequence listed in the present disclosure, the corresponding polydeoxyribonucleotide (DNA) sequence is contemplated and vice versa. In a preferred embodiment, a polyribonucleotide of the present disclosure may be a modified polyribonucleotide.

Modified Ribonucleotides

In addition to the four classical ribonucleotides, namely, adenosine, guanosine, cytidine and uridine, there exist numerous analogs of each of these nucleobases. Sometimes throughout and in the literature, these analogs, or polyribonucleotides that include one or more of these analogs, are referred to as modified (e.g., modified nucleotides or modified ribonucleotides). Some analogs differ from the above canonical nucleobases, but yet can exist in nature. Other analogs are non-naturally occurring. Either type of analog is contemplated.

In certain embodiments, polyribonucleotides of the disclosure comprise nucleotide analogs (e.g., the polyribonucleotide comprises a modified polyribonucleotide). Exemplary nucleotide analogs are provided below (e.g., analogs of U; analogs of C; analogs of A; analogs of G). In addition, in certain embodiments, a polyribonucleotide or other nucleic acid of the disclosure may also comprise (in addition to or alternatively) modifications in the phosphodiester backbone or in the linkage between nucleobases. Exemplary nucleic acids that can form part or all of a polyribonucleotide of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a beta-d-ribo configuration, alpha-LNA having an alpha-1-ribo configuration (a diastereomer of LNA), 2'-amino-LNA having a 2'-amino functionalization, and 2'-amino-alpha-LNA having a 2'-amino functionalization) or hybrids thereof. In certain embodiments, a modification may be on one or more nucleoside(s) or the backbone of the polynucleotide molecule. In certain embodiments, a modification may be on both a nucleoside and a backbone linkage. In certain embodiments, a modification may be engineered into a polynucleotide in vitro. In certain embodiments, a modified nucleotide may also be synthesized post-transcriptionally by covalent modification of the natural nucleotides.

A polyribonucleotide of the disclosure can be a modified polyribonucleotide and, in certain embodiments, can comprise analogs of purines and/or analogs of pyrimidines. In certain embodiments, a modified polyribonucleotide of the disclosure comprises a pyrimidine analog, such as an analog of uridine and/or an analog of cytidine. In certain embodiments, a modified polyribonucleotide of the disclosure comprises an analog of uridine and an analog of cytidine. In certain embodiments, the modified polyribonucleotide does not comprise analogs of adenosine and/or analogs of guanosine. In certain embodiments, the polyribonucleotide comprises a single type of analog of uridine and a single type of analog of cytidine (e.g., one type of analog, not a single molecule of analog—the single analog may be present at any of several percentages described herein). In other embodiments, the polyribonucleotide comprises more than one type of analog of uridine and/or cytidine and, optionally and if present, one or more analogs of adenosine and/or guanosine (or none of either or both).

In some cases a modified uridine (e.g., analog of uridine) is selected from 2-thiouridine, 5'-methyluridine, pseudouridine, 5-iodouridine (I5U), 4-thiouridine (S4U), 5-bromouridine (Br5U), 2'-methyl-2'-deoxyuridine (U2'm), 2'-amino-2'-deoxyuridine (U2'$NH_2$), 2'-azido-2'-deoxyuridine (U2'$N_3$), and 2'-fluoro-2'-deoxyuridine (U2'F). In some cases, a modified cytidine (e.g., analog of cytidine) is selected from 5-methylcytidine, 3-methylcytidine, 2-thiocytidine, 2'-methyl-2'-deoxycytidine (C2'm), 2'-amino-2'-deoxycytidine (C2'NH2), 2'-fluoro-2'-deoxycytidine (C2'F), 5-iodocytidine (I5C), 5-bromocytidine (Br5C) and 2'-azido-2'-deoxycytidine (C2'N3). Note that when referring to analogs, the foregoing also refers to analogs in their 5' triphosphate form. In certain embodiments, the cytidine analog is 5-iodocytidine and the uridine analog is 5-iodouridine.

In some embodiments, the polyribonucleotide is a modified polyribonucleotide. In some cases, the modified polyribonucleotide is at least 25% more stable as compared to a non-modified (or unmodified) polyribonucleotide. In some cases, the modified polyribonucleotide can be at least 30% more stable, at least 35% more stable, at least 40% more stable, at least 45% more stable, at least 50% more stable, at least 55% more stable, at least 60% more stable, at least 65% more stable, at least 70% more stable, at least 75% more stable, at least 80% more stable, at least 85% more stable, at least 90% more stable, or at least 95% more stable as compared to a non-modified polyribonucleotide. In certain embodiments, stability is measured in vivo. In certain embodiments, stability is measured in vitro. In certain embodiments, stability is quantified by measuring the half-life of the polyribonucleotide.

A polyribonucleotide of the disclosure can have nucleotides that have been modified in the same form or else a mixture of different modified nucleotides. The modified nucleotides can have modifications that are naturally or not naturally occurring in messenger RNA. A mixture of various modified nucleotides can be used. For example one or more modified nucleotides within a polyribonucleotide can have natural modifications, while another part has modifications that are not naturally found in mRNA. Additionally, some modified nucleotides can have a base modification, while other modified nucleotides have a sugar modification. In the same way, it is possible that all modifications are base modifications or all modifications are sugar modifications or any suitable mixture thereof. In some cases, the stability of the modified polyribonucleotide can be selectively optimized by changing the nature of modified bases within the modified polyribonucleotide.

Non-limiting examples of analogs of U are shown in TABLE 1.

TABLE 1

| Name | Base modification (5'-position) | Sugar modification (2'-position) | Naturally in mRNA |
|---|---|---|---|
| 5-methyluridine (m5U) | $CH_3$ | | No |
| 5-iodouridine (I5U) | I | | No |
| 5-bromouridine (Br5U) | Br | | No |
| 2-thiouridine (S2U) | S (in 2 position) | | No |
| 4-thiouridine (S4U) | S (in 4 position) | | No |
| 2--methyl-2'-deoxyuridine (U2'm) | | $CH_3$ | Yes |
| 2'-amino-2'-deoxyuridine (U2'NH2) | | $NH_2$ | No |
| 2'-azido-2'-deoxyuridine (U2'N3) | | $N_3$ | No |
| 2'-fluoro-2'-deoxyuridine (U2'F) | | F | No |

Non-limiting examples of analogs of C are shown in TABLE 2.

TABLE 2

| Name | Base modification (5'-position) | Sugar modification (2'-position) | Naturally in mRNA |
|---|---|---|---|
| 5-methylcytidine (m5C) | $CH_3$ | | Yes |
| 5-iodocytidine (I5C) | I | | No |
| 5-bromocytidine (Br5C) | Br | | No |
| 2-thiocytidine (S2C) | S (in 2 position) | | No |
| 2'-methyl-2'-deoxycytidine (C2'm) | | $CH_3$ | Yes |
| 2'-amino-2'-deoxycytidine (C2'NH2) | | $NH_2$ | No |
| 2'-azido-2'-deoxycytidine (C2'N3) | | $N_3$ | No |
| 2'-fluoro-2'-deoxycytidine (C2'F) | | F | No |

Non-limiting examples of analogs of A are shown in TABLE 3.

TABLE 3

| Name | Base modification (5'-position) | Sugar modification (2'-position) | Naturally in mRNA |
|---|---|---|---|
| N6-methyladenosine (m6A) | $CH_3$ (in 6 position) | | Yes |
| N1-methyladenosine (m1A) | $CH_3$ (in 1 position) | | No |
| 2'-0-methyladenosine (A2'm) | | $CH_3$ | Yes |
| 2'-amino-2'-deoxyadenosine (A2'NH2) | | $NH_2$ | No |
| 2'-azido-2'-deoxyadenosine (A2'N3) | | $N_3$ | No |
| 2'-fluoro-2'-deoxyadenosine (A2'F) | | F | No |

Non-limiting examples of analogs of G are shown in TABLE 4.

TABLE 4

| Name | Base modification (5'-position) | Sugar modification (2'-position) | Naturally in mRNA |
|---|---|---|---|
| N1-methylguanosine (m1G) | $CH_3$ (in position 1) | | No |
| 2'-0-methylguanosine (G2'm) | | $CH_3$ | Yes |
| 2'-amino-3'-deoxyguanosine (G2'NH2) | | $NH_2$ | No |
| 2'-azido-2'-deoxyguanosine (G2'N3) | | $N_3$ | No |
| 2'-fluoro-2'-deoxyguanosine (G2'F) | | F | No |

In certain embodiments, an analog (e.g., a modified nucleotide) can be selected from the group comprising pyridin-4-one ribonucleoside, 5-iodouridine, 5-iodocytidine, 5-aza-uridine, 2'-amino-2'-deoxycytidine, 2'-fluor-2'-deoxycytidine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, 5-methylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In certain embodiments, a modified polyribonucleotide of the disclosure does not include pseudouridine. In certain embodiments, a modified polyribonucleotide of the disclosure does not include 5-methyl cytidine. In certain embodiments, a modified polyribonucleotide of the disclosure does not include 5-methyl uridine. In certain embodiments, a modified polyribonucleotide of the disclosure comprises analogs of U and analogs of C, wherein such analogs of U may all be the same analog or may be different analogs (e.g., more than one type of analog), and wherein such analogs of C may all be the same analog or may be different analogs (e.g., more than one type of analog). In certain embodiments, a modified polyribonucleotide of the disclosure does not include analogs of adenosine and analogs of guanosine. In other embodiments, a modified polyribonucleotide of the disclosure does include analogs of adenosine and/or analogs of guanosine (in the presence or absence of analogs of cytidine and/or analogs of uridine).

As described in detail herein, when a polyribonucleotide comprises a modified polyribonucleotide, analogs may be present as a certain proportion of the nucleotides in the compound (e.g., a given percentage of a given nucleobase may be analog, as described herein). Analogs present in a polyribonucleotide may also be described based on the input percentage of analog used during synthesis/in vitro preparation. Methods of making modified polyribonucleotides of the disclosure are similarly contemplated.

The disclosure contemplates modified polyribonucleotides wherein a given percentage of A, U, C or G is analog (e.g, a given percentage of 1 of the 4 nucleotides). Such percentage may be, for example 5-50%, 3-5%, or greater than 50% (e.g., even 100%, or any other percentage or range disclosed herein). In certain embodiments, the single nucleotide is U or C. In other embodiments, the disclosure contemplates modified polyribonucleotides wherein a given percentage of at least two (or two) of A, U, C or G is analog. Such percentage may be, for example 5-50%, 3-5%, or greater than 50% (e.g., even 100%, or any other percentage or range disclosed herein) taken on a per nucleobase basis or across both nucleobases. In certain embodiments, the two nucleotides are U and C.

Modified Polyribonucleotides

A polyribonucleotide that comprises at least one modified nucleotide is a modified polyribonucleotide. In certain embodiments, at least about 3%, at least about 4%, or at least about 5% of the modified polyribonucleotide includes analogs of (e.g., modified, or non-natural) adenosine, cytidine, guanosine, or uridine, such as the analog nucleotides described herein. In some cases, at least about 5%, 10%, 15%, 20%, 25%, 30%, 40%, 45%, 50% of the modified polyribonucleotide includes analogs of adenosine, cytidine, guanosine, or uridine. In some cases, at most about 50%, 45%, 40%, 35%, 30%, 25%, 20%, 15%, 10%, 5%, of the modified polyribonucleotide includes non-naturally occurring adenosine, cytidine, guanosine, or uridine. In certain embodiments, the modified polyribonucleotide includes analogs of more than one nucleotide, such as cytidine and uridine, and the foregoing percentages refer to the percentage of analogs of each such nucleotide.

In certain embodiments a modified polyribonucleotide of the present disclosure contains a combination of modified and unmodified nucleotides. Preferably, a modified polyribonucleotide molecule of the present disclosure contains a combination of modified and unmodified nucleotides as described in US 2012/0195936 A1, hereby incorporated by reference in its entirety. Such modified polyribonucleotide molecules and related molecules are also known and commercialized as "SNIM®-RNA". In certain embodiments, the RNA molecule described in US 2012/0195936 A1 is reported to show an increased stability and diminished immunogenicity. In certain embodiments, in such a modified polyribonucleotide molecule, 5 to 50% of the cytidines are analogs of C and 5 to 50% of the uridines are analogs of U. In certain embodiments, in such a modified polyribonucleotide molecule 5 to 40% of the cytidines are analogs of C and 5 to 40% of the uridines are analogs of U. In certain embodiments, in such a modified polyribonucleotide molecule 5 to 30% of the cytidines are analogs of C and 5 to 30% of the uridines are analogs of U. In certain embodiments, in such a modified polyribonucleotide molecule 10 to 30% of the cytidines are analogs of C and 10 to 30% of the uridines are analogs of U. In certain embodiments, in such a modified polyribonucleotide molecule 5 to 20% of the cytidines are analogs of C and 5 to 20% of the uridines are analogs of U. In certain embodiments, in such a modified polyribonucleotide molecule 5 to 10% of the cytidine nucleotides and 5 to 10% of the uridine nucleotides are modified. In certain embodiments, in such a modified polyribonucleotide molecule 25% of the cytidine nucleotides and 25% of the uridine nucleotides are modified. In certain embodiments, the adenosine- and guanosine-containing nucleotides can be unmodified. In certain embodiments, the adenosine and guanosine nucleotides can be unmodified or partially modified, and they are preferably present in unmodified form.

As noted above, in certain embodiments, analogs of U refers to a single type of analog of U. In certain embodiments, analogs of U refers to two or more types of analogs of U. In certain embodiments, analogs of C refers to a single type of analog of C. In certain embodiments, analogs of C refers to two or more types of analogs of C.

In certain embodiments, the percentage of cytidines in a polyribonucleotide that are analogs of cytidine is not the same as the percentage of uridines in the polyribonucleotide that are analogs of uridine. In certain embodiments, the percentage of analogs of cytidine is lower than the percentage of analogs of uridine. As noted above, this may be in the presence or the absence of analogs of adenosine and guanosine but, in certain embodiments, is in the absence of analogs of adenosine and analogs of guanosine. In certain embodiments, polyribonucleotides of the disclosure comprises less than 15%, less than 10%, less than 5% or less than 2% analogs of adenosine, analogs of guanosine or both.

In certain embodiments, a polyribonucleotide of the disclosure comprises analogs of cytidine and analogs of uridine, and 5 to 20% or 5 to 30% of the cytidines are analogs of cytidine and 25 to 45% or 25 to 50% of the uridines are analogs of uridine. In other words, the polyribonucleotide comprises modified and unmodified cytidines and modified and unmodified uridines, and 5 to 20% or 5 to 30% of the cytidines comprise analogs of cytidine while 25 to 45% or 25 to 50% of the uridines comprise analogs of uridine. In other embodiments, the polyribonucleotide comprises 5 to 10% analogs of cytidine and 30 to 40% analogs of uridine, such as 7-9% analogs of cytidine, such as about 7, 7.5 or 8% and, such as 32-38% analogs of uridine, such as about 33, 34, 35, 36%. In certain embodiments, the percentage of analogs of cytidine is less than 5%, such as about 3-less than 5% or 3-5%.

In other embodiments, a polyribonucleotide of the disclosure comprises analogs of cytidine and/or uridine, and greater than 50% (even 100%) of the cytidine and/or uridine are analogs of cytidine or uridine, respectively.

In certain embodiments, any of the analogs of uridine and analogs of cytidine described herein may be used, optionally excluding pseudouridine. In certain embodiments, the analog of cytidine comprises or consists of (e.g., in the case of consists of, it is the single analog type used) 5-iodocytidine and the analog of uridine comprises or consists of (e.g., in the case of consists of, it is the single analog type used) 5-iodouridine.

In certain embodiments of any of the foregoing, the percentage of analogs of a given nucleotide refers to input percentage (e.g., the percentage of analogs in a starting reaction, such as a starting in vitro transcription reaction). In certain embodiments of any of the foregoing, the percentage of analogs of a given nucleotide refers to output (e.g., the percentage in a synthesized or transcribed compound). Any of the foregoing percentages can be used to describe either.

The polyribonucleotide molecules of the present disclosure may be produced recombinantly in in vivo systems by methods known to a person skilled in the art. Alternatively, the modified polyribonucleotide molecules of the present disclosure may be produced in an in vitro system using, for example, an in vitro transcription system. In vitro transcription systems are commonly known and usually require a purified linear DNA template containing a DNA sequence "encoding" the RNA molecule wherein said DNA sequence is under the control of an appropriate promoter. Moreover, an in vitro transcription system also commonly requires ribonucleoside triphosphates, a buffer system that includes DTT and magnesium ions, and an appropriate RNA polymerase which provides the enzymatic activity for the in vitro transcription of the DNA sequence into a corresponding RNA molecule of the present disclosure.

An in vitro transcription system capable of producing polyribonucleotides requires an input mixture of modified and unmodified nucleoside triphosphates to produce modified polyribonucleotides with the desired properties of the present disclosure. In certain embodiments, 5 to 50% of the cytidines are analogs of cytidine in such an input mixture and 5 to 50% of the uridines are analogs of uridine in such an input mixture. In certain embodiments, 5 to 40% of the cytidines are analogs of cytidine in such an input mixture and 5 to 40% of the uridines are analogs of uridine in such an input mixture. In certain embodiments, 5 to 30% of the cytidines are analogs of cytidine in such a mixture and 5 to 30% of the uridines are analogs of uridine in such an input mixture. In certain embodiments, 5 to 30% of the cytidines are analogs of cytidine in such mixture and 10 to 30% of the uridines are analogs of uridine in such mixture. In certain embodiments, 5 to 20% of the cytidines are analogs of cytidine in such an input mixture and 5 to 20% of the uridines are analogs of uridine in such an input mixture. In certain embodiments, 5 to 10% of the cytidines are analogs of cytidine in such an input mixture and 5 to 10% of the uridines are analogs of uridine in such an input mixture. In certain embodiments, 25% of the cytidines are analogs of cytidine in such an input mixture and 25% of the uridines are analogs of uridine in such an input mixture. In certain embodiments, the input mixture does not comprise analogs of adenosine and/or guanosine. In other embodiments, optionally, the input mixture comprises one or more analogs of adenosine and/or guanosine (or none of either or both). Moreover, for modified polyribonucleotides containing only one of analogs of U, C, A, or G, the in vitro reaction would include the appropriate input percentage of only analogs of that nucleotide. When a single nucleotide is the source of all modification, any of the percentages recited herein are contemplate, as are higher percentages of analog (e.g., greater than 50% or even 100%).

In certain embodiments, the percentage of cytidines in an input mixture that are analogs of cytidine is not the same as the percentage of uridines in an input mixture that are analogs of uridine. In certain embodiments, the percentage of analogs of cytidine in an input mixture is lower than the percentage of analogs of uridine in an input mixture. As noted above, this may be in the presence or the absence of analogs of adenosine and guanosine in the input mixture but, in certain embodiments, is in the absence of analogs of adenosine and analogs of guanosine in the input mixture.

In certain embodiments, an input mixture of nucleotides for an in vitro transcription system that produces a polyribonucleotide of the disclosure comprises analogs of cytidine and analogs of uridine, and 5 to 20% or 5 to 30% of the cytidines of the input mixture are analogs of cytidine and 25 to 45% or 25 to 50% of the uridines of the input mixture are analogs of uridine. In other words, the input mixture comprises modified and unmodified cytidines and modified and unmodified uridines, and 5 to 20% or 5 to 30% of the cytidines of the input mixture comprise analogs of cytidine while 25 to 45% or 25 to 50% of the uridines of the input mixture comprise analogs of uridine. In other embodiments, the input mixture comprises 5 to 10% analogs of cytidine and 30 to 40% analogs of uridine, such as 7-9% analogs of cytidine, such as 7, 7.5 or 8% and, such as 32-38% analogs of uridine, such as 33, 34, 35, 36%.

In certain embodiments, any of the analogs of uridine and analogs of cytidine described herein may be used, optionally excluding pseudouridine. In certain embodiments, the analog of cytidine comprises or consists of (e.g., it is the single C analog type used) 5-iodocytidine and the analog of uridine comprises or consists of (e.g., it is the single U analog type used) 5-iodouridine.

Exemplary analogs are described in the tables above. It should be understood that for modified polyribonucleotides encoding ornithine transcarbamylase (OTC), the analogs and level of modification is, unless indicated otherwise, considered across the entire polyribonucleotide encoding ornithine transcarbamylase (OTC), including 5' and 3' untranslated regions (e.g., the level of modification is based on input ratios of analogs in an in vitro transcription reaction such that analogs may be incorporated at positions that are transcribed).

The modified polyribonucleotide molecules may be chemically synthesized, for example by conventional chemical synthesis on an automated nucleotide sequence synthesizer using a solid-phase support and standard techniques.

Translation efficiency is the rate at which a polyribonucleotide is translated into polypeptides or proteins within cells. The translation efficiency of a given polyribonucleotide can be measured as the number of proteins or polypeptides which are translated per polyribonucleotide per unit time. Translation is the process in which cellular ribosomes create proteins by translating the coding region of a polyribonucleotide into the specific primary amino acid sequence of a protein; translation is well-known to those skilled in the art.

In certain embodiments, the translation efficiency of a modified polyribonucleotide molecule of the present disclosure is higher in comparison to a translation efficiency of an unmodified polyribonucleotide molecule of the same primary sequence that does not comprise nucleotide analogs (i.e. modified nucleotides). Accordingly, the number of ornithine transcarbamylase (OTC) proteins or polypeptides translated from the ornithine transcarbamylase (OTC) gene of a modified polyribonucleotide per modified polyribonucleotide per time unit may be higher than the number of ornithine transcarbamylase (OTC) proteins or polypeptides translated from the ornithine transcarbamylase (OTC) gene of the unmodified polyribonucleotide molecule of the same primary sequence that does not comprise nucleotide analogs (i.e. modified nucleotides) per polyribonucleotide per time unit. In other words, in certain embodiments, a modified polyribonucleotide of the present disclosure may be translated more efficiently in the cells of a subject as compared to the unmodified polyribonucleotide molecule of the same primary sequence that does not comprise nucleotide analogs (i.e. modified nucleotides).

In other embodiments, the translation efficiency is the same or substantially the same. This may be cell-type specific. Nevertheless, other differences may be apparent, such as decreased immunogenicity for modified polyribonucleotides, improved stability, increased half-life, and the like.

The translation efficiency can be determined by methods known in the art and as outlined in the following. Translation efficiency, in the context of the present disclosure, is the rate at which a polyribonucleotide is translated into protein within a cell at a given time point in relation to the amount of polyribonucleotide encoding said protein in said cell at the same time point. Thus, the translation efficiency is equal to the quantity of polyribonucleotide being translated into a protein within a cell at a given time point divided by the total quantity of polyribonucleotide encoding said protein within said cell at said time point. Both parameters, i.e., the quantity of polyribonucleotide being translated into a protein as well as the total quantity of polyribonucleotide encoding said protein, can be determined by methods known in the art. As a non-limiting example, the quantity of polyribonucleotide translated into a protein within a cell can be determined by flow cytometry while the total quantity of polyribonucleotide encoding said protein can be measured by qPCR.

The stability of an mRNA is a measure of how long it exists in a cell before being degraded. mRNA is degraded in vivo by a number of pathways known in the art. The stability of an mRNA can be measured as the half-life of the mRNA. An mRNA half-life is the time required for the quantity of that mRNA present in a sample or (a) cell(s) to reduce by half.

In certain embodiments, modified polyribonucleotide molecules of the present disclosure have enhanced stability in cells of a subject as compared to unmodified polyribonucleotide molecules of the same primary sequence that do not comprise nucleotide analogs (i.e. modified nucleotides). Accordingly, the half-life of a modified polyribonucleotide of the present disclosure is preferably longer (i.e. a greater time period) than the half-life of unmodified polyribonucleotide molecules of the same primary sequence that do not comprise nucleotide analogs (i.e. modified nucleotides). In certain embodiments, enhanced stability may be difficult to observe in cells in culture and may only become apparent in vivo. In other embodiments, stability is the same or substantially the same.

Untranslated Regions

A polyribonucleotide or a modified polyribonucleotide of the disclosure can comprise one or more untranslated regions. Similar to as described above, sequence in one or both untranslated regions may be optionally modified and, if modified, may be modified at the same percentages and for the same residues as described above, all of which is equally applicable here. An untranslated region can comprise any number of modified or unmodified nucleotides. Untranslated regions (UTRs) of a gene are transcribed but not translated into a polypeptide.

In some cases, a UTR can enhance expression of an associated gene and thus the expression of the protein that gene encodes. In a modified polyribonucleotide of the present disclosure, a UTR can enhance expression of an ornithine transcarbamylase (OTC) protein. "Enhance expression" may include one or both of the following effects: increase the stability of the nucleic acid molecule, and increase the efficiency of translation. A UTR can also comprise sequences that ensure controlled down-regulation of the associated transcript in case the polyribonucleotide molecules are misdirected to undesired organs or sites.

UTRs are positioned upstream (5') of the start codon of a modified polyribonucleotide of the disclosure and/or downstream (3') of the stop codon of a modified polyribonucleotide of the disclosure. UTRs are also encoded in a DNA sequence, as will be discussed below. As used in the present disclosure, the 5' untranslated region (5' UTR) (also known as a Leader Sequence or Leader RNA) is the region that is directly upstream from the start codon. In a ribonucleotide, the 5' UTR typically begins at the transcription start site and ends one nucleotide (nt) before the start codon (usually AUG) of the coding region. Native UTRs naturally occurring in messages of prokaryotes tend to have a length of 3-10 nucleotides. In contrast, native UTRs naturally occurring in eukaryotes tend to be longer, generally from 100 to several thousand nucleotides (although they can be shorter). The 5' UTR, once transcribed, may contain, inter alia, sequences which correspond to (residual 3') parts of the promoter as well as a so-called Kozak sequence. A Kozak sequence may be required for ribosome recognition and translation of many genes. Kozak sequences can have the consensus CCR(A/G)CC, where R is a purine (adenine or guanine) that is located three bases upstream of the start codon (AUG). 5' UTRs may form secondary structures which are involved in binding of translation elongation factor. In some cases, one can increase the stability and protein production of the engineered polynucleotide molecules of the disclosure by engineering the features typically found in abundantly expressed genes of specific target organs. For example, introduction of a 5'UTR of liver-expressed mRNA, such as albumin, serum amyloid A, Apolipoprotein A/B/E, transferrin, alpha fetoprotein, erythropoietin, or Factor VIII, can be used to increase expression of a modified polyribonucleotide in a liver. Likewise, use of a 5' UTR from muscle proteins (MyoD, Myosin, Myoglobin, Myogenin, Herculin), for endothelial cells (Tie-1, CD36), for myeloid cells (C/EBP, AML1, G-CSF, GM-CSF, CD1 lb, MSR, Fr-1, i-NOS), for leukocytes (CD45, CD18), for adipose tissue (CD36, GLUT4, ACRP30, adiponectin) and for lung epithelial cells (SP-A/B/C/D) can be used to increase expression of a modified polynucleotide in a desired cell or tissue. In some cases a UTR of the disclosure can be derived from the sequence of a cytochrome b-245 alpha polypeptide (CYBA); in such a case, a 5' UTR of the disclosure can comprise SEQ ID NO: 18 or SEQ ID NO: 20, and a 3' UTR of the disclosure can comprise SEQ ID NO: 19. As shown in the appended Examples, such UTRs lead to a higher expression (higher translation) and consequently higher OTC activity (measured as enzymatic activity) compared to the natural OTC UTRs or a “minimal” UTR.

In some cases a UTR of the disclosure can be derived from an α-globin gene; in such a case, a 5' UTR of the disclosure can comprise sequences derived from an a-globin gene, with (SEQ ID NOs: 12, 28) or without (SEQ ID NOs: 13, 29) a portion of an upstream promoter sequence.

As shown in the appended Examples, such UTRs are particularly useful because they lead to a higher expression (higher translation) and consequently higher OTC activity (measured as enzymatic activity) compared to the natural OTC UTRs or a “minimal” UTR and even when compared to a CYBA UTR.

In some cases a 5' UTR of the disclosure can comprise a TISU element with (SEQ ID NO: 14) or without (SEQ ID NO: 15) a portion of an upstream promoter sequence. In some cases a 5' UTR of the disclosure can comprise a TISU+T element with (SEQ ID NO: 16) or without (SEQ ID NO: 17) a portion of an upstream promoter sequence. In some cases a 5' UTR of the disclosure can comprise a 3' UTR derived from the sequence of human growth hormone (hGH) (SEQ ID NO: 30).

In certain embodiments, a modified polyribonucleotide of the disclosure comprises one or more UTRs selected from the sequences listed in Table 5.

TABLE 5

| UTRs | |
|---|---|
| UTR | RNA sequence (from 5' to 3') |
| CYBA 5' | CCGCGCCUAGCAGUGUCCCAGCCGGGUUCGUGUCGCCG CCACC (SEQ ID NO: 18) |
| CYBA 3' | CCUCGCCCCGGACCUGCCCUCCCGCCAGGUGCACCCAC CTGCAAUAAAUGCAGCGAAGCCGGGA (SEQ ID NO: 19) |
| α-globin 5' UTR (hAg) | GGGAGACUCU UCUGGUCCCCACAGACUCAG AGAGAA CGCCACC (SEQ ID NO: 12) |
| α-globin 5' UTR (HBA2) | cauaaacccuggcgcgcucgcgggccggcacucuucug gucccccacagacucagagagaacccacc (SEQ ID NO: 28) |
| α-globin 5′ UTR ETH | cucuucugguccccacagacucagagagaacgccacc (SEQ ID NO: 13) |
| hGH 3' UTR | CGGGUGGCAUCCCUGUGACCCCUCCCCAGUGCCUCUC CUGGCCCUGGAAGUUGCCACUCCAGUGCCCACCAGCC UUGUCCUAAUAAAAUUAAGUUGCAUC (SEQ ID NO: 30) |
| Minimal 5' UTR | GGGAGACGCCACC (SEQ ID NO: 10) |

TABLE 5-continued

| UTRs | |
|---|---|
| UTR | RNA sequence (from 5' to 3') |
| TISU 5' UTR | GGGAGACGCCAAG (SEQ ID NO: 14) |
| TISU + T 5' UTR | GGGAGACUGCCAAG (SEQ ID NO: 16) |

As used in the present disclosure, the 3' untranslated region (3'-UTR) relates to the section of a modified polyribonucleotide that immediately follows the translation termination codon (the stop codon) of a sequence encoding an ornithine transcarbamylase (OTC) protein. As used in the present disclosure, the 3' UTR may comprise regulatory regions which are known to influence polyadenylation and stability of a polyribonucleotide. A 3'-UTR can also comprise AU-rich elements (AREs). A 3'-UTR of the present disclosure can comprise the sequence AAUAAA that directs addition of several to several hundred adenine residues called the poly(A) tail to the end of the coding region of a polyribonucleotide.

3' UTRs may have stretches of adenosines and uridines embedded therein. These AU rich signatures are particularly prevalent in genes with high rates of turnover. Based on their sequence features and functional properties, the AU rich elements (AREs) can be separated into classes: Class I AREs contain several dispersed copies of an AUUUA motif within U-rich regions. C-Myc and MyoD contain class I AREs. Class II AREs possess two or more overlapping UUAUUUA (U/A)(U/A) nonamers. Molecules containing this type of AREs include GM-CSF and TNF-. Class III ARES are less well defined. These U rich regions do not contain an AUUUA motif c-Jun and Myogenin are two well-studied examples of this class. Proteins binding to the AREs may destabilize the messenger, whereas members of the ELAV family, such as HuR, may increase the stability of mRNA. HuR may bind to AREs of all the three classes. Engineering the HuR specific binding sites into the 3' UTR of nucleic acid molecules can lead to HuR binding and thus, stabilization of the message in vivo.

Engineering of 3' UTR AU rich elements (AREs) can be used to modulate the stability of a polyribonucleotide of the disclosure encoding an ornithine transcarbamylase (OTC). One or more copies of an ARE can be engineered into a polyribonucleotide to modulate the stability of a polyribonucleotide. AREs can be identified, removed or mutated to increase the intracellular stability and thus increase translation and production of the resultant protein. Transfection experiments can be conducted in relevant cell lines, using engineered polyribonucleotides and protein production can be assayed at various time points post-transfection. For example, cells can be transfected with different ARE-engineering molecules and by using an ELISA kit to the relevant protein and assaying protein produced at 6 hours, 12 hours, 24 hours, 48 hours, and 7 days post-transfection.

A 3' UTR of a modified polyribonucleotide encoding an ornithine transcarbamylase (OTC) protein of the present disclosure may also contain a poly-A tail. A poly-A tail is a long sequence of adenine nucleotides (often 100 or even several hundred) added to the 3' end of a pre-mRNA by a process called polyadenylation. As used herein, a poly-A tail relates to a sequence of adenine nucleotides located at the 3' end of the polyribonucleotide. A 3' UTR of a polyribonucleotide of the present disclosure may comprise a sequence for a poly-A tail or said 3' UTR may comprise polyadenylation signal sequences that signal polyadenylation of the polyribonucleotide intracellularly. Thus, the present disclosure relates to any of the above-described polyribonucleotides, wherein the polyribonucleotide comprises a poly-A tail at the 3' end.

A modified polyribonucleotide of the disclosure encoding ornithine transcarbamylase (OTC) can comprise an engineered 5' cap, or a 5' cap can be added to a polyribonucleotide intracellularly. The 5' cap structure of an mRNA can be involved in binding to the mRNA Cap Binding Protein (CBP), which is responsible for mRNA stability in the cell and translation competency through the association of CBP with poly(A) binding protein to form the mature cyclic mRNA species. The 5' cap structure can also be involved in nuclear export, increases in mRNA stability, and in assisting the removal of 5' proximal introns during mRNA splicing.

A modified polyribonucleotide can be 5'-end capped generating a 5'-ppp-5'-triphosphate linkage between a terminal guanosine cap residue and the 5'-terminal transcribed sense nucleotide of the polyribonucleotide molecule. The cap-structure can comprise a modified or unmodified 7-methyl-guanosine linked to the first nucleotide via a 5'-5' triphosphate bridge. This 5'-guanylate cap can then be methylated to generate an N7-methyl-guanylate residue. The ribose sugars of the terminal and/or anteterminal transcribed nucleotides of the 5'end of the polyribonucleotide may optionally also be 2'-O-methylated. 5'-decapping through hydrolysis and cleavage of the guanylate cap structure may target a nucleic acid molecule, such as a polyribonucleotide molecule of the disclosure, for degradation.

In some cases, a cap can comprise further modifications, including the methylation of the 2' hydroxy-groups of the first 2 ribose sugars of the 5' end of the polyribonucleotide. For instance, a eukaryotic cap-1 has a methylated 2'-hydroxy group on the first ribose sugar, while a cap-2 has methylated 2'-hydroxy groups on the first two ribose sugars. The 5' cap can be chemically similar to the 3' end of an polyribonucleotide molecule (the 5' carbon of the cap ribose is bonded, and the 3' unbonded). Such double modification can provides significant resistance to 5' exonucleases. Non-limiting examples of 5' cap structures that can be used with an engineered polyribonucleotide include, but are not limited to, 7mG(5')ppp(5')N, pN2p (cap 0), 7mG(5')ppp(5')NImpNp (cap 1), and 7mG(5')-ppp(5')NImpN2mp (cap 2).

Modifications to the modified polyribonucleotide of the present disclosure may generate a non-hydrolyzable cap structure preventing decapping and thus increasing polyribonucleotide half-life. Because cap structure hydrolysis requires cleavage of 5'-ppp-5'phosphorodiester linkages, modified nucleotides may be used during the capping reaction. For example, a Vaccinia Capping Enzyme from New England Biolabs (Ipswich, Mass.) may be used with a-thio-guanosine nucleotides according to the manufacturer's instructions to create a phosphorothioate linkage in the 5'-ppp-5' cap. Additional modified guanosine nucleotides may be used such as a-methyl-phosphonate and seleno-phosphate nucleotides. Additional modifications include, but are not limited to, 2'-O-methylation of the ribose sugars of 5'-terminal and/or 5'-anteterminal nucleotides of the mRNA on the 2'-hydroxyl group of the sugar ring. Multiple distinct 5'-cap structures can be used to generate the 5'-cap of a polyribonucleotide.

The modified polyribonucleotide may be capped post-transcriptionally. According to the present disclosure, 5' terminal caps may include endogenous caps or cap analogues.

Further, a modified polyribonucleotide can contain one or more internal ribosome entry site(s) (IRES). IRES sequences can initiate protein synthesis in the absence of the 5' cap structure. An IRES sequence can also be the sole ribosome binding site, or it can serve as one of multiple ribosome binding sites of a polyribonucleotide. Modified polyribonucleotides containing more than one functional ribosome binding site can encode several peptides or polypeptides that are translated by the ribosomes ("polycistronic or multicistronic polyribonucleotides"). A modified polyribonucleotide described here can comprise at least one IRES sequence, two IRES sequences, three IRES sequences, four IRES sequences, five IRES sequences, six IRES sequences, seven IRES sequences, eight IRES sequences, nine IRES sequences, ten IRES sequences, or another suitable number are present in a modified polyribonucleotide. Examples of IRES sequences that can be used according to the present disclosure include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV). An IRES sequence can be derived, for example, from commercially available vectors such as the IRES sequences available from Clontech™, GeneCopoeia™, Sigma-Aldrich™. IRES sequences can be, for example, at least 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, or 10000 bases or base pairs. IRES sequences can be at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, 100 bases or base pairs, 50 bases or base pairs, or 10 bases or base pairs. In certain embodiments, a polyribonucleotide of the disclosure may comprise an m7GpppG cap, an internal ribosome entry site (IRES) and/or a polyA tail at the 3' end in particular in order to improve translation. The RNA can have further regions promoting translation.

A polynucleotide sequence that may transcribe a modified polyribonucleotide of the disclosure can comprise one or more promoter sequences and any associated regulatory sequences, either a whole promoter and associated regulatory sequences or a fragment thereof. mRNA is transcribed from a gene by a DNA-dependent RNA polymerase, which begins transcribing at the transcription start site (TSS). The position of the TSS is determined by the specific promoter sequence and any other regulatory sequences upstream of the start codon of the gene. The TSS may be within the promoter sequence. Thus the 5' UTR of a modified polyribonucleotide may comprise a portion of a promoter sequence. The promoter sequence and any associated regulatory sequence or portion thereof can be positioned at the 5' end of the 5' UTR. A promoter sequence and/or an associated regulatory sequence can comprise any number of modified or unmodified nucleotides. Promoter sequences and/or any associated regulatory sequences can comprise, for example, at least 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, or at least 10000 bases or base pairs. A promoter sequence and/or an associated regulatory sequence can comprise any number of modified or unmodified nucleotides, for example, at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, or 100 bases or base pairs. DNA sequences of promoters of the disclosure include, but are not limited to, the sequences listed in Table 6. As the present disclosure also concerns modified polyribonucleotides, RNA sequences versions of the promoters listed in Table 6 may be found in Table 6.

TABLE 6

| Promoter Name | RNA Sequence and SEQ ID NO. |
|---|---|
| T7 | UAAUACGACUCACUAUAGGGAGA (SEQ ID NO: 6) |
| T3 | AAUUAACCCUCACUAAAGGGAGA (SEQ ID NO: 7) |
| SP6 | AUUUAGGUGACACUAUAGAAG (SEQ ID NO: 8) |
| K11 | AAUUAGGGCACACUAUAGGGA (SEQ ID NO: 9) |

We note that portions of the DNA sequence from the templates/plasmids used to generate polyribonucleotides of the disclosure are provided herein. The entire plasmid sequence is not provided, rather templates comprising the provided DNA sequences were used and are provided.

In certain embodiments, a modified polyribonucleotide molecule of the present disclosure comprises a 5' UTR comprising the nucleotide sequence of SEQ ID NO: 18 or a sequence which shows 1 to 4 substitutions (or, in certain embodiments, additions or deletions) in comparison to SEQ ID NO: 18. In some embodiments, such a polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 18 or a sequence which shows 1 to 4 substitutions (or, in certain embodiments, additions or deletions) in comparison to SEQ ID NO: 18. In some embodiments, such a polyribonucleotide has the same or higher translation efficiency compared to a polyribonucleotide without the 5' UTR.

In certain embodiments, a modified polyribonucleotide molecule of the present disclosure comprises a 3' UTR comprising the nucleotide sequence of SEQ ID NO: 19 or a sequence which shows 1 to 4 substitutions (or, in certain embodiments, additions or deletions) in comparison to SEQ ID NO: 30. In some embodiments, such a polyribonucleotide has the same or higher translation efficiency compared to a polyribonucleotide without the 3' UTR. In another embodiment, a modified polyribonucleotide molecule of the present disclosure comprises a 3' UTR comprising two or more copies of the nucleotide sequence of SEQ ID NO: 19 or a sequence which shows 1 to 4 substitutions (or, in certain embodiments, additions or deletions) in comparison to SEQ ID NO: 19. In some embodiments, the polyribonucleotide has the same or higher translation efficiency compared to a polyribonucleotide without the 3' UTR.

In certain embodiments, a modified polyribonucleotide molecule of the present disclosure comprises a 5' UTR comprising the nucleotide sequence of SEQ ID NO: 12 or a sequence which shows 1 to 4 substitutions (or, in certain embodiments, additions or deletions) in comparison to SEQ ID NO: 12. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 13 (human alpha globin without promoter sequence) or a sequence which shows 1 to 4 substitutions (or, in certain embodiments, additions or deletions) in comparison to SEQ ID NO: 13. In certain embodiments, the polyribonucleotide has the same or higher translation efficiency compared to a polyribonucleotide without the 5' UTR.

In certain embodiments, a modified polyribonucleotide molecule of the present disclosure comprises a 5' UTR comprising the nucleotide sequence of SEQ ID NO: 28 or a sequence which shows 1 to 4 substitutions (or, in certain embodiments, additions or deletions) in comparison to SEQ ID NO: 28. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 28 or a sequence which shows 1 to 4 substitutions (or, in certain embodiments, additions or deletions) in comparison to SEQ ID NO: 28. In certain embodiments, the polyribonucleotide has the same or higher translation efficiency compared to a polyribonucleotide without the 5' UTR.

In certain embodiments, a modified polyribonucleotide molecule of the present disclosure comprises a 5' UTR comprising the nucleotide sequence of SEQ ID NO: 29 or a sequence which shows 1 to 4 substitutions (or, in certain embodiments, additions or deletions) in comparison to SEQ ID NO: 29. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 29 or a sequence which shows 1 to 4 substitutions (or, in certain embodiments, additions or deletions) in comparison to SEQ ID NO: 29. In certain embodiments, the polyribonucleotide has the same or higher translation efficiency compared to a polyribonucleotide without the 5' UTR.

In certain embodiments, a modified polyribonucleotide molecule of the present disclosure comprises a 3' UTR comprising the nucleotide sequence of SEQ ID NO: 30 or a sequence which shows 1 to 4 substitutions (or, in certain embodiments, additions or deletions) in comparison to SEQ ID NO: 30. In certain embodiments, the polyribonucleotide has the same or higher translation efficiency compared to a polyribonucleotide without the 3' UTR. In another embodiment, a modified polyribonucleotide molecule of the present disclosure comprises a 3' UTR comprising two or more copies of the nucleotide sequence of SEQ ID NO: 30 or a sequence which shows 1 to 4 substitutions (or, in certain embodiments, additions or deletions) in comparison to SEQ ID NO: 30. In certain embodiments, the polyribonucleotide has the same or higher translation efficiency compared to a polyribonucleotide without the 3' UTR.

In certain embodiments, a modified polyribonucleotide molecule of the present disclosure comprises a 5' UTR comprising the nucleotide sequence of SEQ ID NO: 10 or a sequence which shows 1 to 4 substitutions (or, in certain embodiments, additions or deletions) in comparison to SEQ ID NO: 10. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 11 or a sequence which shows 1 to 4 substitutions (or, in certain embodiments, additions or deletions) in comparison to SEQ ID NO: 11. In certain embodiments, the polyribonucleotide has the same or higher translation efficiency compared to a polyribonucleotide without the 5' UTR.

In certain embodiments, a modified polyribonucleotide molecule of the present disclosure comprises a 5' UTR comprising the nucleotide sequence of SEQ ID NO: 14 or a sequence which shows 1 to 4 substitutions (or, in certain embodiments, additions or deletions) in comparison to SEQ ID NO: 14. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 15 or a sequence which shows 1 to 4 substitutions (or, in certain embodiments, additions or deletions) in comparison to SEQ ID NO: 15. In certain embodiments, the polyribonucleotide has the same or higher translation efficiency compared to a polyribonucleotide without the 5' UTR.

In certain embodiments, a modified polyribonucleotide molecule of the present disclosure comprises a 5' UTR comprising the nucleotide sequence of SEQ ID NO: 16 or a sequence which shows 1 to 4 substitutions (or, in certain embodiments, additions or deletions) in comparison to SEQ ID NO: 16. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 17 or a sequence which shows 1 to 4 substitutions (or, in certain embodiments, additions or deletions) in comparison to SEQ ID NO: 17. In certain embodiments, the polyribonucleotide has the same or higher translation efficiency compared to a polyribonucleotide without the 5' UTR.

"Two or more" in the above embodiments means that the modified polyribonucleotide molecule may comprise a UTR comprising two, three, or four copies of the specified sequence, or a sequence which shows 1 to 4 substitutions (or, in certain embodiments, additions or deletions) in comparison to the specified sequence. Alternatively, the modified polyribonucleotide molecule may also comprise five or even more copies of the specified sequence within the UTR.

In certain embodiments, the 3' UTR comprises one or more copies of a 3' UTR sequence selected from the group consisting of SEQ ID NOs: 19 and 30, wherein the ribonucleotides of the 3' UTR are positioned downstream (3') of the ribonucleotides encoding the ornithine transcarbamylase (OTC) protein, such as the ribonucleotides of SEQ ID NO: 1 or 4, for example, directly downstream with less than 40 contiguous nucleotides intervening, less than 30, less than 20, less than 10, less than 5, less than 3, 3, 2, 1 or no contiguous nucleotides intervening.

In certain embodiments, the 5' UTR comprises one or more sequences selected from the group consisting of SEQ ID NOs: 11, 13, 15, 17 and 18, wherein the ribonucleotides of the 5' UTR are positioned upstream (5') of the ribonucleotides encoding the ornithine transcarbamylase (OTC) protein, such as the ribonucleotide of SEQ ID NO: 1 or 4, and 3' from ribonucleotides corresponding to a portion of a promoter sequence, for example, directly 3' with less than 40 contiguous nucleotides intervening, less than 30, less than 20, less than 10, less than 5, less than 3, 3, 2, 1 or no contiguous nucleotides intervening.

In certain embodiments, the modified polyribonucleotide of the disclosure encoding ornithine transcarbamylase (OTC) contains a combination of unmodified and modified ribonucleotides, wherein 30-45% or 30-50% or 25-50% of the uridines are analogs of uridine and 5-10% or 5-20% or 5-30% of the cytidines are analogs of cytidine. In certain embodiments, the modified polyribonucleotide contains a combination of unmodified and modified ribonucleotides, wherein 30-45% or 30-50% or 25-50% of uridines in said input mixture are analogs of uridine and 5-10% or 5-20% or 5-30% of cytidines in said input mixture are analogs of cytidine. Also contemplated are such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes an ornithine transcarbamylase (OTC), protein comprising an amino acid sequence at least 90%, 91%, 92%, 93%, 94%, 95%, 96%, 97%, 98%, 99% or 100% identical thereto.

The present disclosure is not particularly limited to modified polyribonucleotides comprising UTRs listed in Table 5, but may also relate to (an) UTR sequence(s) which comprise(s) a sequence which shows (a) nucleotide(s) addition(s) or deletion(s) in comparison to sequences listed in Table 5. The addition of (a) nucleotide(s) can be flanking. Thus, the additional nucleotide(s) may be added at the 3'-end or 5'-end of the UTR(s) of the present disclosure. The additional nucleotide(s) comprise polynucleotide chains of up to 0 (no changes), 1, 2, 3, 4, 5, 6, 7, 8, 9 or 10 nucleotides, preferably of up to 20 nucleotides or even more preferably of up to 30 nucleotides. In light of the rationale that the addition of nucleotides is likely not to change the above functional properties of the UTR(s) of the disclosure the addition of the nucleotides may also have a length of up to 40, 50, 60, 70, 80, 90, or even 100 nucleotides or even more, up to 200, 300, 400 or 500 nucleotides as long as these sequences have a similar capability (in terms of the above-described translation efficiency) as sequences described in Table 5, preferably higher translation efficiency as in Table 5 defined above.

Alternatively, or in addition to these flanking additions of (a) nucleotide(s) the addition of (a) nucleotide(s) can be interspersed. Thus, the additional nucleotide(s) may be added/inserted within the nucleotide sequence of the UTR(s) of the present disclosure. These nucleotide(s) insertions comprise 1, 2, or 3 nucleotides and, in some embodiments, result in sequences having a similar capability (in terms of the above-described translation efficiency) as sequences of Table 5, preferably higher translation efficiency as sequences of Table 5 as defined above.

A modified polyribonucleotide according to the present disclosure may not only comprise the three main modules of (i) ornithine transcarbamylase (OTC) protein encoding sequence, (ii) 5' UTR, and/or (iii) 3' UTR. Rather, it may be desirable that between the individual modules (a) linker moiety/moieties and/or (a) multiple cloning site(s) is/are placed which may, e.g., facilitate the construction of the modified polyribonucleotide. Suitable linker moieties and multiple cloning sites are known to the skilled person.

The position of the UTR modules within the modified polyribonucleotide molecule of the present disclosure in relation to the ornithine transcarbamylase (OTC) protein encoding sequence is not particularly limited and, accordingly, between the individual UTRs and ornithine transcarbamylase (OTC) protein encoding sequence of the modified polyribonucleotide molecule of the present disclosure there may be a spacing or a gap filled with one or more nucleotides G, A, U and/or C which are not part of the UTRs or the ornithine transcarbamylase (OTC) protein encoding sequence.

"One or more nucleotides G, A, U and/or C" in this context means that the spacing or gap between the individual UTR(s) and the ornithine transcarbamylase (OTC) protein encoding sequence of the modified polyribonucleotide molecule of the present disclosure is/are filled with 1, 2, 3, 4, 5, 6, 7, 8, 9 or 10 nucleotides G, A, U and/or C. In certain embodiments, the spacing or gap between the individual UTR(s) and the ornithine transcarbamylase (OTC) protein encoding sequence of the modified polyribonucleotide molecule of the present disclosure are filled with 20, 30, 40, 50, 60, 70, 80, 90, 100 or 110 or more nucleotides G, A, U and/or C.

In certain embodiments, the 5' UTR(s), within the modified polyribonucleotide molecule of the present disclosure in relation to the ornithine transcarbamylase (OTC) protein encoding sequence is directly placed adjacent to the start codon of the coding region without any spacing or gap in between, i.e., directly upstream of the start codon of the coding region of the ornithine transcarbamylase (OTC) protein encoding sequence.

In another embodiment, the 3' UTR, within the modified polyribonucleotide molecule of the present disclosure in relation to the ornithine transcarbamylase (OTC) protein encoding sequence is directly placed adjacent to the termination codon (i.e., the stop codon) of the coding region without any spacing or gap in between, i.e., directly downstream of the termination codon/stop codon of the coding region of the ornithine transcarbamylase (OTC) protein encoding sequence.

In certain embodiments, the 5' UTR(s), within the modified polyribonucleotide molecule of the present disclosure in relation to the ornithine transcarbamylase (OTC) protein encoding sequence is directly placed adjacent to the start codon of the coding region without any spacing or gap in between, i.e., directly upstream of the start codon of the coding region of the ornithine transcarbamylase (OTC) protein encoding sequence, and the 3' UTR, within the modified polyribonucleotide molecule of the present disclosure in relation to the ornithine transcarbamylase (OTC) protein encoding sequence is directly placed adjacent to the termination codon (i.e., the stop codon) of the coding region without any spacing or gap in between, i.e., directly downstream of the termination codon/stop codon of the coding region of the ornithine transcarbamylase (OTC) protein encoding sequence.

In certain embodiments, the modified polyribonucleotide of the present disclosure encodes an ornithine transcarbamylase (OTC) protein, wherein said modified polynucleotide includes a codon sequence that is optimized for translation within cells of the subject exposed to the modified polyribonucleotide.

Other non-UTR sequences can be incorporated into the 5' (or 3' UTR) UTRs of the modified polyribonucleotides of the present disclosure. The 5' and/or 3' UTRs can provide stability and/or translation efficiency of polyribonucleotides. For example, introns or portions of intron sequences can be incorporated into the flanking regions of a polyribonucleotide. Incorporation of intronic sequences can also increase the rate of translation of the modified polyribonucleotide.

An untranslated region can comprise any number of nucleotides. An untranslated region can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. An untranslated region can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or 10000 bases or base pairs in length.

A modified polyribonucleotide of the disclosure can comprise one or more introns.

A modified polyribonucleotide of the disclosure can comprise a poly-A sequence. A poly-A sequence (e.g., poly-A tail) can comprise any number of nucleotides. A poly-A sequence can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, or even more than 500.

In some cases, a percentage of the nucleotides in a poly-A sequence are modified nucleotides. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in a poly-A sequence are modified nucleotides. In some cases, all of the nucleotides in a poly-A are modified nucleotides.

A linker sequence can comprise any number of nucleotides. A linker can be attached to the modified nucleobase at an N-3 or C-5 position. The linker attached to the nucleobase can be diethylene glycol, dipropylene glycol, triethylene glycol, tripropylene glycol, tetraethylene glycol, tetraethylene glycol, divalent alkyl, alkenyl, alkynyl moiety, ester, amide, or an ether moiety. A linker sequence can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. A linker sequence can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or at least 10000 bases or base pairs in length. A linker at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, or 100 bases or base pairs in length.

In some cases, a percentage of the nucleotides in a linker sequence are modified nucleotides. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in a linker sequence are modified nucleotides. In some cases, all of the nucleotides in a linker sequence are modified nucleotides.

In some cases, a modified polyribonucleotide can include at least one stop codon before the 3'untranslated region (UTR). In some cases, a modified polyribonucleotide includes multiple stop codons. The stop codon can be selected from TGA, TAA and TAG. The stop codon may comprise modified or unmodified nucleotides. In some cases, the modified polyribonucleotide includes the stop codon TGA and one additional stop codon. In some cases, the modified polyribonucleotide includes the addition of the TAA stop codon.

Encoded Ornithine Transcarbamylase (OTC) Polypeptides

The present disclosure provides polyribonucleotide molecules, preferably modified polyribonucleotide molecules comprising modified nucleotides (i.e. non-naturally occurring or analogs of uridine, cytidine, guanosine, and adenosine), which encode an ornithine transcarbamylase (OTC) protein. An encoded ornithine transcarbamylase (OTC) polypeptide is a polymer chain comprised of amino acid residue monomers which are joined together through amide bonds (peptide bonds). A polyribonucleotide that is translated within a subject's body can generate an ample supply of encoded ornithine transcarbamylase (OTC) protein within a cell, a tissue, or across many cells and tissues of a subject. In some cases, a polyribonucleotide can be translated in vivo within the cytosol of a specific target cell(s) type or target tissue. In some cases the translated polypeptide is transported into the mitochondria. In some cases, a modified polyribonucleotide of the present disclosure can be translated in vivo to provide an ornithine transcarbamylase (OTC) protein.

In some embodiments the ornithine transcarbamylase (OTC) protein is expressed in cells derived from the appendix, the liver, the duodenum, the small intestine, the colon or the rectum, more preferably in cells derived from colon or rectum, most preferably in liver and duodenum cells.

A polynucleotide sequence encoding an ornithine transcarbamylase (OTC) protein can be derived from one or more mammalian or non-mammalian species. In some embodiments the ornithine transcarbamylase (OTC) is derived from one or more mammalian species. In some embodiments the ornithine transcarbamylase (OTC) is derived from dog, cow, mouse, rat, or human. In some cases the ornithine transcarbamylase (OTC) is a human protein. In some cases the ornithine transcarbamylase (OTC) protein is derived from a non-human mammalian species. In some cases the ornithine transcarbamylase (OTC) protein is derived from chicken, frog or zebrafish.

In some cases the ornithine transcarbamylase (OTC) protein is derived from a plant. In some cases the ornithine transcarbamylase (OTC) protein is derived from A. thaliana. In some cases the ornithine transcarbamylase (OTC) protein is derived from a fungus. In some cases the ornithine transcarbamylase (OTC) protein is derived from *S. cerevisiae, S. pombe, Eremothecium gossypii, Kluyveromyces lactis, Magnaporthe oryzae* or *Neurospora crassa*. A polynucleotide sequence can be a chimeric combination of the sequence of one or more species.

Unmodified sequences of exemplary ornithine transcarbamylase (OTC) polyribonucleotides may be found in Horwich et al. (Science 224 (1984), 1068-1074); incorporated by reference herein. According to Horwich et al. the human OTC gene encodes a 354-amino acid protein which is synthesized as a precursor of about 40 kD. This pre-OTC has a 32 amino acid N-terminal leader peptide which is cleaved proteolytically concomitant with its import into mitochondria. In certain embodiments, a modified polyribonucleotide of the present disclosure encodes an ortholog or homolog of an ornithine transcarbamylase (OTC) protein of described or referred to herein.

The modified polyribonucleotide of the present disclosure encodes an ornithine transcarbamylase (OTC) protein. Ornithine transcarbamylase (OTC) (also called ornithine carbamoyltransferase) is an enzyme that catalyzes the reaction between carbamoyl phosphate (CP) and ornithine (Orn) to form citrulline (Cit) and phosphate ($P_i$).

In certain embodiments, a modified polyribonucleotide of the disclosure encodes a wildtype ornithine transcarbamylase (OTC) protein. In certain embodiments, a modified polyribonucleotide of the disclosure that encodes a wildtype ornithine transcarbamylase (OTC) protein has been codon optimized for expression in mammalian cells. In certain embodiments, a modified polyribonucleotide of the disclosure comprises a sequence greater than or equal to 75%, 80%, 85%, 90%, 95%, 96%, 97%, 98%, or 99% identical to SEQ ID NO: 1 or SEQ ID NO: 4. In certain embodiments, a modified polyribonucleotide of the disclosure comprises a sequence identical to SEQ ID NO: 1 or identical to SEQ ID NO: 4. SEQ ID NO:1 represents the coding region on the RNA level of the wildtype nucleotide sequence of human ornithine transcarbamylase (OTC) (NCBI accession number NM_000531.5). SEQ ID NO: 4 is a codon-optimized version of SEQ ID NO: 1 for improved expression in mammalian cells.

In certain embodiments, a protein encoded by a modified polyribonucleotide of the disclosure may have a post-translational modification. In certain embodiments, the modified polyribonucleotide contains a combination of unmodified and modified ribonucleotides, wherein 30-45% of the uridines are analogs of uridine and 5-10% of the cytidines are analogs of cytidine. In certain embodiments, the modified polyribonucleotide contains a combination of unmodified and modified ribonucleotides, wherein 30-45% of uridines in said input mixture are analogs of uridine and 5-10% of cytidines in said input mixture are analogs of cytidine Also contemplated is such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes a ornithine transcarbamylase (OTC) protein, such as a ornithine transcarbamylase (OTC) protein described herein, or a protein comprising an amino acid sequence at least 90%, 91%, 92%, 93%, 94%, 95%, 96%, 97%, 98%, 99% or 100% identical thereto.

Non-limiting examples of ornithine transcarbamylase (OTC)-encoding (ribo)nucleotide sequences that can be a part of a polynucleotide of the disclosure are disclosed in TABLE 7.

TABLE 7

| Name | Sequence Number |
|---|---|
| Wildtype human OTC (RNA) | SEQ ID NO: 1 |
| Wildtype human OTC (DNA) | SEQ ID NO: 2 |
| Codon-optimized human OTC (RNA) | SEQ ID NO: 4 |
| Codon-optimized human OTC (DNA) | SEQ ID NO: 5 |

Other examples of OTC-encoding nucleotide sequences are naturally occurring variations, e.g. mutations or polymorphisms as described, e.g., in Yamaguchi et al. (Hum. Mutat. 27 (2006), 626-632), as long as they encode a functional OTC enzyme.

A non-limiting example of the ornithine transcarbamylase (OTC) polypeptide sequence that can be encoded by a modified polyribonucleotide of the disclosure is disclosed in TABLE 8.

TABLE 8

| Name | Sequence Number |
|---|---|
| Wildtype OTC | SEQ ID NO: 3 |

Immunogenicity

The use of modified polyribonucleotides may increase stability and/or decrease immunogenicity versus unmodified polyribonucleotides. Thus, in some embodiments, use of a modified polyribonucleotide encoding an ornithine transcarbamylase (OTC) is preferred. Numerous methods for evaluating immunogenicity are known in the art. For example, one method is determining expression of inflammatory markers in cells following administration of a polyribonucleotide of the disclosure encoding ornithine transcarbamylase (OTC) versus expression or concentration of inflammatory markers in response to an ummodified polyribonucleotide having the same sequence. Cytokines which are associated with inflammation, such as for example TNF-α, IFN-α, IFN-β, IL-8, IL-6, IL-12 or other cytokines known to those skilled in the art may be evaluated. The expression of DC activation markers can also be used for the estimation of immunogenicity. A further indication of an immunological reaction is the detection of binding to the Toll-like receptors TLR-3, TLR-7, or TLR-8, and/or to helicase RIG-1.

The immunogenicity is as a rule determined in relation to a control. In a common method, either the modified polyribonucleotide according to the disclosure or a polyribonucleotide that is unmodified or modified in another way is administered to cells and the secretion of inflammatory markers in a defined time interval as a reaction to the administration of the polyribonucleotide is measured. As the standard used for comparison, either unmodified polyribonucleotide can be used, in which case the immune response should be lower, or polyribonucleotide which is known to cause little or no immune response, in which case the immune response to the modified polyribonucleotide according to the disclosure should then lie in the same range and not be elevated. With the modified polyribonucleotide according to the disclosure it is possible to lower the immune response compared to unmodified polyribonucleotide by at least 30%, as a rule at least 50% or even 75% or even to prevent it completely.

The immunogenicity can be determined by measurement of the aforesaid factors, in particular by measurement of the TNF-α and IL-8 levels and the binding capacity to TLR-3, TLR-7, TLR-8 and helicase RIG-1. In order thereby to establish whether a polyribonucleotide has the desired low immunogenicity, the quantity of one or more of the aforesaid factors after administration of the polyribonucleotide concerned can be measured. Thus for example a quantity of the polyribonucleotide to be tested can be administered to mice via the caudal vein or i.p. and then one or more of the aforesaid factors can be measured in the blood after a predefined period, e.g. after 7 or 14 days. The quantity of factor is then related to the quantity of factor which is present in the blood of untreated animals. For the determination of the immunogenicity it has been found very valuable to determine the binding capacity to TLR-3, TLR-7, TLR-8 and/or helicase RIG-1. The TNF-α levels and IL-8 levels also provide very good indications. With the modified polyribonucleotide according to the disclosure, it is possible to lower the binding capacity to TLR-3, TLR-7, TLR-8 and RIG-1 by at least 50% compared to unmodified RNA. As a rule it is possible to lower the binding to said factors by at least 75% or even by 80%. In preferred embodiments, the binding capacity to TLR-3, TLR-7, TLR-8 and RIG-1 lies in the same range for the modified polyribonucleotide according to the disclosure and for animals to which no mRNA was administered. In other words, the modified polyribonucleotide according to the disclosure causes practically no inflammatory or immunological reactions.

In some embodiments, modified polyribonucleotides encoding ornithine transcarbamylase (OTC) according to the disclosure have reduced immunogenicity versus a non-modified comparator.

In some embodiments, any of the polyribonucleotides encoding ornithine transcarbamylase (OTC) described herein may be described based on a decreased level of immunogenicity, or based on other function properties described herein.

Further properties of the polyribonucleotides encoding ornithine transcarbamylase (OTC) according to the disclosure which may be used are its efficiency and stability. Transcription efficiency, transfection efficiency, translation efficiency and duration of protein expression may be evaluated to see whether it is at least comparable to unmodified polyribonucleotide or, in some cases or for some properties, improved.

Examples of modified polyribonucleotide sequences of the disclosure include polyribonucleotides comprising SEQ ID Nos: 21-27. In certain embodiments, the modified polyribonucleotide contains a combination of unmodified and modified ribonucleotides, wherein 30-45% or 30-50% or 25-50% of the uridines are analogs of uridine and 5-10% or 5-20% or 5-30% of the cytidines are analogs of cytidine. In certain embodiments, the modified polyribonucleotide contains a combination of unmodified and modified ribonucleotides, wherein 30-45% or 30-50% or 25-50% of uridines in said input mixture are analogs of uridine and 5-10% or 5-20% or 5-30% of cytidines in said input mixture are analogs of cytidine. In certain embodiments, the cytidine analog is 5-iodocytidine and the uridine analog is 5-iodouridine. Also contemplated is such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes a ornithine transcarbamylase (OTC) protein, such as a ornithine transcarbamylase (OTC) protein described herein, or a protein comprising an amino acid sequence at least 90%, 91%, 92%, 93%, 94%, 95%, 96%, 97%, 98%, 99% or 100% identical thereto (e.g., to SEQ ID NO: 3, in the presence or the absence of the mitochondrial signal peptide).

Pharmaceutical Aspects

In a further aspect, the present disclosure relates to compositions for delivering a polyribonucleotide encoding ornithine transcarbamylase (OTC), according to the disclosure, preferably a modified polyribonucleotide, to tissue or into a target cell. Said delivery can be in vivo or in vitro.

Polyribonucleotides may be delivered as "naked" RNA or in combination with a delivery agent, e.g., a carrier, an encapsulating agent, a polymeric material, such as polyethylenimine (PEI), a nanoparticle, or a lipidoid. In certain embodiments, the ornithine transcarbamylase (OTC) encoding polyribonucleotide is formulated, such as in a nanoparticle or lipidoid. Methods and compositions for delivery of polyribonucleotides of the disclosure may be found, for example, in U.S. Pat. No. 8,871,230, U.S. Patent Application Publication No. 20150126589, US Patent Application 20126165745, and WO2014/207231, incorporated by reference herein.

The present disclosure also relates to a method for delivering a polyribonucleotide, preferably a modified polyribonucleotide, to a target cell or tissue comprising the step of bringing a composition according to the disclosure into contact with the target cell or tissue. Such a method can be carried out in vitro or in vivo and administration may be local or systemic. The bringing into contact may be achieved by means and methods known to the person skilled in the art. For example, if the method is carried out in vitro, the bringing into contact can be achieved by cultivating the cells in the presence of the composition in the culture medium or by adding the composition to the cells. If the method is carried out in vivo, the bringing into contact with cells or tissues can, e.g., be achieved by the administration of the composition to an individual by routes of administration known to the person skilled in the art, in particular by any route of administration that is usually employed in the field of genetic therapy. Possible ways of formulating the composition and of administering it to an individual are also described further below.

The term "in vivo" refers to any application which is effected to the body of a living organism wherein said organism is preferably multicellular, more preferably a mammal and most preferably a human. The term "in vitro" or "ex vivo" refers to any application performed outside an organism, including to cells or tissues isolated and outside of an organism, e.g. cells, tissues and organs, wherein said organism is preferably multicellular, more preferably a mammal and most preferably a human.

The present disclosure also relates to a pharmaceutical composition comprising the composition of the disclosure and optionally a pharmaceutically acceptable carrier and/or diluent.

The term "pharmaceutically acceptable form" means that the composition is formulated as a pharmaceutical composition, wherein said pharmaceutical composition may further comprise a pharmaceutically acceptable carrier and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. The dosage regimen will be determined by the attending physician and clinical factors. As is well known in the medical arts, dosages for any one subject depend upon many factors, including the subject's size, body surface area, age, the particular compound to be administered, sex, time and route of administration, general health, and other drugs being administered concurrently. A typical dose of active substances can be, for example, in the range of 1 ng to several grams. Applied to polyribonucleotide therapy, the dosage of an polyribonucleotide for expression or for inhibition of expression should correspond to this range; however, doses below or above this exemplary range are envisioned, especially considering the aforementioned factors. Generally, the regimen as a regular administration of the pharmaceutical composition should be in the range of 0.1 pg to 10 mg units per kilogram of body weight per day. If the regimen is a continuous infusion, it should also be in the range of 1 pg to 10 mg units per kilogram of body weight, respectively. Progress can be monitored by periodic assessment. Dosages will vary but a preferred dosage for intravenous administration of polyribonucleotides as constituents of the composition of the present disclosure is from approximately $10^6$ to $10^{19}$ copies of the polyribonucleotidemolecule.

In some embodiments, provided compositions are administered once daily, once a week, once every two weeks, twice a month, once a month. In some embodiments, provided compositions are administered once every 7 days, once every 10 days, once every 14 days, or once every 30 days.

The term "administered" encompasses any method suitable for introducing the composition into the body of a subject or to a system, such as cells in culture. Administration of the suitable compositions may be effected in different ways, e.g., by intravenous, intraarterial, intraperitoneal, subcutaneous, transdermal, intrathecal, intramuscular, topical, intradermal, intranasal, pulmonary, e.g., by inhalation or intrabronchial or oral or rectal administration. In some embodiments the composition is administered intravenously. In some embodiments it is administered orally. In some embodiments the composition is administered intraperitoneally. In some embodiments it is administered via pulmonary delivery. In certain embodiments, pulmonary delivery is performed by aerosolization, inhalation, nebulization or instillation, formulated as respirable particles, nebulizable lipid, or inhalable dry powder.

In the case of pulmonary delivery, a delivery as described in U.S. Patent No. 20150157565 is preferred. Intravenous administration is most preferred. The compositions of the present disclosure may in particular be administered as a gene-activated matrix such as described by Shea et al. (Shea et al. 1999, Nat Biotechnol, 17, 551-554) and in EP1 198489. In principle, the pharmaceutical compositions of the disclosure may be administered locally or systemically. Administration will preferably be parenterally, e.g., intravenously, although other ways of administration are within the scope of the disclosure. Administration directly to the target site, e.g., by catheter to a site in a blood vessel, is also conceivable. Administration can, for example, also occur by direct injection into a target site. Also within the scope of the disclosure is administration by aerosolization or nebulization or oral administration. Preparations for parenteral administration include sterile aqueous or non-aqueous solutions, suspensions, and emulsions. Examples of non-aqueous solvents are propylene glycol, polyethylene glycol, fluorocarbons, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Examples of polyribonucleotide sequences of the disclosure to be formulated and/or administered include polyribonucleotides comprising any of SEQ ID Nos: 21-27 (or 99% identical thereto). In certain embodiments, the polyribonucleotide is a modified polyribonucleotide containing a combination of unmodified and modified ribonucleotides, as described herein, for example wherein 30-45% or 30-50% or 25-50% of the uridines are analogs of uridine and 5-10% or 5-20% or 5-30% of the cytidines are analogs of cytidine. In certain embodiments, the modified polyribonucleotide contains a combination of unmodified and modified ribonucleotides, wherein 30-45% or 30-50% or 25-50% of uridines in said input mixture are analogs of uridine and 5-10% or 5-20% or 5-30% of cytidines in said input mixture are analogs of cytidine. In certain embodiments, the cytidine analog is 5-iodocytidine and the uridine analog is 5-iodouridine. Also contemplated is such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes an ornithine transcarbamylase (OTC) protein, such as an ornithine transcarbamylase (OTC) protein described herein, or a protein comprising an amino acid sequence at least 90%, 91%, 92%, 93%, 94%, 95%, 96%, 97%, 98%, 99% or 100% identical thereto (e.g., to SEQ ID NO: 3).

Vectors, Host Cells and Expression

The present disclosure provides nucleic acid molecules, including DNA molecules, which encode an ornithine transcarbamylase (OTC) protein. For each DNA (polydeoxyribonucleotide or polynucleotide) sequence listed in the present disclosure, the corresponding RNA (polyribonucleotide) sequence is contemplated and vice versa.

The sequence of the polynucleotides can be derived from, for example, any suitable nucleic acid that comprises the genetic information of a gene of interest. Examples of nucleic acids include genomic DNA, RNA, or cDNA from any mammalian, preferably human, cell comprising an ornithine transcarbamylase (OTC)-encoding gene. The polynucleotides can be derived from nucleic acids carrying mutated genes and polymorphisms. A polynucleotide of the present disclosure comprises a sequence encoding an ornithine transcarbamylase (OTC) protein. In certain embodiments, the sequence (e.g., DNA sequence and/or RNA sequence) is a codon optimized sequence, such as a codon optimized sequence to facilitate expression in a mammalian system. An example for a codon optimized sequence encoding ornithine transcarbamylase (OTC) is shown in SEQ ID NO: 4. The polynucleotide may further comprise an untranslated sequence positioned upstream (5') of the ornithine transcarbamylase (OTC) protein encoding region's start codon, an untranslated sequence positioned downstream (3') of the ornithine transcarbamylase (OTC) protein encoding region's stop codon, or both an untranslated sequence positioned upstream (5') of the ornithine transcarbamylase (OTC) protein encoding region's start codon and an untranslated sequence positioned downstream (3') of the ornithine transcarbamylase (OTC) protein encoding region's stop codon. In a certain embodiments, a polynucleotide of the present disclosure may be a modified polynucleotide.

In some embodiments the disclosure relates to a polynucleotide which encodes a polyribonucleotide of any one of SEQ ID NOs: 21 to 27. In some embodiments the disclosure relates to a polynucleotide of any one of SEQ ID NOs: 31 to 39.

In certain embodiments, the ornithine transcarbamylase (OTC) nucleic acids may be operably linked to one or more regulatory nucleotide sequences in an expression construct, such as a vector or plasmid. In certain embodiments, such constructs are DNA constructs. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used. In certain aspects, this disclosure relates to an expression vector comprising a nucleotide sequence encoding an ornithine transcarbamylase (OTC) polypeptide and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

In some embodiments the disclosure relates to a vector comprising a polynucleotide which encodes a polyribonucleotide of any one of SEQ ID NOs: 21 to 27. In some embodiments the disclosure relates to a vector comprising a polynucleotide of any one of SEQ ID NOs: 31 to 39.

This present disclosure also pertains to a host cell transfected with a recombinant gene which encodes an ornithine transcarbamylase (OTC) polypeptide of the disclosure. The host cell may be any prokaryotic or eukaryotic cell. For example, an ornithine transcarbamylase (OTC) polypeptide may be expressed in bacterial cells such as *E. coli*, insect cells (e.g., using a baculovirus expression system), yeast, or mammalian cells. Other suitable host cells are known to those skilled in the art.

In some embodiments the disclosure relates to a host cell comprising a vector comprising a polynucleotide which encodes a polyribonucleotide of any one of SEQ ID NOs: 21 to 27. In some embodiments the disclosure relates to a host cell comprising a vector comprising a polynucleotide of any one of SEQ ID NOs: 31 to 39.

The present disclosure further pertains to methods of producing an ornithine transcarbamylase (OTC) polypeptide of the disclosure. For example, a host cell transfected with an expression vector encoding an ornithine transcarbamylase (OTC) polypeptide can be cultured under appropriate conditions to allow expression of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art. The polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptides (e.g., an ornithine transcarbamylase (OTC) polypeptide).

A recombinant ornithine transcarbamylase (OTC) nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. In certain embodiments, the mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

In the present context, DNA constructs encoding an ornithine transcarbamylase (OTC) protein of the disclosure are particularly suitable for generating polyribonucleotides. For example, such vectors may be used as the basis to transcribe, in vitro, a polyribonucleotide encoding an ornithine transcarbamylase (OTC) protein. Methods for in vitro transcription are well known in the art. In certain embodiments, the polyribonucleotides are polyribonucleotides of the disclosure and comprise, for example, any of the ornithine transcarbamylase (OTC) coding sequences described herein, in the presence or absence of a 5' and/or 3'-UTR, as described herein. In certain embodiments, the polyribonucleotide is modified, as described herein.

Exemplary Methods—Treatments and Conditions

The methods, polyribonucleotides, polynucleotides, and pharmaceutical compositions of this disclosure provide numerous in vivo and in vitro methods, and may be useful to treat a condition, in particular OTC deficiency. The treatment may comprise treating a subject (e.g., a patient with a disease, in particular OTC deficiency, and/or a lab animal with a condition, in particular OTC deficiency, and/or an animal model of a condition, in particular OTC deficiency). Similarly, compositions of the disclosure, including modified polyribonucleotides, may be used in vitro or ex vivo to study OTC deficiency in cell or animal-based models. For example, cells deficient for OTC expression can be used to analyze the ability to restore OTC expression and/or activity, as well as the time period over which expression and/or activity persists. Such cells and animal models are also suitable to identify other factors involved in the pathway, whether binding partners or factors in the same biochemical pathway. In other embodiments, compositions of the disclosure, such as polyribonucleotides of the disclosure, can be used to study or track mitochondrial delivery.

Polynucleotides of the disclosure can be administered to cells or subjects, such as as DNA or as polyribonucleotide, such as mRNA. Following administration, OTC is expressed in the cells or subject. In certain embodiments, the disclosure provides methods of delivering OTC activity to cells or a subject in need thereof, such as cells or a subject having an OTC deficiency. In certain embodiments, the disclosure provides methods of delivering OTC activity to mitochondria. In certain embodiments, the disclosure provides methods of delivering OTC activity to liver. In certain embodiments, delivery may be, for example, intravenous or intraperitoneal. In other embodiments, delivery may be oral or pulmonary.

In certain embodiments, the disclosure provides methods of decreasing ammonia levels in plasma and/or urine in a subject in need thereof or in cells in culture, such as a subject having an OTC deficiency. In other embodiments, the disclosure provides methods of decreasing orotic acid levels in plasma and/or urine in a subject in need thereof or in cells in culture. In certain embodiments, the disclosure provides methods of increasing citrulline in plasma and/or urine in a subject in need thereof or in cells in culture.

In certain embodiments, ammonia levels, orotic acid levels and/or citrulline are used as biomarkers to (i) identify subjects in need of treatment and/or (ii) to evaluate efficacy of treatment using modified polyribonucleotides of the disclosure.

Examples of polyribonucleotide sequences of the disclosure for use with these methods include SEQ ID Nos: 21-27 (e.g., polyribonucleotides comprising any of SEQ ID Nos: 21-27), as well as sequence at least 90%, 91%, 92%, 93%, 94%, 95%, 96%, 97%, 98%, or 99% identical to any one or more of the foregoing. In certain embodiments, the polyribonucleotides are modified polyribonucleotides containing a combination of unmodified and modified ribonucleotides, wherein 30-45% or 30-50% or 30-40% of the uridines are analogs of uridine and 5-10% or 5-20% or 5-30% of the cytidines are analogs of cytidine. In certain embodiments, the modified polyribonucleotide contains a combination of unmodified and modified ribonucleotides, wherein 30-45% or 30-50% or 30-40% of uridines in said input mixture are analogs of uridine and 5-10% or 5-20% or 5-30% of cytidines in said input mixture are analogs of cytidine. In certain embodiments, the cytidine analog is 5-iodocytidine and the uridine analog is 5-iodouridine. Also contemplated is such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes an ornithine transcarbamylase (OTC) protein, such as an ornithine transcarbamylase (OTC) protein described herein, or a protein comprising an amino acid sequence at least 90%, 91%, 92%, 93%, 94%, 95%, 96%, 97%, 98%, 99% or 100% identical thereto.

EXEMPLIFICATION

The disclosure now being generally described, it will be more readily understood by reference to the following examples, which are included merely for purposes of illustrating certain embodiments of the present disclosure. These examples are not intended to limit the disclosure.

Example 1

Ornithine Transcarbamylase (OTC) Polynucleotide and Polyribonucleotide Construction Preparation of DNA Constructs Several constructs for transcribing mRNA encoding human OTC have been prepared which contain a T7 promoter, a 5' UTR, a coding sequence for human OTC (natural or codon-optimized) and in some cases a 3' UTR. The sequences of these constructs reflecting the promoter region, the UTRs and the coding region are given in SEQ ID NOs: 31 to 39 and the names of these DNA constructs together with their characteristics as regards the promoter, the UTR(s) and the coding region are listed in Table 9.

TABLE 9

| Construct Name | 5' UTR | 3' UTR | Promoter | Codon optimized |
|---|---|---|---|---|
| T7-hOTCcDNA (with natural UTRs at 5' and 3' end) (SEQ ID NO: 31) | Natural UTR from human OTC | Natural UTR from human OTC | T7 | No |
| T7-hOTC (SEQ ID NO: 32) | Minimal UTR | — | T7 | No |
| T7-5'hAg-hOTC (SEQ ID NO: 33) | human α-globin UTR | — | T7 | No |
| T7-5'ETH-hOTC-3'ETH (SEQ ID NO: 34) | CYBA | CYBA | T7 | No |
| T7-hOTCcDNA(CO) (SEQ ID NO: 35) | Natural UTR from human OTC | Natural UTR from human OTC | T7 | Yes |
| T7-hOTC(CO) (SEQ ID NO: 36) | Minimal UTR | — | T7 | Yes |
| T7-5'hAg-hOTC(CO) (SEQ ID NO: 37) | human α-globin UTR | — | T7 | Yes |
| T7-5'ETH-hOTC(CO)-3'ETH (SEQ ID NO: 38) | CYBA | CYBA | T7 | Yes |
| T7-TISU-hOTC(CO) (SEQ ID NO: 39) | TISU + T | — | T7 | Yes |

The following sequence (SEQ ID NO: 40) corresponds to the Minimal 5' UTR; specifically the DNA sequence of the 5' UTR used in the constructs noted above as Minimal. The depicted sequence corresponds to one strand of the double stranded nucleic acid.

```
(SEQ ID NO: 40)
1 GGGAGACGCC ACC
```

The following sequence (SEQ ID NO: 41) corresponds to a hAg 5' UTR; specifically the DNA sequence of a 5' UTR derived from human alpha globin and used in the 5' UTR of the constructs noted above as hAg. The depicted sequence corresponds to one strand of the double stranded nucleic acid.

```
(SEQ ID NO: 41)
1 GGGAGACTCT TCTGGTCCCC ACAGACTCAG AGAGAACGCC ACC
```

The following sequence (SEQ ID NO: 43) corresponds to the TISU+T 5' UTR; specifically the DNA sequence of the 5' UTR used in the constructs noted above. The depicted sequence corresponds to one strand of the double-stranded nucleic acid (SEQ ID NO: 43)
1 GGGAGACTGC CAAG The following sequence (SEQ ID NO: 47) corresponds to the CYBA 5' UTR; specifically the DNA sequence of the 5' UTR used in the constructs noted above. The depicted sequence corresponds to one strand of the double-stranded nucleic acid (SEQ ID NO: 47)
GGGAGACCGC GCCTAGCAGT GTCCCAGCCG GGTTCGTGTC

GCCGCCACC

Codon Optimization of hOTC Sequence and its Use in Constructs

The coding region (ORF) of OTC was codon optimized for expression in humans and for use in the context of modified polyribonucleotides. The resulting optimized sequence was combined with regulatory elements (Kozak/TISU, UTR(s)), T7 Promoter and flanking cloning sites. The sequence set forth in SEQ ID NO: 4 worked surprisingly well and outperformed numerous sequences in the context of our modified polyribonucleotides and UTRs.

Design of Stop Sequence

As described below, a codon optimized construct with human alpha globin UTR at the 5' end was identified as the lead construct in expression studies. Therefore, STOP RNA (resulting in no detectable translation) was designed only for this UTR containing construct. For this, the Kozak element was scrambled from GCCACC to CGCCCG and the start ATG was mutated to TGA. Moreover, to rule out any translation initiation from downstream ATGs, thereby resulting in truncated protein products, all downstream in-frame ATG were also mutated to TGA. The resulting sequence contained in the DNA construct for expressing a corresponding polyribonucleotide is shown in SEQ ID NO: 44 (only the promoter, the 5' UTR, and the coding region including the stop codon; the mutated start codon is indicated in bold; the natural stop codon is indicated in italics; the artificially introduced stop codons are indicated by underlining). Cloning sites were kept identical to the test sequence to rule out positional effects.

Example 2

Cloning of Templates and Production of the SNIM® RNA

To generate the respective template for in vitro transcription, the cloning vector pETH1 was cut with restriction enzymes NheI and AfeI. For cloning of human OTC sequences into pETH1 5' (NheI) and 3' (AfeI) cloning sites were added to the human OTC sequences and cloned into the respective sites of the cloning vector pETH1 (which also allows for polyadenylation if desired) to achieve T7-hOTCcDNA (Table 9, SEQ ID NO: 31), T7-hOTCcDNA (CO) (Table 9, SEQ ID NO: 35), T7-hOTC (Table 9, SEQ ID NO: 32), T7-hOTC(CO) (Table 9, SEQ ID NO: 36), T7-5'ETH-hOTC-3'ETH (Table 9, SEQ ID NO: 34), T7-5'ETH-hOTC(CO)-3'ETH (Table 9, SEQ ID NO: 38), T7-5'hAg-hOTC (Table 9, SEQ ID NO: 33), and T7-5'hAg-hOTC(CO) (Table 9, SEQ ID NO: 37). Cloning of mouse OTC sequence (SEQ ID NO: 45) into pETH1 was performed through the addition of 5' (HindIII) and 3' (BstBI) cloning sites to the murine OTC sequence (SEQ ID NO: 45). The correct clones were sequence confirmed.

The respective template for in vitro transcription was linearized by restriction digestion with AfeI (New England BioLabs). Template was further purified by chloroform ethanol precipitation. Uncapped, non polyadenylated mRNA was produced using a standard in vitro transcription mix containing T7 RNA polymerase (Thermo Fisher Scientific). For in vitro transcription to generate modified polyribonucleotides, cytidine-5'-triphosphate was replaced by 5-methylcytidine-5'-triphosphate, 2'-fluoro-2'-deoxycytidine-5'-triphosphate or 5-iodocytidine-5'-triphosphate and uridine-5'-triphosphate was replaced by 2-thiouridine-5'-triphosphate or 5-iodouridine-5'-triphosphate (Jena Biosciences) as indicated in the description of the respective example. Subsequently mRNA was purified by ammonium acetate precipitation and ultrafiltration using a 100 MWCO cut of filter (Sartorius).

Capping of uncapped, non polyadenylated mRNA was carried out using Vaccinia virus capping enzyme and a mRNA cap 2-o-methyltransferase (New England BioLabs) resulting in a cap 1 structure followed by purification via ammonium acetate precipitation. Non polyadenylated mRNA was further polyadenylated by using a poly(A) polymerase (New England BioLabs). Again mRNA was purified by ammonium acetate precipitation. Poly(A) length was determined by capillary gel electrophoresis to be ~200 nucleotides.

Example 3

Lack of Urea Production by HepG2 Cells is Due to Defective Ornithine Transcarbamylase (OTC) and Arginase I (ArgI) Expression Mavri-Damelin et al. (Int. J. Biochem Cell Biol. 39 (2007), 555-564) have investigated the functional deficiency of HepG2 cells (ATCC HB-8065) in urea production. They have demonstrated that the lack of urea production by HepG2 cells is due to defective Ornithine Transcarbamylase (OTC) and Arginase I (ArgI) expression, while other urea cycle enzymes like Carbamoyl Phosphate Synthase I (CPSI), Arginosuccinate Synthetase (AS) and Arginosuccinate Lyase (AL), were expressed at levels comparable to cultured primary human hepatocytes (Mavri-Damelin, 2007). As OTC catalyzes the reaction between carbamoyl phosphate (CP) and ornithine (Orn) to form citrulline (Cit) and phosphate (Pi), HepG2 cells are also incapable of producing citrulline. Thus, the HepG2 cell line is a suitable tool to investigate OTC deficiency in vitro and was used as a model system to investigate whether or not it is possible to restore urea cycle function by transient expression of OTC in these cells (FIG. 1).

Figure 3A:
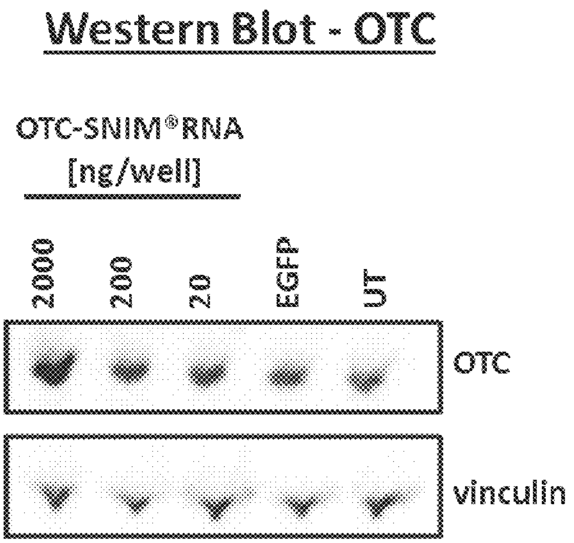
FIG. 3(A) shows a Western blot of OTC after transient transfection of primary human hepatocytes with OTC encoding a modified polyribonucleotide of the disclosure (e.g., in this example, modified polyribonucleotide sometimes referred to as a SNIM®-RNA); UT=not transfected. The OTC encoding modified polyribonucleotide was generated through in vitro transcription in the presence 25% 2-thiouridine-5'-triphosphate and 25% 5-methylcytidine-5'-triphosphate of Construct T7-5'hAg-hOTC(CO) (Table 9, SEQ ID NO: 37). In other words, 25% of the uridine in the in vitro transcription reaction was the analog 2-thiouridine and 25% of the cytidine in the in vitro transcription reaction was the analog 5-methylcytidine.

In contrast to HepG2 cells, primary human hepatocytes have high endogenous levels of OTC (FIGS. 3(A) and (B)). FIGS. 3(A) and (B) also show that, despite the high endogenous level of OTC in primary human hepatocytes, the level of enzymatically active enzyme can still be increased in a dose dependent manner by transfection of these cells with SNIM® RNA (e.g., modified polyribonucleotides of the disclosure) encoding OTC.

Figure 1:
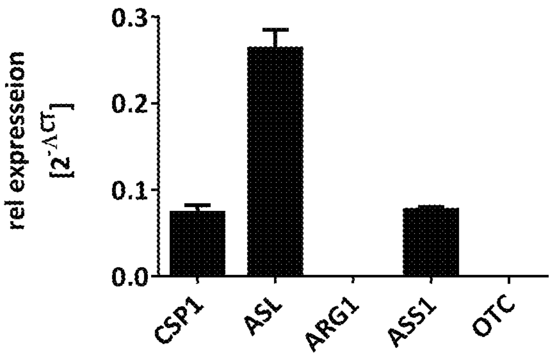
FIG. 1 shows that the lack of urea production by HepG2 cells is due to defective Ornithine Transcarbamylase (OTC) and Arginase I (ArgI) expression.

The data shown in FIG. 1 confirms prior experiments demonstrating that OTC and arginase are not expressed in HepG2 cells. For the production of the data shown in FIG. 1, RNA from HepG2 cells (ACC 180, DSMZ, Germany) was isolated using NucleoSpin® RNA Kit (cat #740955.250, Machery-Nagel, Germany). cDNA was synthesized from 1 μg total RNA using First strand cDNA Synthesis Kit (cat. #K1612, Fermentas/Thermo Scientific, Germany). qPCR was performed with SsoAdvanced Universal SYBR Green Supermix (cat #172-5271, Bio-Rad, Germany) on a LC96 Instrument (Roche Life Sciences, Germany). The following primer pairs were used:

TABLE 10

| Target gene | | NM_no | Primer name | Primer forward | Primer reverse |
|---|---|---|---|---|---|
| Carbamoyl-phosphate synthase | CSP1 | NM_001875.4 | huCSP1 | caagttttgcagtggaatcg | actgggtagccaatggtgtc |
| agininosuccinate lyase | ASL | NM_000048.3 | huASL | acatggcctcggagagt | atggacgcgttgaacttctc |
| arginase | ARG1 | NM_000045.3 | huARG1 | cctcctgaaggaactaaaaggaa | ccttggcagatatacagggagt |
| argininosuccinate synthase 1 | Ass1 | NM_054012.3 | huASS1 | cctgtgcttataacctgggatg | gagcctttgctggacatagc |
| ornitine carbamoyltransferase | OTC | NM_00531.5 | huOTC | ccagatcctggctgattacc | ccagctgagggtaagacctt |

Reference gene primer were purchased from Bio-Rad, Germany:
Beta-Actin: PrimePCR ™ SYBRO ® Green Assay: ACTB, Human TATA-box binding protein: PrimePCR ™ SYBRO ® Green Assay: TBP, Human
Results were calculated applying the ΔCT method. Pfaffl, M.W.(2001): *A new mathematical model for relative quantification in real-time* RT-PCR. *Nucleic Acids Res.*, 29(9): e45

Example 4

Figure 2A:
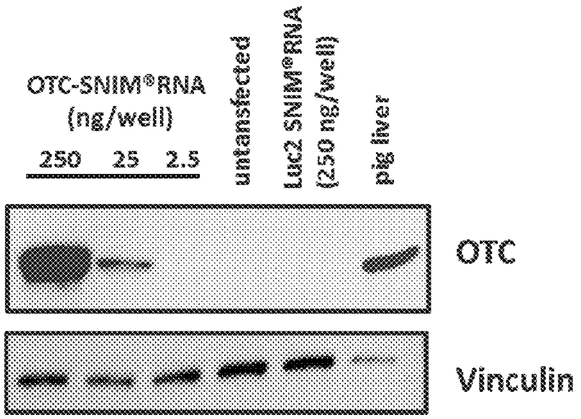
FIG. 2(A) shows exogenous expression of OTC protein by a modified polyribonucleotide of the disclosure (e.g., in this example, a modified polyribonucleotides sometimes referred to as a SNIM® RNA) in HepG2 cells. SNIM® RNA was generated by in vitro transcription of Construct T7-5'hAg-hOTC(CO) (Table 9, SEQ ID NO: 37) in the presence of 25% 2-thiouridine-5'-triphosphate and 25% 5-methylcytidine-5'-triphosphate. In other words, 25% of the uridine in the in vitro transcription reaction was the analog 2-thiouridine and 25% of the cytidine in the in vitro transcription reaction was the analog 5-methylcytidine.

Transfection with OTC-SNIM® RNA Leads to OTC Protein and Activity in HepG2 Cells FIG. 2(A) shows the exogenous expression of OTC protein by modified polyribonucleotides of the disclosure in HepG2 cells.

OTC-protein was detected by Western blot. $7.5\times10^4$ HepG2 cells (ACC 180, DSMZ, Germany) per well were seeded in 24 well plates. 24 h after seeding cells were transfected with 250 or 25 ng/well OTC-or Luc2-SNIM® RNA (control) containing 25% 2-thiouridine-5'-triphosphate and 25% 5-methylcytidine-5'-triphosphate using EffectA (Ethris internal transfection reagent). OTC modified polyribonucleotide was generated by in vitro transcription of Construct T7-5'hAg-hOTC(CO) (Table 9, SEQ ID NO: 37). 24 h after transfection, cells were lysed. 15 μg of total cell lysate were separated per lane on a 10% by SDS-PAGE 10% Mini-PROTEAN® TGX™ Precast Protein Gels (cat #4561034, Bio-Rad, Germany) and blotted on a PVDF membrane using Trans-Blot Turbo Transfer Pack, Mini, PVDF, 7×8.5 cm (cat #B170-4156, Bio-Rad, Germany) and a Trans-Blot Turbo instrument (cat. ##1704155SP1, Bio-Rad, Germany) Membranes were blocked in NET-gelatin buffer (50 mM Tris [pH 7.5], 150 mM NaCl, 0.05% Triton™ X-100, 5 mM EDTA and 0.25% gelatin (sigma-aldrich, Germany) Signals were analyzed on a Gel Doc™ XR+ System, Bio-Rad, Germany) Representative images are shown.

Used Antibodies:

Rabbit anti-OTC, cat #AP6928c, ABGENT (BioCat), USA, Dilution 1:2000

Rabbit anti-Vinculin, cat #ab91459, abcam, UK, Dilution 1:5000

Goat anti-rabbit IgG-HRP, cat #2004, SCBT, USA, Dilution 1:10000

Example 5

Figure 2B:
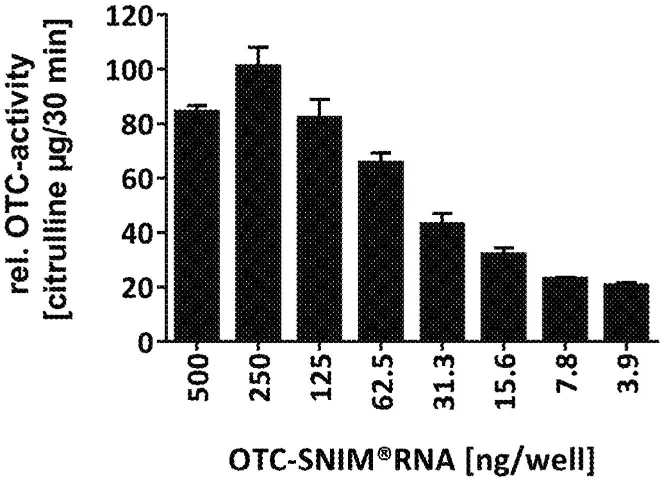
FIG. 2(B) shows OTC activity after exogenous expression of OTC protein by a modified polyribonucleotide of the disclosure (e.g., in this example, a modified polyribonucleotide sometimes referred to as a SNIM® RNA) in HepG2 cells. OTC SNIM® RNA was generated by in vitro transcription in the presence of 35% 5-iodouridine-5'-triphosphate and 7.5% 5-iodocytidine-5'-triphosphate of Construct T7-5'hAg-hOTC(CO) (Table 9, SEQ ID NO: 37). In other words, 35% of the uridine in the in vitro transcription reaction was the analog 5-iodouridine and 7.5% of the cytidine in the in vitro transcription reaction was the analog 5-iodocytidine.

OTC Activity After Exogenous Expression of OTC Protein by Modified Polyribonucleotides of the Disclosure (e.g., SNIM® RNA) in HepG2 Cells FIG. 2(B) shows the OTC activity in HepG2 cells after exogenous expression of OTC protein. OTC modified polyribonucleotides were generated by in vitro transcription in the presence of 35% 5-iodouridine-5'-triphosphate and 7.5% 5-iodocytidine-5'-triphosphate of Construct T7-5'hAg-hOTC(CO) (Table 9, SEQ ID NO: 37). OTC-activity was detected by OTC activity assay. $5\times10^4$ HepG2 cells were seeded in 96-well plates. 24 h after seeding cells were transfected with OTC-SNIM® RNA using Lipofectamine2000 (cat #11668027, Thermo-Fisher Scientific, Germany). 24 h after transfection OTC-activity assay was performed. Protocol adapted from Ye et al., 1996 (YE, X., ROBINSON, M, BATSHAW, M., FURTH, E., SMITH, I., and WILSON, J. (1996). *Prolonged metabolic correction in adult ornithine transcarbamylase deficiency mice with adenoviral vectors. J. Biol. Chem.* 271, 3639-3646). Plates were thawed at 37° C. (app. 15 min). Citrulline-standards (cat #C7629, sigma-aldrich, Germany) controls were added to the wells. The substrates ornithine (cat #02375 sigma-aldrich, Germany) and carbamoylphosphate (Lithium carbamoylphosphate dibasic hydrate, cat #C5625, sigma-aldrich, Germany, prepared freshly from dry powder stored at −20° C.) were added. Plates were incubated at 37° C. for 30 min. During that time OTC converted ornithine and carbamoylphosphate to citrulline and ortho-phosphate. To stop the enzymatic reaction, a mix of phosphoric acid and sulphuric acid (sigma-aldrich, Germany) was added. Thus, the pH was lowered and the detection reaction was started. For the detection of citrulline, diacetylmonooxim (2,3-Butanedione monoxime, B0753, sigma-aldrich, Germany) was added and the plates were heated up to 70° C. for 15 min. In a reaction called Fearon-reaction citrulline was converted to a yellow product (Abs 490 nm). The absorbance was measured using a Tecan Infinite F200 Pro plate reader (Tecan, Austria). Absolute citrulline values were determined by a standard curve. Mean+/−SEM of three experimental replicates was calculated.

TABLE 11

Reagents used for OTC-activity assay

| volume added to well [μL] | substance | molar weight [g/Mol] | concentration in assay mM | concentration in buffer | solution in |
|---|---|---|---|---|---|
| Lysis Buffer pH 7.7 | | | | | |
| 70 | Triethanolamine | 149 | 250 | 250 mM | $H_2O$ |
| | Triton X-100 | | | 0.1 % | |
| Assay Buffer 7.7 | | | | | |
| 20 | L-Ornithine monohydrochloride | 169 | 5 | 25 mM | $H_2O$ |
| | Triethanolamine | 149 | 250 | 1250 mM | |

TABLE 11-continued

| Reagents used for OTC-activity assay | | | | | |
|---|---|---|---|---|---|
| volume added to well [μL] | substance | molar weight [g/Mol] | concen-tration in assay mM | concen-tration in buffer | solution in |
| CaP-Buffer | | | | | |
| 10 | Lithium carbamoylphosphate dibasic hydrate | 153 | 15 | 150 mM | $H_2O$ |
| Developing Buffer | | | | | |
| 10 | 2,3-Butanedione monoxime | 101 | | 3% | in Methanol |
| Stop Solution | | | | | |
| 50 | phosphoric acid sulfuric acid | | | 3 to 1 1 to 3 | |

Example 6

Primary Human Hepatocytes have High Endogenous Level of OTC

FIGS. 3(A) and (B) show that primary human hepatocytes have high endogenous level of OTC. FIG. 3(A) shows a Western blot of OTC after transient transfection of primary human hepatocytes with OTC encoding modified polyribonucleotides of the disclosure (e.g., SNIM®-RNAs) generated through in vitro transcription in the presence 25% 2-thiouridine-5'-triphosphate and 25% 5-methylcytidine-5'-triphosphate of Construct T7-5'hAg-hOTC(CO) (Table 9, SEQ ID NO: 37). UT=not transfected. OTC-protein in primary human hepatocytes was detected by Western blot. Cultures of primary human hepatocytes in 96-well plates were purchased from Lonza (cat #CC-2698A Lonza, Swiss) 24 h after arrival, cells were transfected with 2000, 200 or 20 ng/well OTC-or EGFP-encoding modified polyribonucleotides (e.g., SNIM® RNA) (EGFP=control) using Lipofectamine2000 (cat #11668027, Thermo-Fisher Scientific, Germany). 24 h after transfection cells were lysed. Total cell lysates were separated by SDS-PAGE 10% Mini-PROTEAN® TGX™ Precast Protein Gels, 15-well (cat #4561036, Bio-Rad, Germany) and blotted on a PVDF membrane using Trans-Blot Turbo Transfer Pack, Mini, PVDF, 7×8.5 cm (cat #B170-4156, Bio-Rad, Germany) and a Trans-Blot Turbo instrument (cat. ##1704155SP1, Bio-Rad, Germany). Membranes were blocked in NET-gelatin buffer (50 mM Tris [pH 7.5], 150 mM NaCl, 0.05% Triton™ X-100, 5 mM EDTA and 0.25% gelatin (sigma-aldrich, Germany) for 30 min before the membranes were incubated overnight at 4° C. with the primary antibody, diluted in NET-gelatin. After three washes with NET-gelatin, horseradish peroxidase-conjugated secondary antibody was added for 1 h at RT. The membrane was washed again three times with NET-gelatin until signals were visualized with a chemiluminescent substrate kit (Luminata Crescendo Western HRP substrate, cat #WBLUR0100 Merck Millipore, Germany) and recorded using the ChemiDoc™ MP System, Bio-Rad, Germany. Representative images are shown.

Used Antibodies:

Rabbit anti-OTC, cat #AP6928c, ABGENT (BioCat), USA, Dilution 1:2000

Rabbit anti-Vinculin, cat #ab91459, abcam, UK, Dilution 1:5000

Goat anti-rabbit IgG-HRP, cat #2004, SCBT, USA, Dilution 1:10000

Example 7

Figure 3B:
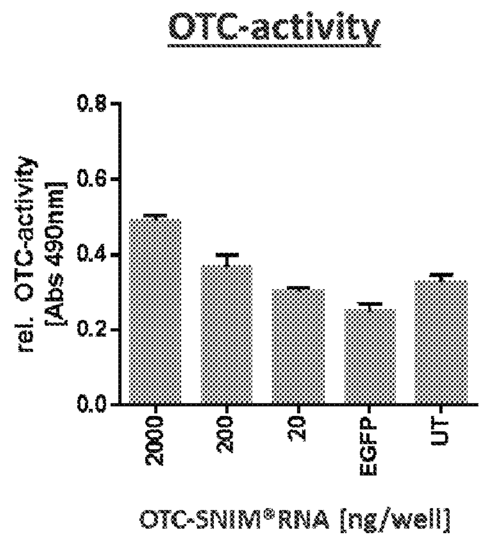
FIG. 3(B) shows the enzymatic activity of OTC after transient transfection of primary human hepatocytes with an OTC encoding modified polyribonucleotide of the disclosure (e.g., SNIM®-RNA). OTC encoding SNIM®-RNA was generated through in vitro transcription in the presence of 25% 2-thiouridine-5'-triphosphate and 25% 5-methylcytidine-5'-triphosphate of Construct T7-5'hAg-hOTC(CO) (Table 9, SEQ ID NO: 37). In other words, 25% of the uridine in the in vitro transcription reaction was the analog 2-thiouridine and 25% of the cytidine in the in vitro transcription reaction was the analog 5-methylcytidine.

Enzymatic Activity of OTC After Transient Transfection of Primary Human Hepatocytes with OTC Encoding SNIM®-RNA FIG. 3(B) shows the enzymatic activity of OTC after transient transfection of primary human hepatocytes with OTC encoding modified polyribonucleotides (e.g., SNIM®-RNAs) generated through in vitro transcription in the presence of 25% 2-thiouridine-5'-triphosphate and 25% 5-methylcytidine-5'-triphosphate of Construct T7-5'hAg-hOTC (CO) (Table 9, SEQ ID NO: 37).

OTC-activity in primary human hepatocytes was detected by OTC-activity assay. Cultures of primary human hepatocytes in 96-well plates were purchased from Lonza (cat #CC-2698A Lonza, Swiss). 24 h after arrival cells were transfected with 2000, 200 or 20 ng/well OTC-or EGFP encoding modified polyribonucleotides (e.g., SNIM® RNA (EGFP=control)) using Lipofectamine2000 (cat #11668027, Thermo-Fisher Scientific, Germany). 24 h after transfection cells were lysed, frozen and OTC-activity assay was performed. Protocol adapted from Ye et al., 1996 (YE, X., ROBINSON, M., BATSHAW, M., FURTH, E., SMITH, I., and WILSON, J. (1996). *Prolonged metabolic correction in adult ornithine transcarbamylase deficiency mice with adenoviral vectors. J. Biol. Chem.* 271, 3639-3646). Plates were thawed at 37° C. (app. 15 min). The substrates ornithine (cat #02375 sigma-aldrich, Germany) and carbamoylphosphate (Lithium carbamoylphosphate dibasic hydrate, cat #C5625, sigma-aldrich, Germany, prepared freshly from dry powder stored at −20° C.) were added. Plates were incubated at 37° C. for 30 min. During that time OTC converted ornithine and carbamoylphosphate to citrulline and ortho-phosphate. To stop the enzymatic reaction, a mix of phosphoric acid and sulphuric acid (sigma-aldrich, Germany) was added. Thus, the pH was lowered and the detection reaction was started. For the detection of citrulline, diacetylmonooxim (2,3-Butanedione monoxime, B0753, sigma-aldrich, Germany) was added and the plates were heated up to 70° C. for 15 min. In a reaction called Fearon-reaction citrulline was converted to a yellow product (Abs 490 nm). The absorbance was measured using a Tecan Infinite F200 Pro plate reader (Tecan, Austria). Mean+/−SEM of three experimental replicates was calculated.

Example 8

Expression of OTC Protein by SNIM® RNA in HepG2 Cells

Figure 4A:
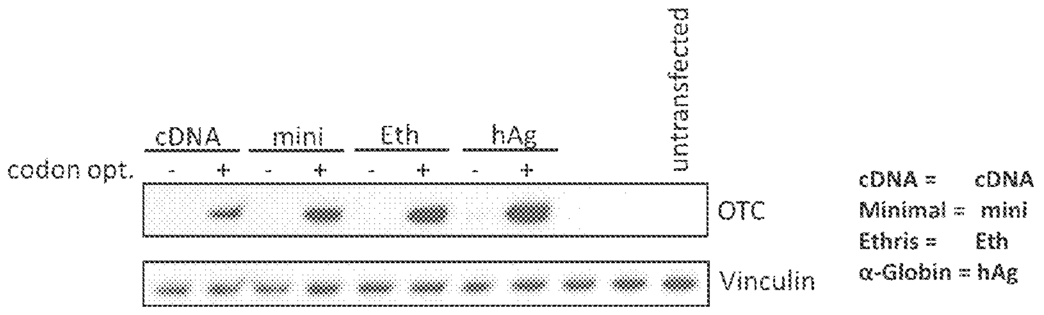
FIG. 4(A) shows that modified polyribonucleotides (+) with a particular codon optimized coding sequence shows higher translation than the respective wild type sequence (not codon optimized (−)), independently from the UTR that has been employed. Modified polyribonucleotides encoding OTC were generated through in vitro transcription in the presence of 50% 5-iodouridine-5'-triphosphate and 30% 2'-fluoro-2'-deoxycytidine-5'-triphosphate of Constructs T7-hOTCcDNA (Table 9, SEQ ID NO: 31), T7-hOTCcDNA (CO) (Table 9, SEQ ID NO: 35), T7-hOTC (Table 9, SEQ ID NO: 32), T7-hOTC(CO) (Table 9, SEQ ID NO: 36), T7-5'ETH-hOTC-3'ETH (Table 9, SEQ ID NO: 34), T7-5'ETH-hOTC(CO)-3'ETH (Table 9, SEQ ID NO: 38), T7-5'hAg-hOTC (Table 9, SEQ ID NO: 33), and T7-5'hAg-hOTC(CO) (Table 9, SEQ ID NO: 37) respectively.

FIG. 4(A) shows that modified polyribonucleotides (e.g., SNIM® RNA) (+) with codon optimized coding sequence shows higher translation than the respective wild type sequence (not codon optimized (−)), independently from the UTR that has been employed. Modified polyribonucleotides were generated through in vitro transcription in the presence of 50% 5-iodouridine-5'-triphosphate and 30% 2'-fluoro-2'-deoxycytidine-5'-triphosphate of Constructs T7-hOTCcDNA (Table 9, SEQ ID NO: 31), T7-hOTCcDNA (CO) (Table 9, SEQ ID NO: 35), T7-hOTC (Table 9, SEQ ID NO: 32), T7-hOTC(CO) (Table 9, SEQ ID NO: 36), T7-5'ETH-hOTC-3'ETH (Table 9, SEQ ID NO: 34), T7-5'ETH-hOTC(CO)-3'ETH (Table 9, SEQ ID NO: 38), T7-5'hAg-hOTC (Table 9, SEQ ID NO: 33), and T7-5'hAg-hOTC(CO) (Table 9, SEQ ID NO: 37), respectively.

OTC-protein was detected by Western blot. $5\times10^4$ HepG2 cells (ACC 180, DSMZ, Germany) per well were seeded in 96-well plates. 24 h after seeding cells were transfected with 150 ng/well OTC encoding polyribonucleotides using Lipofectamine2000 (cat #11668027, Thermo-Fisher Scientific, Germany). 24 h after transfection cells were lysed using lysis buffer (25 mM TRIS, 0.1% Triton-X 100) complemented with protease inhibitor (cOmplete, EDTA-free, cat #11873580001, Roche, Germany) and DNase (DNase I Solution (2500 U/mL), cat #90083, Thermo Fisher Scientific, Germany). After lysis the samples were mixed with NuPAGE® LDS Sample Buffer (NP0007) and NuPAGE® Sample Reducing Agent (10×) (NP0004) and heated for 10 min at 70° C. Gel electrophoresis was performed using 15 μL of the lysate on NuPAGE 10% Bis-Tris Midi Gels (WG1203BOX) with the XCell4 SureLock™ Midi Cell, Thermo-Fisher Scientific, Germany. The gels were blotted on a PVDF membrane using Trans-Blot Turbo Transfer Pack, Midi, PVDF, 7×8.5 cm (cat #1704157, Bio-Rad, Germany) and a Trans-Blot Turbo instrument (cat #1704155SP1, Bio-Rad, Germany). Membranes were blocked in NET-gelatin buffer (50 mM Tris [pH 7.5], 150 mM NaCl, 0.05% Triton™ X-100, 5 mM EDTA and 0.25% gelatin (sigma-aldrich, Germany) for 30 min before the membranes were incubated overnight at 4° C. with the primary antibody, diluted in NET-gelatin. After three washes with NET-gelatin, horseradish peroxidase-conjugated secondary antibody was added for 1 h at RT. The membrane was washed again three times with NET-gelatin until signals were visualized with a chemiluminescent substrate kit (Luminata Crescendo Western HRP substrate, cat #WBLUR0100 Merck Millipore, Germany) and recorded using the ChemiDoc™ MP System, Bio-Rad, Germany.

Rabbit anti-OTC, cat #AP6928c, ABGENT (BioCat), USA, Dilution 1:2000

Rabbit anti-Vinculin, cat #ab91459, abcam, UK, Dilution 1:5000

Goat anti-rabbit IgG-HRP, cat #2004, SCBT, USA, Dilution 1:10000

Example 9

Figure 4B:
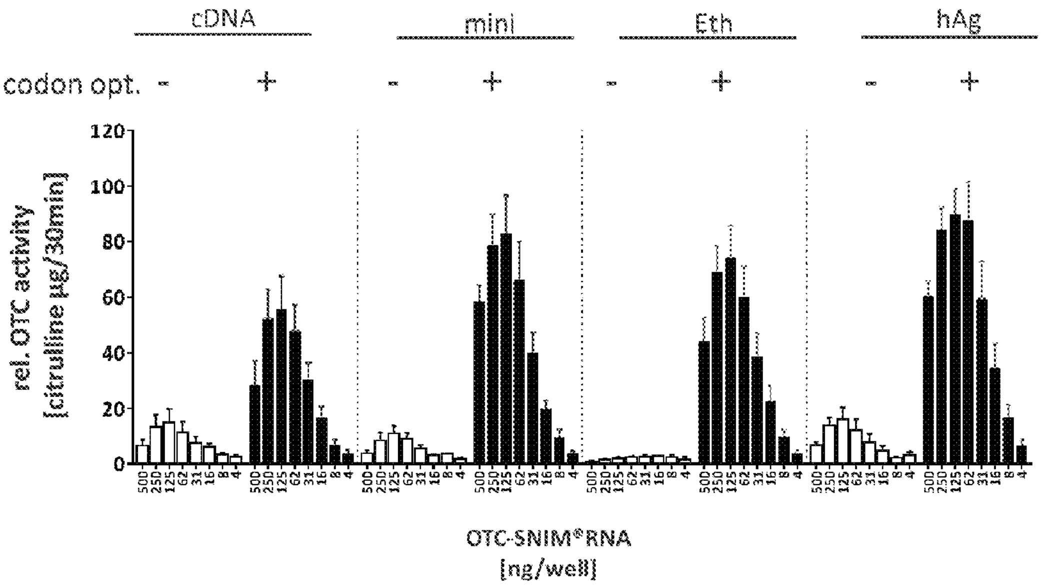
FIG. 4(B) shows OTC activity after transfection of HepG2 cells with modified polyribonucleotides encoding OTC. cDNA=cDNA; Minimal=mini, Ethris=Eth (=CYBA), α-Globin=hAg.

OTC Activity After Transfection with OTC-SNIM® RNA in HepG2 Cells cDNA=cDNA; Minimal=mini, Ethris=Eth (CYBA), α-Globin=hAg FIG. 4(B) shows OTC activity after transfection with OTC encoding modified polyribonucleotides (e.g., SNIM® RNA) in HepG2 cells. cDNA=cDNA; Minimal=mini, Ethris=Eth (CYBA), α-Globin=hAg. Modified polyribonucleotides were generated through in vitro transcription in the presence of 50% 5-iodouridine-5'-triphosphate and 30% 2'-fluoro-2'-deoxycytidine-5'-triphosphate of Constructs T7-hOTCcDNA (Table 9, SEQ ID NO: 31), T7-hOTCcDNA (CO) (Table 9, SEQ ID NO: 35), T7-hOTC (Table 9, SEQ ID NO: 32), T7-hOTC(CO) (Table 9, SEQ ID NO: 36), T7-5'ETH-hOTC-3'ETH (Table 9, SEQ ID NO: 34), T7-5'ETH-hOTC(CO)-3'ETH (Table 9, SEQ ID NO: 38), T7-5'hAg-hOTC (Table 9, SEQ ID NO: 33), and T7-5'hAg-hOTC(CO) (Table 9, SEQ ID NO: 37) respectively.

OTC-activity in HepG2 cells (ACC 180, DSMZ, Germany) was detected by OTC-activity assay. $5\times10^4$ HepG2 cells were seeded per well in 96-well plates. 24 h after seeding cells were transfected with 500-4 ng/well OTC encoding modified polyribonucleotide with different UTRs transcribed from the constructs indicated above using Lipofectamine2000 (cat #11668027, Thermo-Fisher Scientific, Germany). 24 h after transfection cells were lysed, frozen OTC-activity assay was performed. Protocol adapted from Ye et al., 1996 (YE, X., ROBINSON, M., BATSHAW, M., FURTH, E., SMITH, I., and WILSON, J. (1996). *Prolonged metabolic correction in adult ornithine transcarbamylase deficiency mice with adenoviral vectors. J. Biol. Chem.* 271, 3639-3646). Plates were thawed at 37° C. (app. 15 min). Citrulline-standards (cat #C7629, sigma-aldrich, Germany) controls were added to the wells. The substrates ornithine (cat #02375 sigma-aldrich, Germany) and carbamoylphosphate (Lithium carbamoylphosphate dibasic hydrate, cat #C5625, sigma-aldrich, Germany, prepared freshly from dry powder stored at −20° C.) were added. Plates were incubated at 37° C. for 30 min. During that time OTC converted ornithine and carbamoylphosphate to citrulline and orthophosphate. To stop the enzymatic reaction, a mix of phosphoric acid and sulphuric acid (sigma-aldrich, Germany) was added. Thus, the pH was lowered and the detection reaction was started. For the detection of citrulline, diacetylmonooxim (2,3-Butanedione monoxime, B0753, sigma-aldrich, Germany) was added and the plates were heated up to 70° C. for 15 min. In a reaction called Fearon-reaction citrulline was converted to a yellow product (Abs 490 nm). The absorbance was measured using a Tecan Infinite F200 Pro plate reader (Tecan, Austria). Absolute citrulline values were determined by a standard curve. Mean+/−SEM of three independent experiments was calculated.

Example 10

OTC Activity After Transfection with OTC-SNIM® RNA in HepG2 Cells

FIG. 5(A) shows OTC activity after transfection with modified polyribonucleotides (e.g., OTC-SNIM® RNA) in HepG2 cells. co=codon optimized; cDNA=cDNA; Minimal=mini, Ethris=Eth (CYBA), α-Globin=hAg. Modified polyribonucleotides (e.g., SNIM®-RNA) was generated through in vitro transcription in the presence of 50% 5-iodouridine-5'-triphosphate and 30% 2'-fluoro-2'-deoxyfluoro-2'-deoxycytidine-5'-triphosphate of Constructs T7-hOTCcDNA (Table 9, SEQ ID NO: 31), T7-hOTCcDNA (CO) (Table 9, SEQ ID NO: 35), T7-hOTC (Table 9, SEQ ID NO: 32), T7-hOTC(CO) (Table 9, SEQ ID NO: 36), T7-5'ETH-hOTC-3'ETH (Table 9, SEQ ID NO: 34), T7-5'ETH-hOTC(CO)-3'ETH (Table 9, SEQ ID NO: 38), T7-5'hAg-hOTC (Table 9, SEQ ID NO: 33), and T7-5'hAg-hOTC(CO) (Table 9, SEQ ID NO: 37) respectively.

FIG. 5(B) shows OTC activity after transfection with OTC encoding modified polyribonucleotides (e.g., OTC-SNIM® RNA) in HepG2 cells. co=codon optimized; cDNA=cDNA; Minimal=mini, Ethris=Eth (CYBA), α-Globin=hAg. Modified polyribonucleotides were generated through in vitro transcription in the presence of 50% 5-iodouridine-5'-triphosphate and 30% 2'-fluoro-2'-deoxycytidine-5'-triphosphate of Constructs T7-hOTCcDNA (Table 9, SEQ ID NO: 31), T7-hOTCcDNA(CO) (Table 9, SEQ ID NO: 35), T7-hOTC (Table 9, SEQ ID NO: 32), T7-hOTC(CO) (Table 9, SEQ ID NO: 36), T7-5'ETH-hOTC-3'ETH (Table 9, SEQ ID NO: 34), T7-5'ETH-hOTC (CO)-3'ETH (Table 9, SEQ ID NO: 38), T7-5'hAg-hOTC (Table 9, SEQ ID NO: 33), and T7-5'hAg-hOTC(CO) (Table 9, SEQ ID NO: 37) respectively.

OTC-activity in HepG2 cells (ACC 180, DSMZ, Germany) was detected by OTC-activity assay. HepG2 cells were seeded per well in 96-well plates. 24 h after seeding cells were transfected with 4-500-ng/well OTC-SNIM® RNA with different UTRs using Lipofectamine2000 (cat #11668027, Thermo-Fisher Scientific, Germany) 6, 24, 48, 72 and 144 h after transfection cells were lysed, frozen and OTC-activity assay was performed. Protocol adapted from Ye et al., 1996 (YE, X., ROBINSON, M, BATSHAW, M., FURTH, E., SMITH, I., and WILSON, J. (1996). *Prolonged metabolic correction in adult ornithine transcarbamylase deficiency mice with adenoviral vectors. J. Biol. Chem.* 271, 3639-3646). Plates were thawed at 37° C. (app. 15 min). Citrulline-standards (cat #C7629, sigma-aldrich, Germany) controls were added to the wells. The substrates ornithine (cat #02375 sigma-aldrich, Germany) and carbamoylphosphate (Lithium carbamoylphosphate dibasic hydrate, cat #C5625, sigma-aldrich, Germany, prepared freshly from dry powder stored at −20° C.) were added. Plates were incubated at 37° C. for 30 min. During that time OTC converted ornithine and carbamoylphosphate to citrulline and orthophosphate. To stop the enzymatic reaction, a mix of phosphoric acid and sulphuric acid (sigma-aldrich, Germany) was added. Thus, the pH was lowered and the detection reaction was started. For the detection of citrulline, diacetylmonooxim (2,3-Butanedione monoxime, B0753, sigma-aldrich, Germany) was added and the plates were heated up to 70° C. for 15 min. In a reaction called Fearon-reaction citrulline was converted to a yellow product (Abs 490 nm). The absorbance was measured using a Tecan Infinite F200 Pro plate reader (Tecan, Austria). Absolute citrulline values were determined by a standard curve. Furthermore, area under curve (activity over time) was calculated. Mean+/−SEM of three independent experiments was calculated.

Example 11

OTC Activity After Exogenous Expression of OTC Protein by SNIM® RNA in HepG2 Cells FIG. 5(C) shows OTC activity after exogenous expression of OTC protein by OTC encoding modified polyribonucleotides (e.g., OTC-SNIM® RNA) in HepG2 cells. Modified polyribonucleotides were generated by in vitro transcription in the presence of 35% 5-iodouridine-5'-triphosphate and 7.5% 5-iodocytidine-5'-triphosphate of Construct T7-5'hAg-hOTC(CO) (Table 9, SEQ ID NO: 37) or T7-TISU-hOTC (CO) (Table 9, SEQ ID NO: 39). OTC-activity was detected by OTC activity assay.5x104 HepG2 cells were seeded in 96 well plates. 24 h after seeding cells were transfected with OTC-encoding modified polyribonucleotides (e.g., OTC-SNIM® RNA) using Lipofectamine2000 (cat #11668027, Thermo-Fisher Scientific, Germany) 24 h after transfection, OTC-activity assay was performed.

OTC-activity in HepG2 cells (ACC 180, DSMZ, Germany) was detected by OTC-activity assay. $5\times10^4$ HepG2 cells were seeded per well in 96-well plates. 24 h after seeding cells were transfected with 500-4 ng/well OTC-SNIM® RNA with different UTRs or 500 ng/well EGFP-SNIM® RNA or OTC-STOP-SNIM® RNA (this RNA is not translated due to mutated start codons) using Lipofectamine2000 (cat #11668027, Thermo-Fisher Scientific, Germany). 24 h after transfection cells were lysed, frozen and OTC-activity assay was performed. Protocol adapted from Ye et al., 1996 (YE, X., ROBINSON, M., BATSHAW, M., FURTH, E., SMITH, I., and WILSON, J. (1996). *Prolonged metabolic correction in adult ornithine transcarbamylase deficiency mice with adenoviral vectors. J. Biol. Chem.* 271, 3639-3646). Plates were thawed at 37° C. (app. 15 min). Citrulline-standards (cat #C7629, sigma-aldrich, Germany) controls were added to the wells. The substrates ornithine (cat #02375 sigma-aldrich, Germany) and carbamoylphosphate (Lithium carbamoylphosphate dibasic hydrate, cat #C5625, sigma-aldrich, Germany, prepared freshly from dry powder stored at −20° C.) were added. Plates were incubated at 37° C. for 30 min During that time OTC converted ornithine and carbamoylphosphate to citrulline and ortho-phosphate. To stop the enzymatic reaction, a mix of phosphoric acid and sulphuric acid (sigma-aldrich, Germany) was added. Thus, the pH was lowered and the detection reaction was started. For the detection of citrulline, diacetylmonooxim (2,3-Butanedione monoxime, B0753, sigma-aldrich, Germany) was added and the plates were heated up to 70° C. for 15 min. In a reaction called Fearon-reaction citrulline was converted to a yellow product (Abs 490 nm). The absorbance was measured using a Tecan Infinite F200 Pro plate reader (Tecan, Austria). Absolute citrulline values were determined by a standard curve. Mean+/−SEM of three experimental replicates was calculated.

Example 12

IP-10 Induction is Reduced in Codon Optimized OTC Constructs

FIG. 6 shows IP-10 induction is reduced in codon optimized OTC constructs. SNIM®-RNA was generated through in vitro transcription in the presence of 50% 5-iodouridine-5'-triphosphate and 30% 2'-fluoro-2'-deoxycytidine-5'-triphosphate of Constructs T7-hOTCcDNA (Table 9, SEQ ID NO: 31), T7-hOTCcDNA(CO) (Table 9, SEQ ID NO: 35), T7-hOTC (Table 9, SEQ ID NO: 32), T7-hOTC (CO) (Table 9, SEQ ID NO: 36), T7-5'ETH-hOTC-3'ETH (Table 9, SEQ ID NO: 34), T7-5'ETH-hOTC(CO)-3'ETH (Table 9, SEQ ID NO: 38), T7-5'hAg-hOTC (Table 9, SEQ ID NO: 33), and T7-5'hAg-hOTC(CO) (Table 9, SEQ ID NO: 37) respectively.

IP-10 induction after transfection was determined in HepG2 cells (ACC 180, DSMZ, Germany). $5\times10^4$ cells were seeded per well in 96-well plates. 24 h after seeding cells were transfected with 500-8 ng/well OTC-SNIM® RNA with different UTRs using Lipofectamine2000 (cat #11668027, Thermo-Fisher Scientific, Germany). 24 h after transfection IP-10 levels of different cytokines in cell culture supernatants were measured with the ProcartaPlex™ Multiplex Immunoassay custom kits (Affymetrix eBioscience, USA) in combination with the Magpix instrument (Luminex®, USA). Mean+/−SEM of three independent experiments was calculated.

Example 13

Induction of OTC Protein in HepG2 Cells 8-12 h After Transfection

FIG. 7(A) shows the induction of OTC protein in HepG2 cells 8-12 h after transfection. SNIM®-RNA was generated through in vitro transcription in the presence of 35% 5-iodouridine-5'-triphosphate and 7.5% 2'-fluoro-2'-deoxycytidine-5'-triphosphate of Constructs T7-hOTCcDNA(CO) (Table 9, SEQ ID NO: 37 SNIM®. The respective hOTC-STOP-RNA was used as a negative control.

OTC-protein was detected by Western blot. $5\times10^4$ HepG2 cells (ACC 180, DSMZ, Germany) per well were seeded in 96 well plates. 24 h after seeding cells were transfected with 500-4 ng/well OTC-SNIM® RNA using Lipofectamine2000 (cat #11668027, Thermo-Fisher Scientific, Germany). 6, 8, 10, 12, 24 and 48 h after transfection cells were lysed using lysis buffer (25 mM TRIS, 0.1% Triton-X 100) complemented with protease inhibitor (cOmplete, EDTA-free, cat #11873580001, Roche, Germany) and DNase (DNase I Solution (2500 U/mL), cat #90083, Thermo Fisher Scientific, Germany). After lysis the samples were mixed with NuPAGE® LDS Sample Buffer (NP0007) and NuPAGE® Sample Reducing Agent (10×) (NP0004) and heated for 10 min at 70° C. Gel electrophoresis was performed using 15 μL of the lysate on NuPAGE 10% Bis-Tris Midi Gels (WG1203BOX) with the XCell4 SureLock™ Midi Cell, Thermo-Fisher Scientific, Germany The gels were blotted on a PVDF membrane using Trans-Blot Turbo Transfer Pack, Midi, PVDF, 7×8.5 cm (cat #1704157, Bio-Rad, Germany) and a Trans-Blot Turbo instrument (cat #1704155SP1, Bio-Rad, Germany). Membranes were blocked in NET-gelatin buffer (50 mM Tris [pH 7.5], 150 mM NaCl, 0.05% Triton™ X-100, 5 min EDTA and 0.25% gelatin (sigma-aldrich, Germany) for 30 min before the membranes were incubated overnight at 4° C. with the primary antibody, diluted in NET-gelatin. After three washes with NET-gelatin, horseradish peroxidase-conjugated secondary antibody was added for 1 h at RT. The membrane was washed again three times with NET-gelatin until signals were visualized with a chemiluminescent substrate kit (Luminata Crescendo Western HRP substrate, cat #WBLUR0100 Merck Millipore, Germany) and recorded using the ChemiDoc™ MP System, Bio-Rad, Germany Rabbit anti-OTC, cat #AP6928c, ABGENT (BioCat), USA, Dilution 1:2000

Rabbit anti-Vinculin, cat #ab91459, abcam, UK, Dilution 1:5000

Goat anti-rabbit IgG-HRP, cat #2004, SCBT, USA, Dilution 1:10000

Example 14

OTC Activity After Transfection with OTC-SNIM® RNA in HepG2 Cells

FIG. 7(B) shows OTC activity after transfection with OTC-SNIM® RNA in HepG2 cells. SNIM®-RNA was generated through in vitro transcription in the presence of 35% 5-iodouridine-5'-triphosphate and 7.5% 5-iodocytidine-5'-triphosphate of Constructs T7-hOTCcDNA(CO) (Table 9, SEQ ID NO: 37). The respective SNIM® hOTC-STOP-RNA was used as a negative control.

OTC-activity in HepG2 cells (ACC 180, DSMZ, Germany) was detected by OTC-activity assay. $5\times10^4$ HepG2 cells were seeded per well in 96-well plates. 24 h after seeding cells were transfected with 500-4 ng/well OTC-SNIM® RNA or 500 ng/well OTC-STOP-SNIM® RNA (this RNA is not translated due to mutated start codons) using Lipofectamine2000 (cat #11668027, Thermo-Fisher Scientific, Germany). 0.5, 1, 2, 3, 4, 6, 8, 10, 12, 24 and 48 h after transfection cells were lysed, frozen and OTC-activity assay was performed. Protocol adapted from Ye et al., 1996 (YE, X., ROBINSON, M., BATSHAW, M, FURTH, E., SMITH, I., and WILSON, J. (1996). *Prolonged metabolic correction in adult ornithine transcarbamylase deficiency mice with adenoviral vectors. J. Biol. Chem.* 271, 3639-3646). Plates were thawed at 37° C. (app. 15 min). Citrulline-standards (cat #C7629, sigma-aldrich, Germany) controls were added to the wells. The substrates ornithine (cat #02375 sigma-aldrich, Germany) and carbamoylphosphate (Lithium carbamoylphosphate dibasic hydrate, cat #C5625, sigma-aldrich, Germany, prepared freshly from dry powder stored at −20° C.) were added. Plates were incubated at 37° C. for 30 min During that time OTC converted ornithine and carbamoylphosphate to citrulline and orthophosphate. To stop the enzymatic reaction, a mix of phosphoric acid and sulphuric acid (sigma-aldrich, Germany) was added. Thus, the pH was lowered and the detection reaction was started. For the detection of citrulline, diacetylmonooxim (2,3-Butanedione monoxime, B0753, sigma-aldrich, Germany) was added and the plates were heated up to 70° C. for 15 min In a reaction called Fearon-reaction citrulline was converted to a yellow product (Abs 490 nm). The absorbance was measured using a Tecan Infinite F200 Pro plate reader (Tecan, Austria). Absolute citrulline values were determined by a standard curve. Mean+/−SEM of three experimental replicates was calculated.

Example 15

SNIM® RNA Allows Long Term Expression of OTC

FIG. 7(C) shows that SNIM® RNA allows long term expression of OTC. SNIM®-RNA was generated through in vitro transcription in the presence of 35% 5-iodouridine-5'-triphosphate and 7.5% 5-iodocytidine-5'-triphosphate of Constructs T7-hOTCcDNA(CO) (Table 9, SEQ ID NO: 37). The respective SNIM® hOTC-STOP-RNA was used as a negative control.

OTC-protein was detected by Western blot. $5\times10^4$ HepG2 cells (ACC 180, DSMZ, Germany) per well were seeded in 24 well plates. 24 h after seeding cells were transfected with 500-4 ng/well OTC-SNIM® RNA or OTC-STOP-SNIM® RNA (this RNA is not translated due to mutated start codons) using Lipofectamine2000 (cat #11668027, Thermo-Fisher Scientific, Germany). 6, 8, 10, 12, 24 and 48 h after transfection cells were lysed using lysis buffer (25 mM TRIS, 0.1% Triton-X 100) complemented with protease inhibitor (cOmplete, EDTA-free, cat #11873580001, Roche, Germany) and DNase (DNase I Solution (2500 U/mL), cat #90083, Thermo Fisher Scientific, Germany). As positive control 1 μg mouse liver lysate was used. After lysis the samples (250.62, 16 and 4 ng/well) were mixed with NuPAGE® LDS Sample Buffer (NP0007) and NuPAGE® Sample Reducing Agent (10×) (NP0004) and heated for 10 min at 70° C. Gel electrophoresis was performed using 15 μL of the lysate on NuPAGE 10% Bis-Tris Midi Gels (WG1203BOX) with the XCell4 SureLock™ Midi Cell, Thermo-Fisher Scientific, Germany. The gels were blotted on a PVDF membrane using Trans-Blot Turbo Transfer Pack, Midi, PVDF, 7×8.5 cm (cat #1704157, Bio-Rad, Germany) and a Trans-Blot Turbo instrument (cat #1704155SP1, Bio-Rad, Germany) Membranes were blocked in NET-gelatin buffer (50 mM Tris [pH 7.5], 150 mM NaCl, 0.05% Triton™ X-100, 5 mM EDTA and 0.25% gelatin (sigma-aldrich, Germany) for 30 min before the membranes were incubated overnight at 4° C. with the primary antibody, diluted in NET-gelatin. After three washes with NET-gelatin, horseradish peroxidase-conjugated secondary antibody was added for 1 h at RT. The membrane was washed again three times with NET-gelatin until signals were visualized with a chemiluminescent substrate kit (Luminata Crescendo Western HRP substrate, cat #WBLUR0100 Merck Millipore, Germany) and recorded using the ChemiDoc™ MP System, Bio-Rad, Germany. Densitometry was performed using the ImageLab™ software (Bio-Rad, Germany)

Rabbit anti-OTC, cat #AP6928c, ABGENT (BioCat), USA, Dilution 1:2000

Goat anti-rabbit IgG-HRP, cat #2004, SCBT, USA, Dilution 1:10000

Example 16

OTC Protein Translation After Transfection with OTC-SNIM® RNA in HepG2 Cells

FIG. 7(D) shows OTC protein translation after transfection with OTC-SNIM® RNA in HepG2 cells. SNIM®-RNA was generated through in vitro transcription in the presence of 35% 5-iodouridine-5'-triphosphate and 7.5% 5-iodocytidine-5'-triphosphate of Constructs T7-hOTCcDNA(CO) (Table 9, SEQ ID NO: 37). The respective SNIM® hOTC-STOP-RNA was used as a negative control.

Example 17

Quantification of Full Length SNIM® RNA in Liver Samples at 6 Hours After Intravenous Application in Balb/c Mice FIG. 8 shows the quantification of full length SNIM® RNA in vivo. SNIM®-RNA was generated through in vitro transcription in the presence of 50% 5-iodouridine-5'-triphosphate and 30% 2'-fluorocytidine-2'deoxy-5'-triphosphate of Constructs T7-5'hAg-OTC(CO) (SEQ ID NO: 25) and T7-mOTCORF(CO) (transcribed from SEQ ID NO: 45).

The in vivo expression of OTC-SNIM® RNA was analyzed in Balb/c mice at 6 h after i.v. injection. Endogenous OTC expression is at the normal physiologic level in this strain. In order to overcome this OTC endogenous expression, high doses (2 & 4 mg/kg) of formulated OTC-SNIM® RNA with mouse (SEQ ID NO: 45) and human sequences (SEQ ID NOs: 25 and 44), each in separate lipoplexes were applied. Delivered SNIM® RNA was detected by qPCR. For RNA isolation NucleoSpin RNA Plus Kit (cat #740984, Machery-Nagel, Germany) was used. 30-60 mg liver tissue samples were homogenized in 700 μL RNA lysis buffer and total RNA was isolated from 350 μL (yield, purity 7.2). To analyze only RNA with a poly-A tail, 1 μg of total RNA was reverse transcribed to cDNA using oligo-dT primer using Transcriptor First Strand cDNA Synthesis Kit (cat #896866001, Roche, Germany). qPCR primer pairs were designed for both applied RNAs ETH-OTC-RNA-18 (hOTC) and 27 (mOTC) (Table). Due to codon optimization of the sequences specific primers could be designed not detecting endogenous OTC-mRNA.

TABLE 12

| Species | Primer name | Primer forward | Primer reverse | UPL# |
|---|---|---|---|---|
| human | huOTCSNIM18#18 | ctcagagagaacgccaccat | aagttgcgcaccatgaagt | 18 |
| mouse | mOTCSNIM31#62 | tgagaaagggccacacaag | cagcatgtactggatctcttcg | 62 |

Both primer pairs were located in the initial one-third of the sequence to facilitate the analysis of complete, not degraded RNA molecules, containing a poly-A and also the 5' end of the sequence. A standard curve was generated using 1 μg total RNA (control liver) into which decreasing amounts ($1\times10^{-2}$-$1\times10^{-7}$ ng/1 μg total RNA) of either ETH-OTC-RNA-18 or-27 were spiked. UPL-based qPCR was performed on a LC96 (Roche) using FastStart Essential DNA Probes Master (cat #6402682001, Roche, Germany). A standard curve was generated (concentration of RNA against CT value) and results were calculated using Prism 6 for Windows (GraphPad Software, Inc., USA).

Example 18

Expression of OTC Protein In Liver Samples After Intravenous Application of OTC SNIM® RNA Human OTC SNIM® RNA (SEQ ID NO:25) and murine OTC SNIM® RNA (transcribed from SEQ ID NO:45), generated by in vitro transcription in the presence of 35% 5-iodouridine-5'-triphosphate and 7.5% 5-iodocytidine-5'-triphosphate respectively, were complexed in lipid formulations and applied intravenously into normal Balb/c mice. For human OTC SNIM® RNA, two doses (2 and 4 mg/kg) were tested whereas murine OTC SNIM® RNA was applied at 2 mg/kg doses. At 6 hours post treatment, mice were euthanized and livers were harvested for analysis of OTC protein using Western Blot.

These are the same liver samples from the experiment described in Example 17.

Western Blot analysis confirmed a 2-fold increase of OTC protein in liver samples from treated animals compared to vehicle controls. FIG. 9(A) is a representative Western blot for OTC and vinculin (used for normalization) from the analysed samples. Each animal sample was analysed in three independent Western blots. The densitometric analysis of the three replicate blots/sample is presented as FIG. 9(B).

Procedure for OTC Western Blot

Frozen livers were removed from the tube and a sample piece was cut off from the organ using a scalpel. Subsequently, the samples were put into a homogenizing-tube (Lysing Matrix D, cat #116913500, MP biomedicals, Germany) filled with 500 μL of lysis buffer (0.25 M Triethanolamine, 0.1% Triton X-100). Homogenization was performed for 3×20 sec in a Tissue homogenizer (MP FastPrep-24 Tissue and Cell Homogenizer, MP biomedicals, Germany). After homogenization, the samples were incubated for 10 min on ice and then centrifuged for 10 min at 4° C. with 20160 RCF in a Mikro 22R centrifuge (Hettich Zentrifugen, Germany) Subsequently, 200 μL of the supernatant was pipetted into a separate tube and diluted 1:100 in lysis buffer. BCA assay (BCA Protein Assay Kit, cat #, 23225, Thermo Fisher Scientific, Germany) was performed to determine the total protein concentration. 15 μg total protein lysate were mixed with 5 μL Bolt®LDS Sample Buffer (4×) (cat #B0007, Thermo-Fisher Scientific, Germany) and 1 μL Bolt® Sample Reducing Agent (cat #, B0009, Thermo-Fisher Scientific, Germany) and heated for 10 min at 70° C. SDS-PAGE was performed on Bolt™ 4-12% Bis-Tris Plus Gels (NWO4122BOX, Thermo-Fisher- Scientific, Germany). After electrophoresis gels were blotted on a PVDF membrane using Trans-Blot Turbo Transfer Pack, Mini, PVDF, 7×8.5 cm (cat #B170-4156, Bio-Rad, Germany) and a Trans-Blot Turbo instrument (cat #1704155SP1, Bio-Rad, Germany). After blotting, membranes were blocked in NET-gelatin buffer (50 mM Tris [pH 7.5], 150 mM NaCl, 0.05% Triton™ X-100, 5 mM EDTA and 0.25% gelatin (sigma-aldrich, Germany) for 30 min before the membranes were incubated overnight at 4° C. with the primary antibody, diluted in NET-gelatin. After three washes with NET-gelatin, horseradish peroxidase-conjugated secondary antibody was added for 1 h at RT. The membrane was washed again three times with NET-gelatin until signals were visualized with a chemiluminescent substrate kit (Luminata Crescendo Western HRP substrate, cat #WBLUR0100 Merck Millipore, Germany) and visualized using the ChemiDoc™ MP System, Bio-Rad, Germany Densitometry was performed using the ImageLab™ software (Bio-Rad, Germany). Rabbit anti-OTC, cat #AP6928c, ABGENT (BioCat), USA, Dilution 1:2000 (Antibody does not discriminate between mouse and human OTC)

Rabbit anti-Vinculin, cat #ab91459, abcam, UK, Dilution 1:10000

Goat anti-rabbit IgG-HRP, cat #2004, SCBT, USA, Dilution 1:10000

Example 19

Detection of Human OTC Specific Peptides in Liver Samples from Balb/c Mice Treated with Human OTC SNIM® RNA Liver samples from mice treated with 4 mg/kg human OTC SNIM® RNA (SEQ ID NO: 25), generated by in vitro transcription in the presence of 35% 5-iodouridine-5'-triphosphate and 7.5% 5-iodocytidine-5'-triphosphate respectively, were analysed by LC-MS/MS for the detection of human OTC specific peptides. The same liver samples had been analysed in Example 17 for the presence of SNIM® RNA and Example 18 for increased OTC protein. Samples from untreated mice served as negative control. A positive control was generated in which protein lysate from HepG2 cells transfected with human OTC SNIM® RNA (SEQ ID NO: 25) was spiked into liver protein lysate from untreated mouse. Human specific peptides were detected only in murine liver samples treated with human OTC SNIM® RNA (SEQ ID NO: 25) and these data are presented as FIG. 9C.

Procedure for LC-MS/MS Based Detection of Human OTC Specific Peptides

FIG. 9(C) shows an LC-MS/MS analysis of mouse liver samples (underlined=human specific). SNIM®-RNA was generated through in vitro transcription in the presence of 50% 5-iodouridine-5'-triphosphate and 30% 2'-fluro-2'-deoxycytidine-5'-triphosphate of Constructs T7-5'hAg-hOTC (CO) (SEQ ID NO: 25).

Human specific peptides in mouse liver lysates were detected by LC-MS/MS. Liver samples from the group treated with 4 mg/kg human OTC-SNIM® RNA, the control group (vehicle) and a positive control (HepG2 cell lysate from cells transfected with OTC-SNIM® RNA spiked in an untreated control liver sample, vehicle) were separated by SDS-PAGE. One gel was blotted on a membrane and OTC-Western Blot was performed as in-process control. From the second gel, sections from separated lanes (at 36-40 kDa) were excised. Excised gel-samples were transferred to in-gel-digest using Asp-N peptidase was performed. After digestion peptides were analyzed by LC-MS/MS.

Reduction, alkylation and tryptic digest: The SDS-PAGE bands were reduced with dithiothreitol (DTT) in order to break disulfide bonds, alkylated with iodoacetamide (IAA) in order to prevent their reformation and subsequently digested with Asp-N. Peptides were acidified to 1% FA.

Enzyme used: Asp-N: 0.02 μg, sequencing grade, Roche Diagnostics GmbH, Germany Nano-LC-ESI-MS Analysis: Half of the digest was used for MS/MS analysis. Separation was performed on an EASYnLC1000 system (Thermo Fisher Scientific) using the following columns and chromatographic conditions: Peptides were loaded onto a C18 column (Acclaim® PepMap 100 pre-column, C18, 3 μm, 2 cm×75 μm Nanoviper, Thermo Fisher Scientific) and subsequently fractionated on an analytical column (EASY-Spray column, 25 cm×75 μm ID, PepMap C18 2 μm particles, 100 Å pore size, Thermo Fisher Scientific) using a linear gradient (A: 0.1% formic acid in water; B: 0.1% formic acid in ACN) at a flow rate of 280 nl/min The gradient used was: 1-30% B in 80 minutes, 30-60% B in 20 minutes, 100% B for 10 minutes. Mass spectrometry was performed on a linear ion trap mass spectrometer (Thermo LTQ Orbitrap XL, Thermo Electron) coupled online to the nano-LC system. For electrospray ionization a distal coated SilicaTip (FS-360-50-15-D-20) and a needle voltage of 1.4 kV was used. The LTQ Orbitrap was operated in parallel mode performing precursor mass scanning in the Orbitrap (60 000 FWHM resolution at m/z 400) and isochronous acquisition of five data dependent CID MS/MS scans of the most intense precursor signals in the LTQ ion trap using a normalized collision energy of 35%. After two repeated fragmentations within 15 sec the precursor was excluded for 180 sec. An inclusion list was used for peptides up to missed cleavage 1. Moreover, annotated modifications like acetylation, succinylation and phosphorylation were also included in this list (Uniprot entry P00480). In case a mass of the inclusion list was detected a MS/MS was triggered independent of the precursor intensity. In total always five MS/MS spectra were acquired.

Database search and quantification: Protein identification was done with the software Mascot with the settings given below. Two separate database searches were performed against the human and mouse sequences of the SwissProt database. Additionally, database searches were performed against the customer sequence allowing for variable modifications of acetylation, succinylation and phosphorylation using an in-house Mascot server.

Mascot Settings:

Database: SwissProt (last updated Mar. 15, 2015)

Taxonomy: human or Mus Musculus

Enzyme: Asp-N

Fixed modifications: Carbamidomethyl (C)

Variable modifications: Oxidation (M)

Mass values: Monoisotopic

Protein Mass: Unrestricted

Peptide Mass Tolerance: ±50 ppm

Fragment Mass Tolerance: ±0.6 Da

Max Missed Cleavages: 2

Instrument type: ESI-TRAP

Database: Customer_database database_(7 sequences; 2140 residues)

Taxonomy: unrestricted

Enzyme: Asp-N_ambic

Fixed modifications: Carbamidomethyl (C)

Variable modifications: Oxidation (M), Acetyl (K), Phospho (ST), Succinyl_N6 (K)

Mass values: Monoisotopic
Protein Mass: Unrestricted
Peptide Mass Tolerance: ±50 ppm
Fragment Mass Tolerance: ±0.8 Da
Max Missed Cleavages: 4
Instrument type: ESI-TRAP

Example 20

Expression of Human OTC Protein and its Physiological Activity in OTC Knockout Mice (OTC$^{spf\ ash}$) After Single Application of Human OTC SNIM® RNA Human OTC SNIM® RNA (SEQ ID NO: 25), generated by in vitro transcription in the presence of 35% 5-iodouridine-5'-triphosphate and 7.5% 5-iodocytidine-5'-triphosphate respectively, was complexed in a lipid formulation and applied intravenously into OTC knockout mice (OTC$^{spf\ ash}$). Two different doses (0.5 mg/kg and 2 mg/kg) were tested in the current PK/PD study. Mice were injected at day 1 and then analysed at day 2, 5, 8 and 12 for OTC protein (Western blot) and blood ammonia levels (as a marker for physiological activity of the expressed OTC protein).

For Western Blot analysis, experimental procedure described in Example 18 was followed. Densitometric analysis of Western blots as presented as FIG. 11. Each symbol represents the mean intensity ratio of OTC/Vinculin (mean of three replicate Western blots) from each animal. t-test was performed using GraphPadPrism.

Significantly higher amounts of OTC protein were detected in liver samples from mice treated with a single dose of human OTC SNIM® RNA (SEQ ID NO: 25) at high dose (2 mg/kg) for a period of up to 11 days post single application.

Besides OTC protein, the functionality of the expressed protein was analysed by measuring blood ammonia levels at different time points post treatment. These data are provided in FIG. 12.

Experimental Procedure

OTC$^{spf\text{-}ash\ mice}$ were treated on day 1 with either 0.5 or 2 mg/kg human OTC SNIM RNA (SEQ ID NO: 25) or with 2% sucrose (vehicle control) (n=6/dose and time point). Animals were challenged i.p. with 0.2 M $NH_4C1$ solution (Dose 5 mmol/kg b.w.) at 2, 5, 8, or 12 days. Shortly before the challenge, blood samples were taken for ammonia measurement (pre). Terminal samples, as well as liver, lung, spleen and urine were collected 40 min after the challenge.

Relative OTC expression as quantified using Western Blot correlated with reduction in plasma ammonia levels. Furthermore, a physiological effect (reduction of ammonia levels) was seen also in animals treated with a low dose of human OTC SNIM® RNA (SEQ ID NO: 25).

Correlation analysis using data points for all animals at all time points are shown in FIG. 13.

These data confirm expression and physiological activity of human OTC SNIM® RNA (SEQ ID NO: 25) after a single intravenous application for up to 11 days post treatment in an OTC mouse model.

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

Sequence Listing

1. Coding Sequences

The following polyribonucleotide (e.g., RNA) sequence (SEQ ID NO: 1) encodes wildtype human ornithine transcarbamylase (OTC) as annotated under NCBI Reference Sequence NM_000531.5 (the region encoding the signal peptide for mitochondrial import is underlined)

(SEQ ID NO: 1)

augcuguuuaaucugaggauccuguuaaacaaugcagcuuuuagaaauggu cacaacuucaugguucgaaauuuucgguguggacaaccacuacaaaauaaa gugcagcugaagggccgugaccuucucacucuaaaaacuuuaccggagaa gaaauuaaauauaugcuauggcuaucagcagaucugaaauuuaggauaaaa cagaaaggagaguauuugccuuuauugcaagggaaguccuuaggcaugauu uuugagaaaagaaguacucgaacaagauugucuacagaaacaggcuuugca cuucugggaggacauccuuguuuucuuaccacacaagauauucauuugggu gugaaugaaagucucacggacacggcccguguauugucuagcauggcagau gcaguauuggcucgaguguauaaacaaucagauuuggacacccuggcuaaa gaagcauccaucccaauuaucaaugggcugucagauuuguaccauccuauc cagauccuggcugauuaccucacgcuccaggaacacuauagcucucugaaa ggucuuacccucagcuggaucggggaugggaacaauauccugcacuccauc augaugagcgcagcgaaauucggaaugcaccuucaggcagcuacuccaaag gguuaugagccggaugcuaguguaaccaaguuggcagagcaguaugccaaa gagaaugguaccaagcuguugcugacaaaugauccauuggaagcagcgcau ggaggcaauguauuaauuacagacacuuggauaagcaugggacaagaagag gagaagaaaaagcggcuccaggcuuuccaagguuaccagguuacaaugaag acugcuaaaguugcugccucugacuggacauuuuuacacugcuugcccaga aagccagaagaaguggaugaugaagucuuuuauucuccucgaucacuagug uucccagaggcagaaaacagaaaguggacaaucauggcugucauggugucc cugcugacagauuacucaccucagcuccagaagccuaaauuuuga The following nucleotide (e.g., DNA) sequence (SEQ ID NO: 2) encodes wildtype human ornithine transcarbamylase (OTC) as annotated under NCBI Reference Sequence NM_000531.5 (the region encoding the signal peptide for mitochondrial import is underlined)

(SEQ ID NO: 2)

Atgctgtttaatctgaggatcctgttaaacaatgcagcttttagaaatggt cacaacttcatggttcgaaattttcggtgtggacaaccactacaaaataaa gtgcagctgaagggccgtgaccttctcactctaaaaactttaccggagaa -continued gaaattaaatatatgctatggctatcagcagatctgaaatttaggataaaa cagaaaggagagtatttgcctttattgcaagggaagtccttaggcatgatt tttgagaaaagaagtactcgaacaagattgtctacagaaacaggctttgca cttctgggaggacatccttgttttcttaccacacaagatattcatttgggt gtgaatgaaagtctcacggacacggcccgtgtattgtctagcatggcagat gcagtattggctcgagtgtataaacaatcagatttggacaccctggctaaa gaagcatccatcccaattatcaatgggctgtcagatttgtaccatcctatc cagatcctggctgattacctcacgctccaggaacactatagctctctgaaa ggtcttaccctcagctggatcggggatgggaacaatatcctgcactccatc atgatgagcgcagcgaaattcggaatgcaccttcaggcagctactccaaag ggttatgagccggatgctagtgtaaccaagttggcagagcagtatgccaaa gagaatggtaccaagctgttgctgacaaatgatccattggaagcagcgcat ggaggcaatgtattaattacagacacttggataagcatgggacaagaagag gagaagaaaaagcggctccaggctttccaaggttaccaggttacaatgaag actgctaaagttgctgcctctgactggacatttttacactgcttgcccaga aagccagaagaagtggatgatgaagtcttttattctcctcgatcactagtg ttcccagaggcagaaaacagaaagtggacaatcatggctgtcatggtgtc cctgctgacagattactcacctcagctccagaagcctaaatttga The following amino acid sequence (SEQ ID NO: 3) shows the human wildtype ornithine transcarbamylase (OTC) as annotated under NCBI Reference Sequence NM_000531.5 (the signal peptide for mitochondrial import is underlined)

(SEQ ID NO: 3)
MLFNLRILLNNAAFRNGHNFMVRNFRCGQPLQNKVQLKGRDLLTLKNFTG

EEIKYMLWLSADLKFRIKQKGEYLPLLQGKSLGMIFEKRSTRTRLSTETG

FALLGGHPCFLTTQDIHLGVNESLTDTARVLSSMADAVLARVYKQSDLDT

LAKEASIPIINGLSDLYHPIQILADYLTLQEHYSSLKGLTLSWIGDGNNI

LHSIMMSAAKFGMHLQAATPKGYEPDASVTKLAEQYAKENGTKLLLTNDP

LEAAHGGNVLITDTWISMGQEEEKKKRLQAFQGYQVTMKTAKVAASDWTF

LHCLPRKPEEVDDEVFYSPRSLVFPEAENRKWTIMAVMVSLLTDYSPQLQ

KPKF

The following polyribonucleotide (e.g., RNA) sequence (SEQ ID NO: 4) encodes wildtype human ornithine transcarbamylase (OTC) but is codon-optimized (the signal peptide for mitochondrial import is underlined)

(SEQ ID NO: 4)
AUGCUGUUCAACCUGCGGAUCCUGCUGAACAACGCCGCCUUCCGGAACGG

CCACAACUUCAUGGUGCGCAACUUCAGAUGCGGCCAGCCCCUGCAGAACA

AGGUGCAGCUGAAGGGCAGGGACCUGCUGACCCUGAAGAACUUCACCGGC

GAAGAGAUCAAGUACAUGCUGUGGCUGAGCGCCGACCUGAAGUUCCGGAU

CAAGCAGAAGGGCGAGUACCUGCCCCUGCUGCAGGGCAAGUCUCUGGGCA

UGAUCUUCGAGAAGCGGAGCACCCGGACCCGGCUGUCUACCGAGACAGGA

-continued

UUUGCCCUGCUGGGCGGCCACCCUUGCUUUCUGACCACCCAGGAUAUCCA

CCUGGGCGUGAACGAGAGCCUGACCGACACAGCCAGAGUGCUGAGCAGCA

UGGCCGAUGCCGUGCUGGCCAGAGUGUACAAGCAGAGCGACCUGGACACC

CUGGCCAAAGAGGCCAGCAUCCCCAUCAUCAACGGCCUGUCCGACCUGUA

CCACCCCAUCCAGAUCCUGGCCGACUACCUGACCCUGCAGGAACACUACA

GCUCCCUGAAGGGCCUGACACUGAGCUGGAUCGGCGACGGCAACAACAUC

CUGCACUCUAUCAUGAUGAGCGCCGCCAAGUUCGGCAUGCAUCUGCAGGC

CGCCACCCCCAAGGGCUAUGAGCCUGAUGCCAGCGUGACCAAGCUGGCCG

AGCAGUACGCCAAAGAGAACGGCACCAAGCUGCUGCUGACCAACGACCCU

CUGGAAGCCGCCCACGGCGGCAAUGUGCUGAUCACCGAUACCUGGAUCAG

CAUGGGCCAGGAAGAGGAAAAGAAGAAGCGGCUGCAGGCCUUCCAGGGCU

ACCAAGUGACCAUGAAGACCGCCAAAGUGGCCGCCAGCGACUGGACCUUC

CUGCACUGCCUGCCCAGAAAGCCCGAAGAGGUGGACGACGAGGUGUUCUA

CAGCCCCCGGUCCCUGGUGUUUCCCGAGGCCGAGAACCGGAAGUGGACCA

UCAUGGCUGUGAUGGUGUCUCUGCUGACCGACUACUCCCCCCAGCUGCAG

AAGCCCAAGUUCUGA

The following nucleotide (e.g., DNA) sequence (SEQ ID NO: 5) encodes wildtype human ornithine transcarbamylase (OTC) but is codon-optimized (the signal peptide for mitochondrial import is underlined)

(SEQ ID NO: 5)
ATGCTGTTCAACCTGCGGATCCTGCTGAACAACGCCGCCTTCCGGAACGG

CCACAACTTCATGGTGCGCAACTTCAGATGCGGCCAGCCCCTGCAGAACA

AGGTGCAGCTGAAGGGCAGGGACCTGCTGACCCTGAAGAACTTCACCGGC

GAAGAGATCAAGTACATGCTGTGGCTGAGCGCCGACCTGAAGTTCCGGAT

CAAGCAGAAGGGCGAGTACCTGCCCCTGCTGCAGGGCAAGTCTCTGGGCA

TGATCTTCGAGAAGCGGAGCACCCGGACCCGGCTGTCTACCGAGACAGGA

TTTGCCCTGCTGGGCGGCCACCCTTGCTTTCTGACCACCCAGGATATCCA

CCTGGGCGTGAACGAGAGCCTGACCGACACAGCCAGAGTGCTGAGCAGCA

TGGCCGATGCCGTGCTGGCCAGAGTGTACAAGCAGAGCGACCTGGACACC

CTGGCCAAAGAGGCCAGCATCCCCATCATCAACGGCCTGTCCGACCTGTA

CCACCCCATCCAGATCCTGGCCGACTACCTGACCCTGCAGGAACACTACA

GCTCCCTGAAGGGCCTGACACTGAGCTGGATCGGCGACGGCAACAACATC

CTGCACTCTATCATGATGAGCGCCGCCAAGTTCGGCATGCATCTGCAGGC

CGCCACCCCCAAGGGCTATGAGCCTGATGCCAGCGTGACCAAGCTGGCCG

AGCAGTACGCCAAAGAGAACGGCACCAAGCTGCTGCTGACCAACGACCCT

CTGGAAGCCGCCCACGGCGGCAATGTGCTGATCACCGATACCTGGATCAG

CATGGGCCAGGAAGAGGAAAAGAAGAAGCGGCTGCAGGCCTTCCAGGGCT

ACCAAGTGACCATGAAGACCGCCAAAGTGGCCGCCAGCGACTGGACCTTC

CTGCACTGCCTGCCCAGAAAGCCCGAAGAGGTGGACGACGAGGTGTTCTA

-continued

CAGCCCCCGGTCCCTGGTGTTTCCCGAGGCCGAGAACCGGAAGTGGACCA

TCATGGCTGTGATGGTGTCTCTGCTGACCGACTACTCCCCCAGCTGCAG

AAGCCCAAGTTCTGA

2. Promoter Sequences

The following polyribonucleotide (e.g., RNA) sequence (SEQ ID NO: 6) corresponds to a T7 promoter sequence. The underlined G denotes the transcription start site.

(SEQ ID NO: 6)
1 UAAUACGACU CACUAUAG GGAGA

The following polyribonucleotide (e.g., RNA) sequence (SEQ ID NO: 7) corresponds to a T3 promoter sequence. The underlined G denotes the transcription start site.

(SEQ ID NO: 7)
1 AAUUAACCCU CACUAAAG GGAGA

The following polyribonucleotide (e.g., RNA) sequence (SEQ ID NO: 8) corresponds to a SP6 promoter sequence. The underlined G denotes the transcription start site.

(SEQ ID NO: 8)
1 AUUUAGGUGA CACUAUAG AAG

The following polyribonucleotide (e.g., RNA) sequence (SEQ ID NO: 9) corresponds to a K11 promoter sequence. The underlined G denotes the transcription start site.

(SEQ ID NO: 9)
1 AAUUAGGGCA CACUAUAGGG A

3. UTR Sequences

The following polyribonucleotide (e.g., RNA) sequence (SEQ ID NO: 10) corresponds to a 5' UTR referred to as Minimal (with the 3' part of the T7 promoter sequence).

(SEQ ID NO: 10)
1 GGGAGACGCC ACC

The following polyribonucleotide (e.g., RNA) sequence (SEQ ID NO: 11) corresponds to a 5' UTR referred to as Minimal.

(SEQ ID NO: 11)
1 CGCCACC

The following polyribonucleotide (e.g., RNA) sequence (SEQ ID NO: 12) corresponds to a 5' UTR referred to as hAg, a 5' UTR derived from human alpha globin (with the 3' part of the T7 promoter sequence).

(SEQ ID NO: 12)
1 GGGAGACUCU UCUGGUCCCC ACAGACUCAG AGAGAACGCC ACC

The following polyribonucleotide (e.g., RNA) sequence (SEQ ID NO: 13) corresponds to a 5' UTR referred to as hAg, a 5' UTR derived from human alpha globin, without promoter sequence.

(SEQ ID NO: 13)
1 CUCUUCUGGUC CCCACAGACU CAGAGAGAAC GCCACC

The following polyribonucleotide (e.g., RNA) sequence (SEQ ID NO: 14) corresponds to a 5' UTR referred to as TISU (with the 3' part of the T7 promoter sequence).

(SEQ ID NO: 14)
1 GGGAGACGCC AAG

The following polyribonucleotide (e.g., RNA) sequence (SEQ ID NO: 15) corresponds to a 5' UTR referred to as TISU, without promoter sequence.

(SEQ ID NO: 15)
1 GCCAAG

The following polyribonucleotide (e.g., RNA) sequence (SEQ ID NO: 16) corresponds to a 5' UTR referred to as TISU+T (with the 3' part of the T7 promoter sequence).

(SEQ ID NO: 16)
1 GGGAGACUGC CAAG

The following polyribonucleotide (e.g., RNA) sequence (SEQ ID NO: 17) corresponds to a 5' UTR referred to as TISU+T, without promoter sequence.

(SEQ ID NO: 17)
1 CUGCCAAG

The following polyribonucleotide (e.g., RNA) sequence (SEQ ID NO: 18) corresponds to a 5' UTR referred to as CYBA 5' UTR, without promoter sequence.

(SEQ ID NO: 18)
1 C CGCGCCUAGC AGUGUCCCAG CCGGGUUCGU GUCGCCGCCA CC

The following polyribonucleotide (e.g., RNA) sequence (SEQ ID NO: 19) corresponds to a 3' UTR referred to as CYBA 3' UTR.

(SEQ ID NO: 19)
1 CCUCGCCCCG GACCUGCCCU CCCGCCAGGU GCACCCACCU GCAAUAAAUG

51 CAGCGAAGCC GGGA

The following polyribonucleotide (e.g., RNA) sequence (SEQ ID NO: 20) corresponds to a 5' UTR referred to as CYBA 5' UTR, with the 3' part of the T7 promoter sequence.

```
                                            (SEQ ID NO: 20)
1    GGGAGACCGC GCCUAGCAGU GUCCCAGCCG GGUUCGUGUC GCCGCCACC
```

4. Specific Constructs (UTRs+Coding Sequences)

The following sequence (SEQ ID NO: 21) corresponds to a polyribonucleotide (e.g., RNA) sequence comprising Minimal UTR (SEQ ID NO: 10) and human wildtype OTC (SEQ ID NO: 1).

```
                                          (SEQ ID NO: 21)
GGGAGACGCCACCAUGCUGUUUAAUCUGAGGAUCCUGUUAAACAAUGCAG
CUUUUAGAAAUGGUCACAACUUCAUGGUUCGAAAUUUUCGGUGUGGACAA
CCACUACAAAAUAAAGUGCAGCUGAAGGGCCGUGACCUUCUCACUCUAAA
AAACUUUACCGGAGAAGAAAUUAAAUAUAUGCUAUGGCUAUCAGCAGAUC
UGAAAUUUAGGAUAAAACAGAAAGGAGAGUAUUUGCCUUUAUUGCAAGGG
AAGUCCUUAGGCAUGAUUUUUGAGAAAAGAAGUACUCGAACAAGAUUGUC
UACAGAAACAGGCUUUGCACUUCUGGGAGGACAUCCUUGUUUUCUUACCA
CACAAGAUAUUCAUUUGGGUGUGAAUGAAAGUCUCACGGACACGGCCCGU
GUAUUGUCUAGCAUGGCAGAUGCAGUAUUGGCUCGAGUGUAUAAACAAUC
AGAUUUGGACACCCUGGCUAAAGAAGCAUCCAUCCCAAUUAUCAAUGGGC
UGUCAGAUUUGUACCAUCCUAUCCAGAUCCUGGCUGAUUACCUCACGCUC
CAGGAACACUAUAGCUCUCUGAAAGGUCUUACCCUCAGCUGGAUCGGGGA
UGGGAACAAUAUCCUGCACUCCAUCAUGAUGAGCGCAGCGAAAUUCGGAA
UGCACCUUCAGGCAGCUACUCCAAAGGGUUAUGAGCCGGAUGCUAGUGUA
ACCAAGUUGGCAGAGCAGUAUGCCAAAGAGAAUGGUACCAAGCUGUUGCU
GACAAAUGAUCCAUUGGAAGCAGCGCAUGGAGGCAAUGUAUUAAUUACAG
ACACUUGGAUAAGCAUGGGACAAGAAGAGGAGAAGAAAAAGCGGCUCCAG
GCUUUCCAAGGUUACCAGGUUACAAUGAAGACUGCUAAAGUUGCUGCCUC
UGACUGGACAUUUUUACACUGCUUGCCCAGAAAGCCAGAAGAAGUGGAUG
AUGAAGUCUUUUAUUCUCCUCGAUCACUAGUGUUCCCAGAGGCAGAAAAC
AGAAAGUGGACAAUCAUGGCUGUCAUGGUGUCCCUGCUGACAGAUUACUC
ACCUCAGCUCCAGAAGCCUAAAUUUUGA
```

The following sequence (SEQ ID NO: 22) corresponds to a polyribonucleotide (e.g., RNA) sequence comprising human alpha globin UTR (SEQ ID NO: 12) and human wildtype OTC (SEQ ID NO: 1).

```
                                          (SEQ ID NO: 22)
GGGAGACUCUUCUGGUCCCCACAGACUCAGAGAGAACGCCACCAUGCUGU
UUAAUCUGAGGAUCCUGUUAAACAAUGCAGCUUUUAGAAAUGGUCACAAC
UUCAUGGUUCGAAAUUUUCGGUGUGGACAACCACUACAAAAUAAAGUGCA
GCUGAAGGGCCGUGACCUUCUCACUCUAAAAAACUUUACCGGAGAAGAAA
UUAAAUAUAUGCUAUGGCUAUCAGCAGAUCUGAAAUUUAGGAUAAAACAG
AAAGGAGAGUAUUUGCCUUUAUUGCAAGGGAAGUCCUUAGGCAUGAUUUU
```

-continued

```
UGAGAAAAGAAGUACUCGAACAAGAUUGUCUACAGAAACAGGCUUUGCAC
UUCUGGGAGGACAUCCUUGUUUUCUUACCACACAAGAUAUUCAUUUGGGU
GUGAAUGAAAGUCUCACGGACACGGCCCGUGUAUUGUCUAGCAUGGCAGA
UGCAGUAUUGGCUCGAGUGUAUAAACAAUCAGAUUUGGACACCCUGGCUA
AAGAAGCAUCCAUCCCAAUUAUCAAUGGGCUGUCAGAUUUGUACCAUCCU
AUCCAGAUCCUGGCUGAUUACCUCACGCUCCAGGAACACUAUAGCUCUCU
GAAAGGUCUUACCCUCAGCUGGAUCGGGGAUGGGAACAAUAUCCUGCACU
CCAUCAUGAUGAGCGCAGCGAAAUUCGGAAUGCACCUUCAGGCAGCUACU
CCAAAGGGUUAUGAGCCGGAUGCUAGUGUAACCAAGUUGGCAGAGCAGUA
UGCCAAAGAGAAUGGUACCAAGCUGUUGCUGACAAAUGAUCCAUUGGAAG
CAGCGCAUGGAGGCAAUGUAUUAAUUACAGACACUUGGAUAAGCAUGGGA
CAAGAAGAGGAGAAGAAAAAGCGGCUCCAGGCUUUCCAAGGUUACCAGGU
UACAAUGAAGACUGCUAAAGUUGCUGCCUCUGACUGGACAUUUUUACACU
GCUUGCCCAGAAAGCCAGAAGAAGUGGAUGAUGAAGUCUUUUAUUCUCCU
CGAUCACUAGUGUUCCCAGAGGCAGAAAACAGAAAGUGGACAAUCAUGGC
UGUCAUGGUGUCCCUGCUGACAGAUUACUCACCUCAGCUCCAGAAGCCUA
AAUUUUGA
```

The following sequence (SEQ ID NO: 23) corresponds to a polyribonucleotide (e.g., RNA) sequence comprising CYBA 5' UTR (SEQ ID NO: 20), human wildtype OTC (SEQ ID NO: 1) and CYBA 3' UTR (SEQ ID NO: 19).

```
                                          (SEQ ID NO: 23)
GGGAGACCGCGCCUAGCAGUGUCCCAGCCGGGUUCGUGUCGCCGCCACCA
UGCUGUUUAAUCUGAGGAUCCUGUUAAACAAUGCAGCUUUUAGAAAUGGU
CACAACUUCAUGGUUCGAAAUUUUCGGUGUGGACAACCACUACAAAAUAA
AGUGCAGCUGAAGGGCCGUGACCUUCUCACUCUAAAAAACUUUACCGGAG
AAGAAAUUAAAUAUAUGCUAUGGCUAUCAGCAGAUCUGAAAUUUAGGAUA
AAACAGAAAGGAGAGUAUUUGCCUUUAUUGCAAGGGAAGUCCUUAGGCAU
GAUUUUUGAGAAAAGAAGUACUCGAACAAGAUUGUCUACAGAAACAGGCU
UUGCACUUCUGGGAGGACAUCCUUGUUUUCUUACCACACAAGAUAUUCAU
UUGGGUGUGAAUGAAAGUCUCACGGACACGGCCCGUGUAUUGUCUAGCAU
GGCAGAUGCAGUAUUGGCUCGAGUGUAUAAACAAUCAGAUUUGGACACCC
UGGCUAAAGAAGCAUCCAUCCCAAUUAUCAAUGGGCUGUCAGAUUUGUAC
CAUCCUAUCCAGAUCCUGGCUGAUUACCUCACGCUCCAGGAACACUAUAG
CUCUCUGAAAGGUCUUACCCUCAGCUGGAUCGGGGAUGGGAACAAUAUCC
UGCACUCCAUCAUGAUGAGCGCAGCGAAAUUCGGAAUGCACCUUCAGGCA
```

-continued

GCUACUCCAAAGGGUUAUGAGCCGGAUGCUAGUGUAACCAAGUUGGCAGA

GCAGUAUGCCAAAGAGAAUGGUACCAAGCUGUUGCUGACAAAUGAUCCAU

UGGAAGCAGCGCAUGGAGGCAAUGUAUUAAUUACAGACACUUGGAUAAGC

AUGGGACAAGAAGAGGAGAAGAAAAAGCGGCUCCAGGCUUUCCAAGGUUA

CCAGGUUACAAUGAAGACUGCUAAAGUUGCUGCCUCUGACUGGACAUUUU

UACACUGCUUGCCCAGAAAGCCAGAAGAAGUGGAUGAUGAAGUCUUUUAU

UCUCCUCGAUCACUAGUGUUCCCAGAGGCAGAAAACAGAAAGUGGACAAU

CAUGGCUGUCAUGGUGUCCCUGCUGACAGAUUACUCACCUCAGCUCCAGA

AGCCUAAAUUUUGACCUCGCCCCGGACCUGCCCUCCCGCCAGGUGCACCC

ACCUGCAAUAAAUGCAGCGAAGCCGGGA

The following sequence (SEQ ID NO: 24) corresponds to a polyribonucleotide (e.g., RNA) sequence comprising Minimal UTR (SEQ ID NO: 10) and human codon-optimized OTC (SEQ ID NO: 4).

(SEQ ID NO: 24)

GGGAGACGCCACCAUGCUGUUCAACCUGCGGAUCCUGCUGAACAACGCCG

CCUUCCGGAACGGCCACAACUUCAUGGUGCGCAACUUCAGAUGCGGCCAG

CCCCUGCAGAACAAGGUGCAGCUGAAGGGCAGGGACCUGCUGACCCUGAA

GAACUUCACCGGCGAAGAGAUCAAGUACAUGCUGUGGCUGAGCGCCGACC

UGAAGUUCCGGAUCAAGCAGAAGGGCGAGUACCUGCCCCUGCUGCAGGGC

AAGUCUCUGGGCAUGAUCUUCGAGAAGCGGAGCACCCGGACCCGGCUGUC

UACCGAGACAGGAUUUGCCCUGCUGGGCGGCCACCCUUGCUUUCUGACCA

CCCAGGAUAUCCACCUGGGCGUGAACGAGAGCCUGACCGACACAGCCAGA

GUGCUGAGCAGCAUGGCCGAUGCCGUGCUGGCCAGAGUGUACAAGCAGAG

CGACCUGGACACCCUGGCCAAAGAGGCCAGCAUCCCCAUCAUCAACGGCC

UGUCCGACCUGUACCACCCCAUCCAGAUCCUGGCCGACUACCUGACCCUG

CAGGAACACUACAGCUCCCUGAAGGGCCUGACACUGAGCUGGAUCGGCGA

CGGCAACAACAUCCUGCACUCUAUCAUGAUGAGCGCCGCCAAGUUCGGCA

UGCAUCUGCAGGCCGCCACCCCCAAGGGCUAUGAGCCUGAUGCCAGCGUG

ACCAAGCUGGCCGAGCAGUACGCCAAAGAGAACGGCACCAAGCUGCUGCU

GACCAACGACCCUCUGGAAGCCGCCCACGGCGGCAAUGUGCUGAUCACCG

AUACCUGGAUCAGCAUGGGCCAGGAAGAGGAAAAGAAGAAGCGGCUGCAG

GCCUUCCAGGGCUACCAAGUGACCAUGAAGACCGCCAAAGUGGCCGCCAG

CGACUGGACCUUCCUGCACUGCCUGCCCAGAAAGCCCGAAGAGGUGGACG

ACGAGGUGUUCUACAGCCCCCGGUCCCUGGUGUUUCCCGAGGCCGAGAAC

CGGAAGUGGACCAUCAUGGCUGUGAUGGUGUCUCUGCUGACCGACUACUC

CCCCCAGCUGCAGAAGCCCAAGUUCUGA

The following sequence (SEQ ID NO: 25) corresponds to a polyribonucleotide (e.g., RNA) sequence comprising human alpha globin UTR (SEQ ID NO: 12) and human codon-optimized OTC (SEQ ID NO: 4).

(SEQ ID NO: 25)

GGGAGACUCUUCUGGUCCCCACAGACUCAGAGAGAACGCCACCAUGCUGU

UCAACCUGCGGAUCCUGCUGAACAACGCCGCCUUCCGGAACGGCCACAAC

UUCAUGGUGCGCAACUUCAGAUGCGGCCAGCCCCUGCAGAACAAGGUGCA

GCUGAAGGGCAGGGACCUGCUGACCCUGAAGAACUUCACCGGCGAAGAGA

UCAAGUACAUGCUGUGGCUGAGCGCCGACCUGAAGUUCCGGAUCAAGCAG

AAGGGCGAGUACCUGCCCCUGCUGCAGGGCAAGUCUCUGGGCAUGAUCUU

CGAGAAGCGGAGCACCCGGACCCGGCUGUCUACCGAGACAGGAUUUGCCC

UGCUGGGCGGCCACCCUUGCUUUCUGACCACCCAGGAUAUCCACCUGGGC

GUGAACGAGAGCCUGACCGACACAGCCAGAGUGCUGAGCAGCAUGGCCGA

UGCCGUGCUGGCCAGAGUGUACAAGCAGAGCGACCUGGACACCCUGGCCA

AAGAGGCCAGCAUCCCCAUCAUCAACGGCCUGUCCGACCUGUACCACCCC

AUCCAGAUCCUGGCCGACUACCUGACCCUGCAGGAACACUACAGCUCCCU

GAAGGGCCUGACACUGAGCUGGAUCGGCGACGGCAACAACAUCCUGCACU

CUAUCAUGAUGAGCGCCGCCAAGUUCGGCAUGCAUCUGCAGGCCGCCACC

CCCAAGGGCUAUGAGCCUGAUGCCAGCGUGACCAAGCUGGCCGAGCAGUA

CGCCAAAGAGAAUGGCACCAAGCUGCUGCUGACCAACGACCCCCUGGAAG

CCGCCCAUGGCGGCAAUGUGCUGAUCACCGACACCUGGAUCAGCAUGGGC

CAGGAAGAGGAAAAGAAGAAGCGGCUGCAGGCCUUCCAGGGCUACCAAGU

GACCAUGAAGACCGCCAAAGUGGCCGCCAGCGACUGGACCUUCCUGCACU

GCCUGCCCAGAAAGCCCGAAGAGGUGGACGACGAGGUGUUCUACAGCCCC

CGGUCCCUGGUGUUUCCCGAGGCCGAGAACCGGAAGUGGACCAUCAUGGC

UGUGAUGGUGUCUCUGCUGACCGACUACUCCCCCCAGCUGCAGAAGCCCA

AGUUCUGA

The following sequence (SEQ ID NO: 26) corresponds to a polyribonucleotide (e.g., RNA) sequence comprising CYBA 5' UTR (SEQ ID NO: 20), human codon-optimized OTC (SEQ ID NO: 4) and CYBA 3' UTR (SEQ ID NO: 19).

(SEQ ID NO: 26)

GGGAGACcgcgccuagcagugucccagccgguucgugucgccGCCACCA

UGCUGUUCAACCUGCGGAUCCUGCUGAACAACGCCGCCUUCCGGAACGGC

CACAACUUCAUGGUGCGCAACUUCAGAUGCGGCCAGCCCCUGCAGAACAA

GGUGCAGCUGAAGGGCAGGGACCUGCUGACCCUGAAGAACUUCACCGGCG

AAGAGAUCAAGUACAUGCUGUGGCUGAGCGCCGACCUGAAGUUCCGGAUC

AAGCAGAAGGGCGAGUACCUGCCCCUGCUGCAGGGCAAGUCUCUGGGCAU

GAUCUUCGAGAAGCGGAGCACCCGGACCCGGCUGUCUACCGAGACAGGAU

UUGCCCUGCUGGGCGGCCACCCUUGCUUUCUGACCACCCAGGAUAUCCAC

CUGGGCGUGAACGAGAGCCUGACCGACACAGCCAGAGUGCUGAGCAGCAU

GGCCGAUGCCGUGCUGGCCAGAGUGUACAAGCAGAGCGACCUGGACACCC

UGGCCAAAGAGGCCAGCAUCCCCAUCAUCAACGGCCUGUCCGACCUGUAC

-continued

CACCCCAUCCAGAUCCUGGCCGACUACCUGACCCUGCAGGAACACUACAG

CUCCCUGAAGGGCCUGACACUGAGCUGGAUCGGCGACGGCAACAACAUCC

UGCACUCUAUCAUGAUGAGCGCCGCCAAGUUCGGCAUGCAUCUGCAGGCC

GCCACCCCCAAGGGCUAUGAGCCUGAUGCCAGCGUGACCAAGCUGGCCGA

GCAGUACGCCAAAGAGAACGGCACCAAGCUGCUGCUGACCAACGACCCUC

UGGAAGCCGCCCACGGCGGCAAUGUGCUGAUCACCGAUACCUGGAUCAGC

AUGGGCCAGGAAGAGGAAAAGAAGAAGCGGCUGCAGGCCUUCCAGGGCUA

CCAAGUGACCAUGAAGACCGCCAAAGUGGCCGCCAGCGACUGGACCUUCC

UGCACUGCCUGCCCAGAAAGCCCGAAGAGGUGGACGACGAGGUGUUCUAC

AGCCCCCGGUCCCUGGUGUUUCCCGAGGCCGAGAACCGGAAGUGGACCAU

CAUGGCUGUGAUGGUGUCUCUGCUGACCGACUACUCCCCCCAGCUGCAGA

AGCCCAAGUUCUGAccucgccccggaccugcccucccgccaggugcaccc accugcaaUaaaugcagcgaagccggga

The following sequence (SEQ ID NO: 27) corresponds to a polyribonucleotide (e.g., RNA) sequence comprising a TISU+T element (SEQ ID NO: 16) and human codon-optimized OTC (SEQ ID NO: 4).

(SEQ ID NO: 27)

GGGAGACUGCCAAGAUGCUGUUCAACCUGCGGAUCCUGCUGAACAACGCC

GCCUUCCGGAACGGCCACAACUUCAUGGUGCGCAACUUCAGAUGCGGCCA

GCCCCUGCAGAACAAGGUGCAGCUGAAGGGCAGGGACCUGCUGACCCUGA

AGAACUUCACCGGCGAAGAGAUCAAGUACAUGCUGUGGCUGAGCGCCGAC

CUGAAGUUCCGGAUCAAGCAGAAGGGCGAGUACCUGCCCCUGCUGCAGGG

-continued

CAAGUCUCUGGGCAUGAUCUUCGAGAAGCGGAGCACCCGGACCCGGCUGU

CUACCGAGACAGGAUUUGCCCUGCUGGGCGGCCACCCUUGCUUUCUGACC

ACCCAGGAUAUCCACCUGGGCGUGAACGAGAGCCUGACCGACACAGCCAG

AGUGCUGAGCAGCAUGGCCGAUGCCGUGCUGGCCAGAGUGUACAAGCAGA

GCGACCUGGACACCCUGGCCAAAGAGGCCAGCAUCCCCAUCAUCAACGGC

CUGUCCGACCUGUACCACCCCAUCCAGAUCCUGGCCGACUACCUGACCCU

GCAGGAACACUACAGCUCCCUGAAGGGCCUGACACUGAGCUGGAUCGGCG

ACGGCAACAACAUCCUGCACUCUAUCAUGAUGAGCGCCGCCAAGUUCGGC

-continued

AUGCAUCUGCAGGCCGCCACCCCCAAGGGCUAUGAGCCUGAUGCCAGCGU

GACCAAGCUGGCCGAGCAGUACGCCAAAGAGAACGGCACCAAGCUGCUGC

UGACCAACGACCCUCUGGAAGCCGCCCACGGCGGCAAUGUGCUGAUCACC

GAUACCUGGAUCAGCAUGGGCCAGGAAGAGGAAAAGAAGAAGCGGCUGCA

GGCCUUCCAGGGCUACCAAGUGACCAUGAAGACCGCCAAAGUGGCCGCCA

GCGACUGGACCUUCCUGCACUGCCUGCCCAGAAAGCCCGAAGAGGUGGAC

GACGAGGUGUUCUACAGCCCCCGGUCCCUGGUGUUUCCCGAGGCCGAGAA

CCGGAAGUGGACCAUCAUGGCUGUGAUGGUGUCUCUGCUGACCGACUACU

CCCCCCAGCUGCAGAAGCCCAAGUUCUGA

5. Further UTR Sequences

The following polyribonucleotide (e.g., RNA) sequence (SEQ ID NO: 28) corresponds to a 5' UTR derived from a-globin 5' UTR, referred to as HBA2 (NM_000517.4) with the transcription start site at position 30.

(SEQ ID NO: 28)

1 cauaaacccu ggcgcgcucg cgggccggca cucuucuggu ccccacagac 51 ucagagagaa cccacc

The following polyribonucleotide (e.g., RNA) sequence (SEQ ID NO: 29) corresponds to a 5' UTR derived from α-globin 5' UTR, referred to as ETH.

(SEQ ID NO: 29)

1 c ucuucugguc cccacagacu cagagagaac gccacc

The following polyribonucleotide (e.g., RNA) sequence (SEQ ID NO: 30) corresponds to hGH 3' UTR, as disclosed in WO 2012/170930.

(SEQ ID NO: 30)

1 CGGGUGGCAU CCCUGUGACC CCUCCCCAGU GCCUCUCCUG GCCCUGGAAG

51 UUGCCACUCC AGUGCCCACC AGCCUUGUCC UAAUAAAAUU AAGUUGCAUC

6. Specific Constructs (Promotor+UTRs+Coding Sequences)

The following sequence (SEQ ID NO: 31) corresponds to a polynucleotide (e.g., DNA) sequence comprising the T7 promoter and the human wildtype OTC (SEQ ID NO: 1) together with its natural 5' and 3' UTR. The start and stop codon is underlined.

(SEQ ID NO: 31)

TAATACGACTCACTATAGGGAGACAGCGGTGGAGCTTGGCATAAAGTTCA

AATGCTCCTACACCCTGCCCTGCAGTATCTCTAACCAGGGGACTTTGATA

AGGAAGCTGAAGGGTGATATTACCTTTGCTCCCTCACTGCAACTGAACAC

ATTTCTTAGTTTTTAGGTGGCCCCCGCTGGCTAACTTGCTGTGGAGTTTT

-continued

CAAGGGCATAGAATCGTCCTTTACACAATTAAAAGAAGATGCTGTTTAAT
CTGAGGATCCTGTTAAACAATGCAGCTTTTAGAAATGGTCACAACTTCAT
GGTTCGAAATTTTCGGTGTGGACAACCACTACAAAATAAAGTGCAGCTGA
AGGGCCGTGACCTTCTCACTCTAAAAAACTTTACCGGAGAAGAAATTAAA
TATATGCTATGGCTATCAGCAGATCTGAAATTTAGGATAAAACAGAAAGG
AGAGTATTTGCCTTTATTGCAAGGGAAGTCCTTAGGCATGATTTTTGAGA
AAAGAAGTACTCGAACAAGATTGTCTACAGAAACAGGCTTTGCACTTCTG
GGAGGACATCCTTGTTTTCTTACCACACAAGATATTCATTTGGGTGTGAA
TGAAAGTCTCACGGACACGGCCCGTGTATTGTCTAGCATGGCAGATGCAG
TATTGGCTCGAGTGTATAAACAATCAGATTTGGACACCCTGGCTAAAGAA
GCATCCATCCCAATTATCAATGGGCTGTCAGATTTGTACCATCCTATCCA
GATCCTGGCTGATTACCTCACGCTCCAGGAACACTATAGCTCTCTGAAAG
GTCTTACCCTCAGCTGGATCGGGGATGGGAACAATATCCTGCACTCCATC
ATGATGAGCGCAGCGAAATTCGGAATGCACCTTCAGGCAGCTACTCCAAA
GGGTTATGAGCCGGATGCTAGTGTAACCAAGTTGGCAGAGCAGTATGCCA
AAGAGAATGGTACCAAGCTGTTGCTGACAAATGATCCATTGGAAGCAGCG
CATGGAGGCAATGTATTAATTACAGACACTTGGATAAGCATGGGACAAGA
AGAGGAGAAGAAAAAGCGGCTCCAGGCTTTCCAAGGTTACCAGGTTACAA
TGAAGACTGCTAAAGTTGCTGCCTCTGACTGGACATTTTTACACTGCTTG
CCCAGAAAGCCAGAAGAAGTGGATGATGAAGTCTTTTATTCTCCTCGATC
ACTAGTGTTCCCAGAGGCAGAAAACAGAAAGTGGACAATCATGGCTGTCA
TGGTGTCCCTGCTGACAGATTACTCACCTCAGCTCCAGAAGCCTAAATTT
TGATGTTGTGTTACTTGTCAAGAAAGAAGCAATGTTCTTCAGTAACAGAA
TGAGTTGGTTTATGGGGAAAAGAGAAGAGAATCTAAAAAATAAACAAATC
CCTAACACGTGGTATGGGTGAACCGTATGATATGCTTTGCCATTGTGAAA
CTTTCCTTAAGCCTTTAATTTAAGTGCTGATGCACTGTAATACGTGCTTA
ACTTTGCTTAAACTCTCTAATTCCCAATTTCTGAGTTACATTTAGATATC
ATATTAATTATCATATACATTTACTTCAACATAAAATACTGTGTTCATAA
TGTATAATGTCTAAGCCATTAAGTGTAATCTATGCTTATTACCTAAATAA
ATTATCACCCATGCTAATTTA

The following sequence (SEQ ID NO: 32) corresponds to a polynucleotide (e.g., DNA) sequence comprising the T7 promoter, Minimal UTR and human wildtype OTC (SEQ ID NO: 1). The start and stop codon is underlined.

(SEQ ID NO: 32)
TAATACGACTCACTATAGGGAGACGCCACCATGCTGTTTAATCTGAGGAT
CCTGTTAAACAATGCAGCTTTTAGAAATGGTCACAACTTCATGGTTCGAA
ATTTTCGGTGTGGACAACCACTACAAAATAAAGTGCAGCTGAAGGGCCGT
GACCTTCTCACTCTAAAAAACTTTACCGGAGAAGAAATTAAATATATGCT
ATGGCTATCAGCAGATCTGAAATTTAGGATAAAACAGAAAGGAGAGTATT
TGCCTTTATTGCAAGGGAAGTCCTTAGGCATGATTTTTGAGAAAAGAAGT

-continued

ACTCGAACAAGATTGTCTACAGAAACAGGCTTTGCACTTCTGGGAGGACA
TCCTTGTTTTCTTACCACACAAGATATTCATTTGGGTGTGAATGAAAGTC
TCACGGACACGGCCCGTGTATTGTCTAGCATGGCAGATGCAGTATTGGCT
CGAGTGTATAAACAATCAGATTTGGACACCCTGGCTAAAGAAGCATCCAT
CCCAATTATCAATGGGCTGTCAGATTTGTACCATCCTATCCAGATCCTGG
CTGATTACCTCACGCTCCAGGAACACTATAGCTCTCTGAAAGGTCTTACC
CTCAGCTGGATCGGGGATGGGAACAATATCCTGCACTCCATCATGATGAG
CGCAGCGAAATTCGGAATGCACCTTCAGGCAGCTACTCCAAAGGGTTATG
AGCCGGATGCTAGTGTAACCAAGTTGGCAGAGCAGTATGCCAAAGAGAAT
GGTACCAAGCTGTTGCTGACAAATGATCCATTGGAAGCAGCGCATGGAGG
CAATGTATTAATTACAGACACTTGGATAAGCATGGGACAAGAAGAGGAGA
AGAAAAAGCGGCTCCAGGCTTTCCAAGGTTACCAGGTTACAATGAAGACT
GCTAAAGTTGCTGCCTCTGACTGGACATTTTTACACTGCTTGCCCAGAAA
GCCAGAAGAAGTGGATGATGAAGTCTTTTATTCTCCTCGATCACTAGTGT
TCCCAGAGGCAGAAAACAGAAAGTGGACAATCATGGCTGTCATGGTGTCC
CTGCTGACAGATTACTCACCTCAGCTCCAGAAGCCTAAATTTTGA

The following sequence (SEQ ID NO: 33) corresponds to a polynucleotide (e.g., DNA) sequence comprising the T7 promoter, human alpha globin UTR and human wildtype OTC (SEQ ID NO: 1). The start and stop codon is underlined.

(SEQ ID NO: 33)
TAATACGACTCACTATAGGGAGACTCTTCTGGTCCCCACAGACTCAGAG
AGAACGCCACCATGCTGTTTAATCTGAGGATCCTGTTAAACAATGCAGC
TTTTAGAAATGGTCACAACTTCATGGTTCGAAATTTTCGGTGTGGACAA
CCACTACAAAATAAAGTGCAGCTGAAGGGCCGTGACCTTCTCACTCTAA
AAAACTTTACCGGAGAAGAAATTAAATATATGCTATGGCTATCAGCAGA
TCTGAAATTTAGGATAAAACAGAAAGGAGAGTATTTGCCTTTATTGCAA
GGGAAGTCCTTAGGCATGATTTTTGAGAAAAGAAGTACTCGAACAAGAT
TGTCTACAGAAACAGGCTTTGCACTTCTGGGAGGACATCCTTGTTTTCT
TACCACACAAGATATTCATTTGGGTGTGAATGAAAGTCTCACGGACACG
GCCCGTGTATTGTCTAGCATGGCAGATGCAGTATTGGCTCGAGTGTATA
AACAATCAGATTTGGACACCCTGGCTAAAGAAGCATCCATCCCAATTAT
CAATGGGCTGTCAGATTTGTACCATCCTATCCAGATCCTGGCTGATTAC
CTCACGCTCCAGGAACACTATAGCTCTCTGAAAGGTCTTACCCTCAGCT
GGATCGGGGATGGGAACAATATCCTGCACTCCATCATGATGAGCGCAGC
GAAATTCGGAATGCACCTTCAGGCAGCTACTCCAAAGGGTTATGAGCCG
GATGCTAGTGTAACCAAGTTGGCAGAGCAGTATGCCAAAGAGAATGGTA
CCAAGCTGTTGCTGACAAATGATCCATTGGAAGCAGCGCATGGAGGCAA
TGTATTAATTACAGACACTTGGATAAGCATGGGACAAGAAGAGGAGAAG
AAAAAGCGGCTCCAGGCTTTCCAAGGTTACCAGGTTACAATGAAGACTG
CTAAAGTTGCTGCCTCTGACTGGACATTTTTACACTGCTTGCCCAGAAA

-continued

GCCAGAAGAAGTGGATGATGAAGTCTTTTATTCTCCTCGATCACTAGTG
TTCCCAGAGGCAGAAAACAGAAAGTGGACAATCATGGCTGTCATGGTGT
CCCTGCTGACAGATTACTCACCTCAGCTCCAGAAGCCTAAATTTTGA

The following sequence (SEQ ID NO: 34) corresponds to a polynucleotide (e.g., DNA) sequence comprising the T7 promoter, CYBA 5' UTR, human wildtype OTC (SEQ ID NO: 1) and CYBA 3' UTR. The start and stop codon is underlined.

(SEQ ID NO: 34)
TAATACGACTCACTATAGGGAGACCGCGCCTAGCAGTGTCCCAGCCGGG
TTCGTGTCGCCGCCACCATGCTGTTTAATCTGAGGATCCTGTTAAACAA
TGCAGCTTTTAGAAATGGTCACAACTTCATGGTTCGAAATTTTCGGTGT
GGACAACCACTACAAAATAAAGTGCAGCTGAAGGGCCGTGACCTTCTCA
CTCTAAAAAACTTTACCGGAGAAGAAATTAAATATATGCTATGGCTATC
AGCAGATCTGAAATTTAGGATAAAACAGAAAGGAGAGTATTTGCCTTTA
TTGCAAGGGAAGTCCTTAGGCATGATTTTTGAGAAAAGAAGTACTCGAA
CAAGATTGTCTACAGAAACAGGCTTTGCACTTCTGGGAGGACATCCTTG
TTTTCTTACCACACAAGATATTCATTTGGGTGTGAATGAAAGTCTCACG
GACACGGCCCGTGTATTGTCTAGCATGGCAGATGCAGTATTGGCTCGAG
TGTATAAACAATCAGATTTGGACACCCTGGCTAAAGAAGCATCCATCCC
AATTATCAATGGGCTGTCAGATTTGTACCATCCTATCCAGATCCTGGCT
GATTACCTCACGCTCCAGGAACACTATAGCTCTCTGAAAGGTCTTACCC
TCAGCTGGATCGGGGATGGGAACAATATCCTGCACTCCATCATGATGAG
CGCAGCGAAATTCGGAATGCACCTTCAGGCAGCTACTCCAAAGGGTTAT
GAGCCGGATGCTAGTGTAACCAAGTTGGCAGAGCAGTATGCCAAAGAGA
ATGGTACCAAGCTGTTGCTGACAAATGATCCATTGGAAGCAGCGCATGG
AGGCAATGTATTAATTACAGACACTTGGATAAGCATGGGACAAGAAGAG
GAGAAGAAAAAGCGGCTCCAGGCTTTCCAAGGTTACCAGGTTACAATGA
AGACTGCTAAAGTTGCTGCCTCTGACTGGACATTTTTACACTGCTTGCC
CAGAAAGCCAGAAGAAGTGGATGATGAAGTCTTTTATTCTCCTCGATCA
CTAGTGTTCCCAGAGGCAGAAAACAGAAAGTGGACAATCATGGCTGTCA
TGGTGTCCCTGCTGACAGATTACTCACCTCAGCTCCAGAAGCCTAAATT
TTGACCTCGCCCCGGACCTGCCCTCCCGCCAGGTGCACCCACCTGCAAT
AAATGCAGCGAAGCCGGGA

The following sequence (SEQ ID NO: 35) corresponds to a polynucleotide (e.g., DNA) sequence comprising the T7 promoter and the human codon optimized OTC (SEQ ID NO: 4) together with its natural 5' and 3' UTR. The start and stop codon is underlined.

(SEQ ID NO: 35)
TAATACGACTCACTATAGGGAGACAGCGGTGGAGCTTGGCATAAAGTTC
AAATGCTCCTACACCCTGCCCTGCAGTATCTCTAACCAGGGGACTTTGA
TAAGGAAGCTGAAGGGTGATATTACCTTTGCTCCCTCACTGCAACTGAA

-continued

CACATTTCTTAGTTTTTAGGTGGCCCCCGCTGGCTAACTTGCTGTGGAG
TTTTCAAGGGCATAGAATCGTCCTTTACACAATTAAAAGAAGATGCTGT
TCAACCTGCGGATCCTGCTGAACAACGCCGCCTTCCGGAACGGCCACAA
CTTCATGGTGCGCAACTTCAGATGCGGCCAGCCCCTGCAGAACAAGGTG
CAGCTGAAAGGCCGGGACCTGCTGACCCTGAAGAACTTCACCGGCGAAG
AGATCAAGTACATGCTGTGGCTGAGCGCCGACCTGAAGTTCCGGATCAA
GCAGAAGGGCGAGTACCTGCCCCTGCTGCAGGGAAAGTCCCTGGGCATG
ATCTTCGAGAAGCGGAGCACCCGGACCCGGCTGTCTACCGAGACAGGAT
TTGCCCTGCTGGGCGGCCACCCTTGCTTTCTGACCACCCAGGATATCCA
CCTGGGCGTGAACGAGAGCCTGACCGACACAGCCAGAGTGCTGAGCAGC
ATGGCCGATGCCGTGCTGGCCAGAGTGTACAAGCAGAGCGACCTGGACA
CCCTGGCCAAAGAGGCCAGCATCCCCATCATCAACGGCCTGTCCGACCT
GTACCACCCCATCCAGATCCTGGCCGACTACCTGACCCTGCAGGAACAC
TACAGCAGCCTGAAGGGCCTGACACTGAGCTGGATCGGCGACGGCAACA
ACATCCTGCACTCTATCATGATGAGCGCCGCCAAGTTCGGCATGCATCT
GCAGGCCGCCACCCCCAAGGGCTATGAGCCTGATGCCAGCGTGACCAAG
CTGGCCGAGCAGTACGCCAAAGAGAACGGCACCAAGCTGCTGCTGACCA
ACGACCCTCTGGAAGCCGCCCACGGCGGCAATGTGCTGATCACCGATAC
CTGGATCAGCATGGGCCAGGAAGAGGAAAAGAAGAAGCGGCTGCAGGCC
TTCCAGGGCTACCAAGTGACCATGAAGACCGCCAAAGTGGCCGCCAGCG
ACTGGACCTTCCTGCACTGCCTGCCCAGAAAGCCCGAAGAGGTGGACGA
CGAGGTGTTCTACAGCCCCCGGTCCCTGGTGTTTCCCGAGGCCGAGAAC
CGGAAGTGGACCATCATGGCTGTGATGGTGTCTCTGCTGACCGACTACT
CCCCCCAGCTGCAGAAACCCAAGTTCTGATGTTGTGTTACTTGTCAAGA
AAGAAGCAATGTTCTTCAGTAACAGAATGAGTTGGTTTATGGGGAAAAG
AGAAGAGAATCTAAAAAATAAACAAATCCCTAACACGTGGTATGGGTGA
ACCGTATGATATGCTTTGCCATTGTGAAACTTTCCTTAAGCCTTTAATT
TAAGTGCTGATGCACTGTAATACGTGCTTAACTTTGCTTAAACTCTCTA
ATTCCCAATTTCTGAGTTACATTTAGATATCATATTAATTATCATATAC
ATTTACTTCAACATAAAATACTGTGTTCATAATGTATAATGTCTAAGCC
ATTAAGTGTAATCTATGCTTATTACCTAAATAAATTATCACCCATGCTA
ATTTA

The following sequence (SEQ ID NO: 36) corresponds to a polynucleotide (e.g., DNA) sequence comprising the T7 promoter, Minimal UTR and human codon-optimized OTC (SEQ ID NO: 4). The start and stop codon is underlined.

(SEQ ID NO: 36)
TAATACGACTCACTATAGGGAGACGCCACCATGCTGTTCAACCTGCGGA
TCCTGCTGAACAACGCCGCCTTCCGGAACGGCCACAACTTCATGGTGCG
CAACTTCAGATGCGGCCAGCCCCTGCAGAACAAGGTGCAGCTGAAGGGC
AGGGACCTGCTGACCCTGAAGAACTTCACCGGCGAAGAGATCAAGTACA

-continued

TGCTGTGGCTGAGCGCCGACCTGAAGTTCCGGATCAAGCAGAAGGGCGA
GTACCTGCCCCTGCTGCAGGGCAAGTCTCTGGGCATGATCTTCGAGAAG
CGGAGCACCCGGACCCGGCTGTCTACCGAGACAGGATTTGCCCTGCTGG
GCGGCCACCCTTGCTTTCTGACCACCCAGGATATCCACCTGGGCGTGAA
CGAGAGCCTGACCGACACAGCCAGAGTGCTGAGCAGCATGGCCGATGCC
GTGCTGGCCAGAGTGTACAAGCAGAGCGACCTGGACACCCTGGCCAAAG
AGGCCAGCATCCCCATCATCAACGGCCTGTCCGACCTGTACCACCCCAT
CCAGATCCTGGCCGACTACCTGACCCTGCAGGAACACTACAGCTCCCTG
AAGGGCCTGACACTGAGCTGGATCGGCGACGGCAACAACATCCTGCACT
CTATCATGATGAGCGCCGCCAAGTTCGGCATGCATCTGCAGGCCGCCAC
CCCCAAGGGCTATGAGCCTGATGCCAGCGTGACCAAGCTGGCCGAGCAG
TACGCCAAAGAGAACGGCACCAAGCTGCTGCTGACCAACGACCCTCTGG
AAGCCGCCCACGGCGGCAATGTGCTGATCACCGATACCTGGATCAGCAT
GGGCCAGGAAGAGGAAAAGAAGAAGCGGCTGCAGGCCTTCCAGGGCTAC
CAAGTGACCATGAAGACCGCCAAAGTGGCCGCCAGCGACTGGACCTTCC
TGCACTGCCTGCCCAGAAAGCCCGAAGAGGTGGACGACGAGGTGTTCTA
CAGCCCCCGGTCCCTGGTGTTTCCCGAGGCCGAGAACCGGAAGTGGACC
ATCATGGCTGTGATGGTGTCTCTGCTGACCGACTACTCCCCCCAGCTGC
AGAAGCCCAAGTTCTGA

The following sequence (SEQ ID NO: 37) corresponds to a polynucleotide (e.g., DNA) sequence comprising the T7 promoter, human alpha globin UTR (SEQ ID NO: 12) and human codon-optimized OTC (SEQ ID NO: 4). The start and stop codon is underlined.

(SEQ ID NO: 37)

TAATACGACTCACTATAGGGAGACTCTTCTGGTCCCCACAGACTCAGAG
AGAACGCCACCATGCTGTTCAACCTGCGGATCCTGCTGAACAACGCCGC
CTTCCGGAACGGCCACAACTTCATGGTGCGCAACTTCAGATGCGGCCAG
CCCCTGCAGAACAAGGTGCAGCTGAAGGGCAGGGACCTGCTGACCCTGA
AGAACTTCACCGGCGAAGAGATCAAGTACATGCTGTGGCTGAGCGCCGA
CCTGAAGTTCCGGATCAAGCAGAAGGGCGAGTACCTGCCCCTGCTGCAG
GGCAAGTCTCTGGGCATGATCTTCGAGAAGCGGAGCACCCGGACCCGGC
TGTCTACCGAGACAGGATTTGCCCTGCTGGGCGGCCACCCTTGCTTTCT
GACCACCCAGGATATCCACCTGGGCGTGAACGAGAGCCTGACCGACACA
GCCAGAGTGCTGAGCAGCATGGCCGATGCCGTGCTGGCCAGAGTGTACA
AGCAGAGCGACCTGGACACCCTGGCCAAAGAGGCCAGCATCCCCATCAT
CAACGGCCTGTCCGACCTGTACCACCCCATCCAGATCCTGGCCGACTAC
CTGACCCTGCAGGAACACTACAGCTCCCTGAAGGGCCTGACACTGAGCT
GGATCGGCGACGGCAACAACATCCTGCACTCTATCATGATGAGCGCCGC
CAAGTTCGGCATGCATCTGCAGGCCGCCACCCCCAAGGGCTATGAGCCT
GATGCCAGCGTGACCAAGCTGGCCGAGCAGTACGCCAAAGAGAATGGCA
CCAAGCTGCTGCTGACCAACGACCCCCTGGAAGCCGCCCATGGCGGCAA

-continued

TGTGCTGATCACCGACACCTGGATCAGCATGGGCCAGGAAGAGGAAAAG
AAGAAGCGGCTGCAGGCCTTCCAGGGCTACCAAGTGACCATGAAGACCG
CCAAAGTGGCCGCCAGCGACTGGACCTTCCTGCACTGCCTGCCCAGAAA
GCCCGAAGAGGTGGACGACGAGGTGTTCTACAGCCCCCGGTCCCTGGTG
TTTCCCGAGGCCGAGAACCGGAAGTGGACCATCATGGCTGTGATGGTGT
CTCTGCTGACCGACTACTCCCCCCAGCTGCAGAAGCCCAAGTTCTGA

The following sequence (SEQ ID NO: 38) corresponds to a polynucleotide (e.g., DNA) sequence comprising the T7 promoter, CYBA 5' UTR, human codon-optimized OTC (SEQ ID NO: 4) and CYBA 3' UTR. The start and stop codon is underlined.

(SEQ ID NO: 38)

TAATACGACTCACTATAGGGAGACcgcgcctagcagtgtcccagccggg
ttcgtgtcgccGCCACCATGCTGTTCAACCTGCGGATCCTGCTGAACAA
CGCCGCCTTCCGGAACGGCCACAACTTCATGGTGCGCAACTTCAGATGC
GGCCAGCCCCTGCAGAACAAGGTGCAGCTGAAGGGCAGGGACCTGCTGA
CCCTGAAGAACTTCACCGGCGAAGAGATCAAGTACATGCTGTGGCTGAG
CGCCGACCTGAAGTTCCGGATCAAGCAGAAGGGCGAGTACCTGCCCCTG
CTGCAGGGCAAGTCTCTGGGCATGATCTTCGAGAAGCGGAGCACCCGGA
CCCGGCTGTCTACCGAGACAGGATTTGCCCTGCTGGGCGGCCACCCTTG
CTTTCTGACCACCCAGGATATCCACCTGGGCGTGAACGAGAGCCTGACC
GACACAGCCAGAGTGCTGAGCAGCATGGCCGATGCCGTGCTGGCCAGAG
TGTACAAGCAGAGCGACCTGGACACCCTGGCCAAAGAGGCCAGCATCCC
CATCATCAACGGCCTGTCCGACCTGTACCACCCCATCCAGATCCTGGCC
GACTACCTGACCCTGCAGGAACACTACAGCTCCCTGAAGGGCCTGACAC
TGAGCTGGATCGGCGACGGCAACAACATCCTGCACTCTATCATGATGAG
CGCCGCCAAGTTCGGCATGCATCTGCAGGCCGCCACCCCCAAGGGCTAT
GAGCCTGATGCCAGCGTGACCAAGCTGGCCGAGCAGTACGCCAAAGAGA
ACGGCACCAAGCTGCTGCTGACCAACGACCCTCTGGAAGCCGCCCACGG
CGGCAATGTGCTGATCACCGATACCTGGATCAGCATGGGCCAGGAAGAG
GAAAAGAAGAAGCGGCTGCAGGCCTTCCAGGGCTACCAAGTGACCATGA
AGACCGCCAAAGTGGCCGCCAGCGACTGGACCTTCCTGCACTGCCTGCC
CAGAAAGCCCGAAGAGGTGGACGACGAGGTGTTCTACAGCCCCCGGTCC
CTGGTGTTTCCCGAGGCCGAGAACCGGAAGTGGACCATCATGGCTGTGA
TGGTGTCTCTGCTGACCGACTACTCCCCCCAGCTGCAGAAGCCCAAGTT
CTGAcctcgccccggacctgccctcccgccaggtgcacccacctgcaat
aaatgcagcgaagccggga The following sequence (SEQ ID NO: 39) corresponds to a polynucleotide (e.g., DNA) sequence comprising the T7 promoter, a TISU+T element and human codon-optimized OTC (SEQ ID NO: 4). The start and stop codon is underlined.

(SEQ ID NO: 39)
TAATACGACTCACTATAGGGAGACTGCCAAGATGCTGTTCAACCTGCGG

ATCCTGCTGAACAACGCCGCCTTCCGGAACGGCCACAACTTCATGGTGC

GCAACTTCAGATGCGGCCAGCCCCTGCAGAACAAGGTGCAGCTGAAGGG

CAGGGACCTGCTGACCCTGAAGAACTTCACCGGCGAAGAGATCAAGTAC

ATGCTGTGGCTGAGCGCCGACCTGAAGTTCCGGATCAAGCAGAAGGGCG

AGTACCTGCCCCTGCTGCAGGGCAAGTCTCTGGGCATGATCTTCGAGAA

GCGGAGCACCCGGACCCGGCTGTCTACCGAGACAGGATTTGCCCTGCTG

GGCGGCCACCCTTGCTTTCTGACCACCCAGGATATCCACCTGGGCGTGA

ACGAGAGCCTGACCGACACAGCCAGAGTGCTGAGCAGCATGGCCGATGC

CGTGCTGGCCAGAGTGTACAAGCAGAGCGACCTGGACACCCTGGCCAAA

GAGGCCAGCATCCCCATCATCAACGGCCTGTCCGACCTGTACCACCCCA

TCCAGATCCTGGCCGACTACCTGACCCTGCAGGAACACTACAGCTCCCT

GAAGGGCCTGACACTGAGCTGGATCGGCGACGGCAACAACATCCTGCAC

TCTATCATGATGAGCGCCGCCAAGTTCGGCATGCATCTGCAGGCCGCCA

CCCCCAAGGGCTATGAGCCTGATGCCAGCGTGACCAAGCTGGCCGAGCA

GTACGCCAAAGAGAACGGCACCAAGCTGCTGCTGACCAACGACCCTCTG

GAAGCCGCCCACGGCGGCAATGTGCTGATCACCGATACCTGGATCAGCA

TGGGCCAGGAAGAGGAAAAGAAGAAGCGGCTGCAGGCCTTCCAGGGCTA

CCAAGTGACCATGAAGACCGCCAAAGTGGCCGCCAGCGACTGGACCTTC

CTGCACTGCCTGCCCAGAAAGCCCGAAGAGGTGGACGACGAGGTGTTCT

ACAGCCCCCGGTCCCTGGTGTTTCCCGAGGCCGAGAACCGGAAGTGGAC

CATCATGGCTGTGATGGTGTCTCTGCTGACCGACTACTCCCCCCAGCTG

CAGAAGCCCAAGTTCTGA

The following polynucleotide (e.g., DNA) sequence (SEQ ID NO: 40) corresponds to a 5' UTR referred to as Minimal.

(SEQ ID NO: 40)
1 GGGAGACGCC ACC

The following polynucleotide (e.g., DNA) sequence (SEQ ID NO: 41) corresponds to a 5' UTR referred to as hAg, a 5' UTR derived from human alpha globin.

(SEQ ID NO: 41)
1 GGGAGACTCT TCTGGTCCCC ACAGACTCAG AGAGAACGCC ACC

The following polynucleotide (e.g., DNA) sequence (SEQ ID NO: 42) corresponds to a 5' UTR referred to as TISU.

(SEQ ID NO: 42)
1 GGGAGACGCC AAG

The following polynucleotide (e.g., DNA) sequence (SEQ ID NO: 43) corresponds to a 5' UTR referred to as TISU+T.

(SEQ ID NO: 43)
1 GGGAGACTGC CAAG

The following polynucleotide (e.g., DNA) sequence (SEQ ID NO: 44) shows the hOTC-STOP-RNA construct with the T7 promoter followed by a human alpha globin 5' UTR. The mutated start codon is shown in bold; the natural stop codon is shown in italics and the artificially created stop codons are underlined.

SEQ ID NO: 44)
TAATACGACTCACTATAGGGAGACTCTTCTGGTCCCCACAGACTCAGAG

AGAACCGCCCGTGACTGTTCAACCTGCGGATCCTGCTGAACAACGCCGC

CTTCCGGAACGGCCACAACTTCTGAGTGCGCAACTTCAGTGACGGCCAG

CCCCTGCAGAACAAGGTGCAGCTGAAGGGCAGGGACCTGCTGACCCTGA

AGAACTTCACCGGCGAAGAGATCAAGTACTGACTGTGGCTGAGCGCCGA

CCTGAAGTTCCGGATCAAGCAGAAGGGCGAGTACCTGCCCCTGCTGCAG

GGCAAGTCTCTGGGCTGAATCTTCGAGAAGCGGAGCACCCGGACCCGGC

TGTCTACCGAGACAGGATTTGCCCTGCTGGGCGGCCACCCTTGCTTTCT

GACCACCCAGGATATCCACCTGGGCGTGAACGAGAGCCTGACCGACACA

GCCAGAGTGCTGAGCAGCTGAGCCGTGACCGTGCTGGCCAGAGTGTACA

AGCAGAGCGACCTGGACACCCTGGCCAAAGAGGCCAGCATCCCCATCAT

CAACGGCCTGTCCGACCTGTACCACCCCATCCAGATCCTGGCCGACTAC

CTGACCCTGCAGGAACACTACAGCTCCCTGAAGGGCCTGACACTGAGCT

GGATCGGCGACGGCAACAACATCCTGCACTCTATCTGATGAAGCGCCGC

CAAGTTCGGCTGACATCTGCAGGCCGCCACCCCCAAGGGCTTGAAGCCT

GTGACCAGCGTGACCAAGCTGGCCGAGCAGTACGCCAAAGAGAACGGCA

CCAAGCTGCTGCTGACCAACGACCCTCTGGAAGCCGCCCACGGCGGCAT

GATGCTGATCACCGATACCTGGATCAGCTGAGGCCAGGAAGAGGAAAAG

AAGAAGCGGCTGCAGGCCTTCCAGGGCTACCAAGTGACCATGAAGACCG

CCAAAGTGGCCGCCAGCGACTGGACCTTCCTGCACTGCCTGCCCAGAAA

GCCCGAAGAGGTGGACGACGAGGTGTTCTACAGCCCCCGGTCCCTGGTG

TTTCCCGAGGCCGAGAACCGGAAGTGGACCATCTGAGCTGTGTGAGTGT

CTCTGCTGACCGACTACTCCCCCCAGCTGCAGAAGCCCAAGTTC*TGA*

The following polynucleotide (e.g., DNA) sequence (SEQ ID NO: 45) corresponds to the codon optimized ORF from the murine OTC sequence (NM_008769.4) from NCBI Database flanked by a minimal 5' UTR (T7-mOTCORF (CO); Start and stop codon is underlined (SEQ ID NO: 45)
TAATACGACTCACTATAGGGAGACGCCACCATGCTGAGCAACCTGAGAA

TCCTGCTGAACAACGCCGCCCTGAGAAAGGGCCACACAAGCGTCGTGCG

GCACTTTTGGTGCGGCAAGCCTGTGCAGAGCCAGGTGCAGCTGAAGGGC

AGGGACCTGCTGACCCTGAAGAACTTCACCGGCGAAGAGATCCAGTACA

TGCTGTGGCTGAGCGCCGACCTGAAGTTCAGAATCAAGCAGAAGGGCGA

GTACCTGCCCCTGCTGCAGGGCAAGTCTCTGGGCATGATCTTCGAGAAG

AGAAGCACCAGAACCAGGCTGAGCACCGAGACAGGCTTCGCTCTGCTGG

GCGGCCACCCTAGCTTTCTGACCACCCAGGATATCCACCTGGGCGTGAA

CGAGAGCCTGACCGACACAGCCAGAGTGCTGAGCAGCATGACCGATGCC

GTGCTGGCCAGAGTGTACAAGCAGTCCGACCTGGACACCCTGGCCAAAG

-continued

AGGCCAGCATCCCCATCGTGAACGGCCTGAGCGACCTGTACCACCCCAT

CCAGATCCTGGCCGACTACCTGACCCTGCAGGAACACTACGGCTCCCTG

AAGGGCCTGACACTGAGCTGGATCGGCGACGGCAACAACATCCTGCACT

CTATCATGATGAGCGCCGCCAAGTTCGGCATGCATCTGCAGGCCGCTAC

CCCCAAGGGCTACGAGCCAGACCCCAACATCGTGAAGCTGGCCGAGCAG

TACGCCAAAGAGAACGGCACCAAGCTGAGCATGACCAACGACCCCCTGG

AAGCCGCTAGAGGCGGCAACGTGCTGATCACCGACACCTGGATCAGCAT

GGGCCAGGAAGATGAGAAGAAGAAGAGACTGCAGGCCTTCCAGGGCTAC

CAAGTGACCATGAAGACCGCCAAGGTGGCCGCTAGCGACTGGACCTTCC

TGCACTGCCTGCCCAGAAAGCCCGAAGAGGTGGACGACGAGGTGTTCTA

CAGCCCTAGAAGCCTGGTGTTCCCCGAGGCCGAGAACAGAAAGTGGACC

ATCATGGCTGTGATGGTGTCTCTGCTGACCGACTACTCCCCCGTGCTGC

AGAAGCCCAAGTTCTGA

The following polyribonucleotide (e.g., RNA) sequence (SEQ ID NO: 46) corresponds to the RNA sequence which results from transcription of the DNA sequence shown in SEQ ID NO: 45 showing the codon optimized ORF from the murine OTC sequence (NM_008769.4) from NCBI Database flanked by a minimal 5' UTR (T7-mOTCORF(CO); Start and stop codon is underlined

GGGAGACGCCACCAUGCUGAGCAACCUGAGAAUCCUGCUGAACAACGCC

GCCCUGAGAAAGGGCCACACAAGCGUCGUGCGGCACUUUUGGUGCGGCA

AGCCUGUGCAGAGCCAGGUGCAGCUGAAGGGCAGGGACCUGCUGACCCU

GAAGAACUUCACCGGCGAAGAGAUCCAGUACAUGCUGUGGCUGAGCGCC

-continued

GACCUGAAGUUCAGAAUCAAGCAGAAGGGCGAGUACCUGCCCCUGCUGC

AGGGCAAGUCUCUGGGCAUGAUCUUCGAGAAGAGAAGCACCAGAACCAG

GCUGAGCACCGAGACAGGCUUCGCUCUGCUGGGCGGCCACCCUAGCUUU

CUGACCACCCAGGAUAUCCACCUGGGCGUGAACGAGAGCCUGACCGACA

CAGCCAGAGUGCUGAGCAGCAUGACCGAUGCCGUGCUGGCCAGAGUGUA

CAAGCAGUCCGACCUGGACACCCUGGCCAAAGAGGCCAGCAUCCCCAUC

GUGAACGGCCUGAGCGACCUGUACCACCCCAUCCAGAUCCUGGCCGACU

ACCUGACCCUGCAGGAACACUACGGCUCCCUGAAGGGCCUGACACUGAG

CUGGAUCGGCGACGGCAACAACAUCCUGCACUCUAUCAUGAUGAGCGCC

GCCAAGUUCGGCAUGCAUCUGCAGGCCGCUACCCCCAAGGGCUACGAGC

CAGACCCCAACAUCGUGAAGCUGGCCGAGCAGUACGCCAAAGAGAACGG

CACCAAGCUGAGCAUGACCAACGACCCCCUGGAAGCCGCUAGAGGCGGC

AACGUGCUGAUCACCGACACCUGGAUCAGCAUGGGCCAGGAAGAUGAGA

AGAAGAAGAGACUGCAGGCCUUCCAGGGCUACCAAGUGACCAUGAAGAC

CGCCAAGGUGGCCGCUAGCGACUGGACCUUCCUGCACUGCCUGCCCAGA

AAGCCCGAAGAGGUGGACGACGAGGUGUUCUACAGCCCUAGAAGCCUGG

UGUUCCCCGAGGCCGAGAACAGAAAGUGGACCAUCAUGGCUGUGAUGGU

GUCUCUGCUGACCGACUACUCCCCCGUGCUGCAGAAGCCCAAGUUCUGA

The following polynucleotide (e.g., DNA) sequence (SEQ ID NO: 47) corresponds to a 5' UTR referred to as CYBA.

(SEQ ID NO: 47)

1 GGGAGACCGC GCCTAGCAGT GTCCCAGCCG GGTTCGTGTC

GCCGCCACC

The invention claimed is:

1. A modified polyribonucleotide comprising a primary sequence which is at least 95% identical to SEQ ID NO: 4 and which encodes an ornithine transcarbamylase (OTC) protein, wherein the modified polyribonucleotide contains a combination of unmodified and modified ribonucleotides, wherein 30-50% of the uridines are analogs of uridine and 5-30% of the cytidines are analogs of cytidine.

2. The modified polyribonucleotide of claim 1, wherein the modified polyribonucleotide contains a combination of unmodified and modified ribonucleotides, wherein 30-45% of the uridines are analogs of uridine and 5-20% of the cytidines are analogs of cytidine; or wherein the modified polyribonucleotide is made using an input mixture of ribonucleotides, wherein 30-45% of the uridines are analogs of uridine and 5-20% of the cytidines are analogs of cytidine.

3. The modified polyribonucleotide of claim 1, wherein the modified polyribonucleotide is codon-optimized for expression in mammalian cells.

4. The modified polyribonucleotide of claim 1, wherein the modified polyribonucleotide further comprises a 3' UTR, a 5' UTR, or a 3' UTR and a 5' UTR, and wherein the UTR(s) aid(s) in enhancing expression of an ornithine transcarbamylase (OTC) protein in cells.

5. The modified polyribonucleotide of claim 4, wherein the 5' UTR comprises SEQ ID NO: 13, wherein the ribonucleotides of the 5' UTR are positioned upstream (5') of the ribonucleotides encoding the ornithine transcarbamylase (OTC) protein, and 3' from ribonucleotides corresponding to a portion of a promoter sequence.

6. The modified polyribonucleotide of claim 5, wherein the ribonucleotides of the 5' UTR are directly 3' from ribonucleotides corresponding to a portion of the promoter without any intervening nucleotides;

wherein the 5' UTR and the portion of a promoter together consist essentially of SEQ ID NO: 12.

7. The modified polyribonucleotide of claim 4, wherein the 3' UTR comprises one or more copies of a 3' UTR sequence of SEQ ID NO: 19, wherein the ribonucleotides of the 3' UTR are positioned downstream (3') of the ribonucleotides encoding the ornithine transcarbamylase (OTC) protein.

8. The modified polyribonucleotide of claim 7, wherein the 3' UTR comprises one copy or two copies of SEQ ID NO: 19.

9. The modified polyribonucleotide of claim 4, wherein the modified polyribonucleotide further comprises a portion of a promoter sequence, wherein the ribonucleotides of the portion of a promoter sequence are positioned upstream (5') of the ribonucleotides of the 5' UTR and/or ornithine transcarbamylase (OTC) coding sequence(s).

10. The modified polyribonucleotide of claim 9, wherein the promoter sequence is selected from the group consisting of SEQ ID NOs: 6-9 (either including or excluding sequence upstream from the transcription start site); and/or wherein the portion of the promoter sequence corresponds to a region transcribed by a DNA-dependent RNA-polymerase.

11. The polyribonucleotide of claim 1, wherein the polyribonucleotide further comprises at least one 5' cap structure.

12. The polyribonucleotide of claim 1, wherein the polyribonucleotide further comprises a polyA tail at the 3' end of the polyribonucleotide, and wherein the polyA tail comprises at least 100 bases.

13. The modified polyribonucleotide of claim 1, wherein the modified polyribonucleotide is translated more efficiently in cells of a subject as compared to an unmodified polyribonucleotide having the same primary sequence as the modified polyribonucleotide;

wherein the modified polyribonucleotide has enhanced stability in cells of a subject as compared to the stability of an unmodified polyribonucleotide having the same primary sequence as the modified polyribonucleotide; or wherein the modified polyribonucleotide has diminished immunogenicity as compared to the immunogenicity of an unmodified polyribonucleotide having the same primary sequence as the modified polyribonucleotide.

14. A composition comprising the polyribonucleotide of claim 1, formulated with one or more pharmaceutically acceptable carriers and/or excipients.

15. The composition of claim 14, wherein the modified polyribonucleotide is formulated in a nanoparticle or nanocapsule.

16. The modified polyribonucleotide or composition of claim 1, wherein the uridine analogs are selected from the group consisting of pseudouridine, 2-thiouridine, 5-iodouridine, and 5-methyluridine; and/or wherein the cytidine analogs are selected from the group consisting of 5-methylcytidine, 2'-amino-2'-deoxycytidine, 2'-fluoro-2'-deoxycytidine, and 5-iodocytidine.

17. A method of treating ornithine transcarbamylase (OTC) deficiency comprising administering to a patient in need thereof a polyribonucleotide of claim 1.

18. A method of decreasing plasma ammonia levels in a subject in need thereof, comprising administering to said subject a polyribonucleotide of claim 1.

* * * * *

SEQUENCE LISTING

```
<160> NUMBER OF SEQ ID NOS: 61

<210> SEQ ID NO 1
<211> LENGTH: 1065
<212> TYPE: RNA
<213> ORGANISM: Homo sapiens

<400> SEQUENCE: 1

augcuguuua aucugaggau ccuguuaaac aaugcagcuu uuagaaaugg ucacaacuuc     60

augguucgaa auuuucggug uggacaacca cuacaaaaua aagugcagcu gaagggccgu    120

gaccuucuca cucuaaaaaa cuuuaccgga gaagaaauua aauauaugcu auggcuauca    180

gcagaucuga aauuuaggau aaaacagaaa ggagaguauu ugccuuuauu gcaagggaag    240

uccuuaggca ugauuuuuga gaaaagaagu acucgaacaa gauugucuac agaaacaggc    300

uuugcacuuc ugggaggaca uccuuguuuu cuuaccacac aagauauuca uuugggugug    360

aaugaaaguc ucacggacac ggcccgugua uugucuagca uggcagaugc aguauuggcu    420

cgaguguaua aacaaucaga uuuggacacc cuggcuaaag aagcauccau cccaauuauc    480

aaugggcugu cagauuugua ccauccuauc cagauccugg cugauuaccu cacgcuccag    540

gaacacuaua gcucucugaa aggucuuacc cucagcugga ucggggaugg gaacaauauc    600
```

-continued

```
cugcacucca ucaugaugag cgcagcgaaa uucggaaugc accuucaggc agcuacucca    660

aaggguuaug agccggaugc uaguguaacc aaguuggcag agcaguaugc caaagagaau    720

gguaccaagc uguugcugac aaaugaucca uuggaagcag cgcauggagg caauguauua    780

auuacagaca cuuggauaag caugggacaa gaagaggaga agaaaaagcg gcuccaggcu    840

uuccaagguu accagguuac aaugaagacu gcuaaaguug cugccucuga cuggacauuu    900

uuacacugcu ugcccagaaa gccagaagaa guggaugaug aagucuuuua uucuccucga    960

ucacuagugu ucccagaggc agaaaacaga aaguggacaa ucauggcugu cauggugucc   1020

cugcugacag auuacucacc ucagcuccag aagccuaaau uuuga                   1065


<210> SEQ ID NO 2
<211> LENGTH: 1065
<212> TYPE: DNA
<213> ORGANISM: Homo sapiens

<400> SEQUENCE: 2

atgctgttta atctgaggat cctgttaaac aatgcagctt ttagaaatgg tcacaacttc     60

atggttcgaa attttcggtg tggacaacca ctacaaaata aagtgcagct gaagggccgt    120

gaccttctca ctctaaaaaa ctttaccgga gaagaaatta aatatatgct atggctatca    180

gcagatctga aatttaggat aaaacagaaa ggagagtatt tgcctttatt gcaagggaag    240

tccttaggca tgatttttga gaaaagaagt actcgaacaa gattgtctac agaaacaggc    300

tttgcacttc tgggaggaca tccttgtttt cttaccacac aagatattca tttgggtgtg    360

aatgaaagtc tcacggacac ggcccgtgta ttgtctagca tggcagatgc agtattggct    420

cgagtgtata aacaatcaga tttggacacc ctggctaaag aagcatccat cccaattatc    480

aatgggctgt cagatttgta ccatcctatc cagatcctgg ctgattacct cacgctccag    540

gaacactata gctctctgaa aggtcttacc ctcagctgga tcggggatgg gaacaatatc    600

ctgcactcca tcatgatgag cgcagcgaaa ttcggaatgc accttcaggc agctactcca    660

aagggttatg agccggatgc tagtgtaacc aagttggcag agcagtatgc caaagagaat    720

ggtaccaagc tgttgctgac aaatgatcca ttggaagcag cgcatggagg caatgtatta    780

attacagaca cttggataag catgggacaa gaagaggaga agaaaaagcg gctccaggct    840

ttccaaggtt accaggttac aatgaagact gctaaagttg ctgcctctga ctggacattt    900

ttacactgct tgcccagaaa gccagaagaa gtggatgatg aagtctttta ttctcctcga    960

tcactagtgt tcccagaggc agaaaacaga aagtggacaa tcatggctgt catggtgtcc   1020

ctgctgacag attactcacc tcagctccag aagcctaaat tttga                   1065


<210> SEQ ID NO 3
<211> LENGTH: 354
<212> TYPE: PRT
<213> ORGANISM: Homo sapiens

<400> SEQUENCE: 3

Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
    50                  55                  60
```

```
Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
    130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu
    210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
            260                 265                 270

Glu Lys Lys Lys Arg Leu Gln Ala Phe Gln Gly Tyr Gln Val Thr Met
        275                 280                 285

Lys Thr Ala Lys Val Ala Ala Ser Asp Trp Thr Phe Leu His Cys Leu
    290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
            340                 345                 350

Lys Phe
```

<210> SEQ ID NO 4
<211> LENGTH: 1065
<212> TYPE: RNA
<213> ORGANISM: Artificial Sequence
<220> FEATURE:
<223> OTHER INFORMATION: The following polyribonucleotide (e.g., RNA) sequence (SEQ ID NO: 4) encodes wildtype human ornithine transcarbamylase (OTC) but is codon-optimized (the signal peptide for mitochondrial import ranges from position 1 to position 95)

<400> SEQUENCE: 4

```
augcuguuca accugcggau ccugcugaac aacgccgccu uccggaacgg ccacaacuuc     60

auggugcgca acuucagaug cggccagccc cugcagaaca aggugcagcu gaagggcagg    120

gaccugcuga cccugaagaa cuucaccggc gaagagauca aguacaugcu guggcugagc    180

gccgaccuga aguuccggau caagcagaag ggcgaguacc ugccccugcu gcagggcaag    240

ucucugggca ugaucuucga gaagcggagc acccggaccc ggcugucuac cgagacagga    300
```

uuugcccugc ugggcggcca cccuugcuuu cugaccaccc aggauaucca ccugggcgug 360
aacgagagcc ugaccgacac agccagagug cugagcagca uggccgaugc cgugcuggcc 420
agaguguaca agcagagcga ccuggacacc cuggccaaag aggccagcau ccccaucauc 480
aacggccugu ccgaccugua ccaccccauc cagauccugg ccgacuaccu gacccugcag 540
gaacacuaca gcucccugaa gggccugaca cugagcugga ucggcgacgg caacaacauc 600
cugcacucua ucaugaugag cgccgccaag uucggcaugc aucugcaggc cgccaccccc 660
aagggcuaug agccugaugc cagcgugacc aagcuggccg agcaguacgc caaagagaac 720
ggcaccaagc ugcugcugac caacgacccu cuggaagccg cccacggcgg caaugugcug 780
aucaccgaua ccuggaucag caugggccag gaagaggaaa agaagaagcg gcugcaggcc 840
uuccagggcu accaagugac caugaagacc gccaaagugg ccgccagcga cuggaccuuc 900
cugcacugcc ugcccagaaa gcccgaagag guggacgacg agguguucua cagcccccgg 960
ucccuggugu uucccgaggc cgagaaccgg aaguggacca ucauggcugu gauggugucu 1020
cugcugaccg acuacucccc ccagcugcag aagcccaagu ucuga 1065

<210> SEQ ID NO 5
<211> LENGTH: 1065
<212> TYPE: DNA
<213> ORGANISM: Artificial Sequence
<220> FEATURE:
<223> OTHER INFORMATION: The following nucleotide (e.g., DNA) sequence (SEQ ID NO: 5) encodes wildtype human ornithine transcarbamylase (OTC) but is codon-optimized (the signal peptide for mitochondrial import ranges from position 1 to position 95)

<400> SEQUENCE: 5
atgctgttca acctgcggat cctgctgaac aacgccgcct tccggaacgg ccacaacttc 60
atggtgcgca acttcagatg cggccagccc ctgcagaaca aggtgcagct gaagggcagg 120
gacctgctga ccctgaagaa cttcaccggc gaagagatca agtacatgct gtggctgagc 180
gccgacctga agttccggat caagcagaag ggcgagtacc tgcccctgct gcagggcaag 240
tctctgggca tgatcttcga gaagcggagc acccggaccc ggctgtctac cgagacagga 300
tttgccctgc tgggcggcca cccttgcttt ctgaccaccc aggatatcca cctgggcgtg 360
aacgagagcc tgaccgacac agccagagtg ctgagcagca tggccgatgc cgtgctggcc 420
agagtgtaca agcagagcga cctggacacc ctggccaaag aggccagcat ccccatcatc 480
aacggcctgt ccgacctgta ccaccccatc cagatcctgg ccgactacct gaccctgcag 540
gaacactaca gctccctgaa gggcctgaca ctgagctgga tcggcgacgg caacaacatc 600
ctgcactcta tcatgatgag cgccgccaag ttcggcatgc atctgcaggc cgccaccccc 660
aagggctatg agcctgatgc cagcgtgacc aagctggccg agcagtacgc caaagagaac 720
ggcaccaagc tgctgctgac caacgaccct ctggaagccg cccacggcgg caatgtgctg 780
atcaccgata cctggatcag catgggccag gaagaggaaa agaagaagcg gctgcaggcc 840
ttccagggct accaagtgac catgaagacc gccaaagtgg ccgccagcga ctggaccttc 900
ctgcactgcc tgcccagaaa gcccgaagag gtggacgacg aggtgttcta cagcccccgg 960
tccctggtgt ttcccgaggc cgagaaccgg aagtggacca tcatggctgt gatggtgtct 1020
ctgctgaccg actactcccc ccagctgcag aagcccaagt tctga 1065

<210> SEQ ID NO 6
<211> LENGTH: 23

<212> TYPE: RNA
<213> ORGANISM: Artificial Sequence
<220> FEATURE:
<223> OTHER INFORMATION: The following polyribonucleotide (e.g., RNA) sequence (SEQ ID NO: 6) corresponds to a T7 promoter sequence. The G at position 18 denotes the transcription start site

<400> SEQUENCE: 6
uaauacgacu cacuauaggg aga 23

<210> SEQ ID NO 7
<211> LENGTH: 23
<212> TYPE: RNA
<213> ORGANISM: Artificial Sequence
<220> FEATURE:
<223> OTHER INFORMATION: The following polyribonucleotide (e.g., RNA) sequence (SEQ ID NO: 7) corresponds to a T3 promoter sequence. The G at position 18 denotes the transcription start site

<400> SEQUENCE: 7
aauuaacccu cacuaaaggg aga 23

<210> SEQ ID NO 8
<211> LENGTH: 21
<212> TYPE: RNA
<213> ORGANISM: Artificial Sequence
<220> FEATURE:
<223> OTHER INFORMATION: The following polyribonucleotide (e.g., RNA) sequence (SEQ ID NO: 8) corresponds to a SP6 promoter sequence. The G at position 18 denotes the transcription start site

<400> SEQUENCE: 8
auuuagguga cacuauagaa g 21

<210> SEQ ID NO 9
<211> LENGTH: 21
<212> TYPE: RNA
<213> ORGANISM: Artificial Sequence
<220> FEATURE:
<223> OTHER INFORMATION: The following polyribonucleotide sequence (e.g., RNA) corresponds to a K11 promoter sequence. The G at position 18 denotes the transcription start site

<400> SEQUENCE: 9
aauuagggca cacuauaggg a 21

<210> SEQ ID NO 10
<211> LENGTH: 13
<212> TYPE: RNA
<213> ORGANISM: Artificial Sequence
<220> FEATURE:
<223> OTHER INFORMATION: The following polyribonucleotide (e.g., RNA) sequence (SEQ ID NO: 10) corresponds to a 5' UTR referred to as Minimal (with the 3' part of the T7 promoter sequence)

<400> SEQUENCE: 10
gggagacgcc acc 13

<210> SEQ ID NO 11
<211> LENGTH: 7
<212> TYPE: RNA
<213> ORGANISM: Artificial Sequence
<220> FEATURE:
<223> OTHER INFORMATION: The following polyribonucleotide (e.g., RNA) sequence (SEQ ID NO: 11) corresponds to a 5' UTR referred to as Minimal

<400> SEQUENCE: 11 cgccacc 7

<210> SEQ ID NO 12
<211> LENGTH: 43
<212> TYPE: RNA
<213> ORGANISM: Artificial Sequence
<220> FEATURE:
<223> OTHER INFORMATION: The following polyribonucleotide (e.g., RNA) sequence (SEQ ID NO: 12) corresponds to a 5' UTR referred to as hAg, a 5' UTR derived from human alpha globin (with the 3' part of the T7 promoter sequence)

<400> SEQUENCE: 12
gggagacucu ucuggucccc acagacucag agagaacgcc acc 43

<210> SEQ ID NO 13
<211> LENGTH: 37
<212> TYPE: RNA
<213> ORGANISM: Artificial Sequence
<220> FEATURE:
<223> OTHER INFORMATION: The following polyribonucleotide (e.g., RNA) sequence (SEQ ID NO: 13) corresponds to a 5' UTR referred to as hAg, a 5' UTR derived from human alpha globin, without promoter sequence

<400> SEQUENCE: 13
cucuucuggu ccccacagac ucagagagaa cgccacc 37

<210> SEQ ID NO 14
<211> LENGTH: 13
<212> TYPE: RNA
<213> ORGANISM: Artificial Sequence
<220> FEATURE:
<223> OTHER INFORMATION: The following polyribonucleotide (e.g., RNA) sequence (SEQ ID NO: 14) corresponds to a 5' UTR referred to as TISU (with the 3' part of the T7 promoter sequence)

<400> SEQUENCE: 14
gggagacgcc aag 13

<210> SEQ ID NO 15
<211> LENGTH: 6
<212> TYPE: RNA
<213> ORGANISM: Artificial Sequence
<220> FEATURE:
<223> OTHER INFORMATION: The following polyribonucleotide (e.g., RNA) sequence (SEQ ID NO: 15) corresponds to a 5' UTR referred to as TISU, without promoter sequence

<400> SEQUENCE: 15 gccaag 6

<210> SEQ ID NO 16
<211> LENGTH: 14
<212> TYPE: RNA
<213> ORGANISM: Artificial Sequence
<220> FEATURE:
<223> OTHER INFORMATION: The following polyribonucleotide (e.g., RNA) sequence (SEQ ID NO: 16) corresponds to a 5' UTR referred to as TISU+T (with the 3' part of the T7 promoter sequence)

<400> SEQUENCE: 16
gggagacugc caag 14

<210> SEQ ID NO 17
<211> LENGTH: 8
<212> TYPE: RNA
<213> ORGANISM: Artificial Sequence -continued
<220> FEATURE:
<223> OTHER INFORMATION: The following polyribonucleotide (e.g., RNA) sequence (SEQ ID NO: 17) corresponds to a 5' UTR referred to as TISU+T, without promoter sequence

<400> SEQUENCE: 17 cugccaag 8

<210> SEQ ID NO 18
<211> LENGTH: 43
<212> TYPE: RNA
<213> ORGANISM: Artificial Sequence
<220> FEATURE:
<223> OTHER INFORMATION: The following polyribonucleotide (e.g., RNA) sequence (SEQ ID NO: 18) corresponds to a 5' UTR referred to as CYBA 5' UTR, without promoter sequence

<400> SEQUENCE: 18
ccgcgccuag caguguccca gccggguucg ugucgccgcc acc 43

<210> SEQ ID NO 19
<211> LENGTH: 64
<212> TYPE: RNA
<213> ORGANISM: Artificial Sequence
<220> FEATURE:
<223> OTHER INFORMATION: The following polyribonucleotide (e.g., RNA) sequence (SEQ ID NO: 19) corresponds to a 3' UTR referred to as CYBA 3' UTR

<400> SEQUENCE: 19
ccucgccccg gaccugcccu cccgccaggu gcacccaccu gcaauaaaug cagcgaagcc 60
ggga 64

<210> SEQ ID NO 20
<211> LENGTH: 49
<212> TYPE: RNA
<213> ORGANISM: Artificial Sequence
<220> FEATURE:
<223> OTHER INFORMATION: The following polyribonucleotide (e.g., RNA) sequence (SEQ ID NO: 20) corresponds to a 5' UTR referred to as CYBA 5' UTR, with the 3' part of the T7 promoter sequence

<400> SEQUENCE: 20
gggagaccgc gccuagcagu gucccagccg gguucguguc gccgccacc 49

<210> SEQ ID NO 21
<211> LENGTH: 1078
<212> TYPE: RNA
<213> ORGANISM: Artificial Sequence
<220> FEATURE:
<223> OTHER INFORMATION: The following sequence (SEQ ID NO: 21) corresponds to a polyribonucleotide (e.g., RNA) sequence comprising Minimal UTR (SEQ ID NO: 10) and human wildtype OTC (SEQ ID NO: 1)

<400> SEQUENCE: 21
gggagacgcc accaugcugu uuaaucugag gauccuguua aacaaugcag cuuuuagaaa 60
uggucacaac uucaugguuc gaaauuuucg guguggacaa ccacuacaaa auaaagugca 120
gcugaagggc cgugaccuuc ucacucuaaa aaacuuuacc ggagaagaaa uuaaauauau 180
gcuauggcua ucagcagauc ugaaauuuag gauaaaacag aaaggagagu auuugccuuu 240
auugcaaggg aaguccuuag gcaugauuuu ugagaaaaga aguacucgaa caagauuguc 300
uacagaaaca ggcuuugcac uucugggagg acauccuugu uuucuuacca cacaagauau 360
ucauuugggu gugaaugaaa gucucacgga cacggcccgu guauugucua gcauggcaga 420

```
ugcaguauug gcucgagugu auaaacaauc agauuuggac acccuggcua aagaagcauc    480

caucccaauu aucaaugggc ugucagauuu guaccauccu auccagaucc uggcugauua    540

ccucacgcuc caggaacacu auagcucucu gaaaggucuu acccucagcu ggaucgggga    600

ugggaacaau auccugcacu ccaucaugau gagcgcagcg aaauucggaa ugcaccuuca    660

ggcagcuacu ccaaaggguu augagccgga ugcuagugua accaaguugg cagagcagua    720

ugccaaagag aaugguacca agcuguugcu gacaaaugau ccauuggaag cagcgcaugg    780

aggcaaugua uuaauuacag acacuuggau aagcauggga caagaagagg agaagaaaaa    840

gcggcuccag gcuuuccaag guuaccaggu uacaaugaag acugcuaaag uugcugccuc    900

ugacuggaca uuuuuacacu gcuugcccag aaagccagaa gaaguggaug augaagucuu    960

uuauucuccu cgaucacuag uguucccaga ggcagaaaac agaaagugga caaucauggc   1020

ugucauggug ucccugcuga cagauuacuc accucagcuc cagaagccua aauuuuga     1078
```

<210> SEQ ID NO 22
<211> LENGTH: 1108
<212> TYPE: RNA
<213> ORGANISM: Artificial Sequence
<220> FEATURE:
<223> OTHER INFORMATION: The following sequence (SEQ ID NO: 22) corresponds to a polyribonucleotide (e.g., RNA) sequence comprising human alpha globin UTR (SEQ ID NO: 12) and human wildtype OTC (SEQ ID NO: 1)

<400> SEQUENCE: 22

```
gggagacucu ucugguCccc acagacucag agagaacgcc accaugcugu uuaaucugag     60

gauccuguua aacaaugcag cuuuuagaaa uggucacaac uucaugguuc gaaauuuucg    120

guguggacaa ccacuacaaa auaaagugca gcugaagggc cgugaccuuc ucacucuaaa    180

aaacuuuacc ggagaagaaa uuaaauauau gcuauggcua ucagcagauc ugaaauuuag    240

gauaaaacag aaaggagagu auuugccuuu auugcaaggg aaguccuuag gcaugauuuu    300

ugagaaaaga aguacucgaa caagauuguc uacagaaaca ggcuuugcac uucugggagg    360

acauccuugu uuucuuacca cacaagauau ucauuugggu gugaaugaaa gucucacgga    420

cacggcccgu guauugucua gcauggcaga ugcaguauug gcucgagugu auaaacaauc    480

agauuuggac acccuggcua aagaagcauc caucccaauu aucaaugggc ugucagauuu    540

guaccauccu auccagaucc uggcugauua ccucacgcuc caggaacacu auagcucucu    600

gaaaggucuu acccucagcu ggaucgggga ugggaacaau auccugcacu ccaucaugau    660

gagcgcagcg aaauucggaa ugcaccuuca ggcagcuacu ccaaaggguu augagccgga    720

ugcuagugua accaaguugg cagagcagua ugccaaagag aaugguacca agcuguugcu    780

gacaaaugau ccauuggaag cagcgcaugg aggcaaugua uuaauuacag acacuuggau    840

aagcauggga caagaagagg agaagaaaaa gcggcuccag gcuuuccaag guuaccaggu    900

uacaaugaag acugcuaaag uugcugccuc ugacuggaca uuuuuacacu gcuugcccag    960

aaagccagaa gaaguggaug augaagucuu uuauucuccu cgaucacuag uguucccaga   1020

ggcagaaaac agaaagugga caaucauggc ugucauggug ucccugcuga cagauuacuc   1080

accucagcuc cagaagccua aauuuuga                                      1108
```

<210> SEQ ID NO 23
<211> LENGTH: 1178
<212> TYPE: RNA
<213> ORGANISM: Artificial Sequence -continued
<220> FEATURE:
<223> OTHER INFORMATION: The following sequence (SEQ ID NO: 23) corresponds to a polyribonucleotide (e.g., RNA) sequence comprising CYBA 5' UTR (SEQ ID NO: 20), human wildtype OTC (SEQ ID NO: 1) and CYBA 3' UTR (SEQ ID NO: 19)

<400> SEQUENCE: 23

```
gggagaccgc gccuagcagu gucccagccg gguucguguc gccgccacca ugcuguuuaa      60

ucugaggauc cuguuaaaca augcagcuuu uagaaauggu cacaacuuca ugguucgaaa     120

uuuucggugu ggacaaccac uacaaaauaa agugcagcug aagggccgug accuucucac     180

ucuaaaaaac uuuaccggag aagaaauuaa auauaugcua uggcuaucag cagaucugaa     240

auuuaggaua aaacagaaag gagaguauuu gccuuuauug caagggaagu ccuuaggcau     300

gauuuuugag aaaagaagua cucgaacaag auugucuaca gaaacaggcu uugcacuucu     360

gggaggacau ccuuguuuuc uuaccacaca agauauucau uuggguguga augaaagucu     420

cacggacacg gcccguguau ugucuagcau ggcagaugca guauuggcuc gaguguauaa     480

acaaucagau uuggacaccc uggcuaaaga agcauccauc ccaauuauca augggcuguc     540

agauuuguac cauccuaucc agauccuggc ugauuaccuc acgcuccagg aacacuauag     600

cucucugaaa ggucuuaccc ucagcuggau cggggauggg aacaauaucc ugcacuccau     660

caugaugagc gcagcgaaau ucggaaugca ccuucaggca gcuacuccaa aggguuauga     720

gccggaugcu aguguaacca aguuggcaga gcaguaugcc aaagagaaug guaccaagcu     780

guugcugaca aaugauccau uggaagcagc gcauggaggc aauguauuaa uuacagacac     840

uuggauaagc augggacaag aagaggagaa gaaaaagcgg cuccaggcuu uccaagguua     900

ccagguuaca augaagacug cuaaaguugc ugccucugac uggacauuuu uacacugcuu     960

gcccagaaag ccagaagaag uggaugauga agucuuuuau ucuccucgau cacuaguguu    1020

cccagaggca gaaaacagaa aguggacaau cauggcuguc augguguccc ugcugacaga    1080

uuacucaccu cagcuccaga agccuaaauu uugaccucgc ccggaccug cccucccgcc    1140

aggugcaccc accugcaaua aaugcagcga agccggga                           1178
```

<210> SEQ ID NO 24
<211> LENGTH: 1078
<212> TYPE: RNA
<213> ORGANISM: Artificial Sequence
<220> FEATURE:
<223> OTHER INFORMATION: The following sequence (SEQ ID NO: 24) corresponds to a polyribonucleotide (e.g., RNA) sequence comprising Minimal UTR (SEQ ID NO: 10) and human codon-optimized OTC (SEQ ID NO: 4)

<400> SEQUENCE: 24

```
gggagacgcc accaugcugu ucaaccugcg gauccugcug aacaacgccg ccuuccggaa      60

cggccacaac uucauggugc gcaacuucag augcggccag ccccugcaga acaaggugca     120

gcugaagggc agggaccugc ugacccugaa gaacuucacc ggcgaagaga ucaaguacau     180

gcuguggcug agcgccgacc ugaaguuccg gaucaagcag aagggcgagu accugccccu     240

gcugcagggc aagucucugg gcaugaucuu cgagaagcgg agcacccgga cccggcuguc     300

uaccgagaca ggauuugccc ugcugggcgg ccacccuugc uuucugacca cccaggauau     360

ccaccugggc gugaacgaga gccugaccga cacagccaga gugcugagca gcauggccga     420

ugccgugcug gccagagugu acaagcagag cgaccuggac acccuggcca aagaggccag     480

cauccccauc aucaacggcc uguccgaccu guaccacccc auccagaucc uggccgacua     540
```

```
ccugacccug caggaacacu acagcucccu gaagggccug acacugagcu ggaucggcga    600

cggcaacaac auccugcacu cuaucaugau gagcgccgcc aaguucggca ugcaucugca    660

ggccgccacc cccaagggcu augagccuga ugccagcgug accaagcugg ccgagcagua    720

cgccaaagag aacggcacca agcugcugcu gaccaacgac ccucuggaag ccgcccacgg    780

cggcaaugug cugaucaccg auaccuggau cagcaugggc caggaagagg aaaagaagaa    840

gcggcugcag gccuuccagg gcuaccaagu gaccaugaag accgccaaag uggccgccag    900

cgacuggacc uuccugcacu gccugcccag aaagcccgaa gagguggacg acgagguguu    960

cuacagcccc cggucccugg uguuucccga ggccgagaac cggaagugga ccaucauggc   1020

ugugauggug ucucugcuga ccgacuacuc cccccagcug cagaagccca aguucuga    1078
```

```
<210> SEQ ID NO 25
<211> LENGTH: 1108
<212> TYPE: RNA
<213> ORGANISM: Artificial Sequence
<220> FEATURE:
<223> OTHER INFORMATION: The following sequence (SEQ ID NO: 25)
      corresponds to a polyribonucleotide (e.g., RNA) sequence
      comprising human alpha globin UTR (SEQ ID NO: 12) and human codon-
      optimized OTC (SEQ ID NO: 4)

<400> SEQUENCE: 25

gggagacucu ucuggucccc acagacucag agagaacgcc accaugcugu ucaaccugcg     60

gauccugcug aacaacgccg ccuuccggaa cggccacaac uucauggugc gcaacuucag    120

augcggccag ccccugcaga acaaggugca gcugaagggc agggaccugc ugacccugaa    180

gaacuucacc ggcgaagaga ucaaguacau gcuguggcug agcgccgacc ugaaguuccg    240

gaucaagcag aagggcgagu accugccccu gcugcagggc aagucucugg gcaugaucuu    300

cgagaagcgg agcacccgga cccggcuguc uaccgagaca ggauuugccc ugcugggcgg    360

ccacccuugc uuucugacca cccaggauau ccaccugggc gugaacgaga gccugaccga    420

cacagccaga gugcugagca gcauggccga ugccgugcug gccagagugu acaagcagag    480

cgaccuggac acccuggcca aagaggccag cauccccauc aucaacggcc uguccgaccu    540

guaccacccc auccagaucc uggccgacua ccugacccug caggaacacu acagcucccu    600

gaagggccug acacugagcu ggaucggcga cggcaacaac auccugcacu cuaucaugau    660

gagcgccgcc aaguucggca ugcaucugca ggccgccacc cccaagggcu augagccuga    720

ugccagcgug accaagcugg ccgagcagua cgccaaagag aauggcacca agcugcugcu    780

gaccaacgac ccccuggaag ccgcccaugg cggcaaugug cugaucaccg acaccuggau    840

cagcaugggc caggaagagg aaaagaagaa gcggcugcag gccuuccagg gcuaccaagu    900

gaccaugaag accgccaaag uggccgccag cgacuggacc uuccugcacu gccugcccag    960

aaagcccgaa gagguggacg acgagguguu cuacagcccc cggucccugg uguuucccga   1020

ggccgagaac cggaagugga ccaucauggc ugugauggug ucucugcuga ccgacuacuc   1080

cccccagcug cagaagccca aguucuga                                      1108
```

```
<210> SEQ ID NO 26
<211> LENGTH: 1178
<212> TYPE: RNA
<213> ORGANISM: Artificial Sequence
<220> FEATURE:
<223> OTHER INFORMATION: The following sequence (SEQ ID NO: 26)
      corresponds to a polyribonucleotide (e.g., RNA) sequence
      comprising CYBA 5' UTR (SEQ ID NO: 20), human codon-optimized OTC
      (SEQ ID NO: 4) and CYBA 3' UTR (SEQ ID NO: 19)
```

<400> SEQUENCE: 26
gggagaccgc gccuagcagu gucccagccg gguucguguc gccgccacca ugcuguucaa 60
ccugcggauc cugcugaaca acgccgccuu ccggaacggc cacaacuuca uggugcgcaa 120
cuucagaugc ggccagcccc ugcagaacaa ggugcagcug aagggcaggg accugcugac 180
ccugaagaac uucaccggcg aagagaucaa guacaugcug uggcugagcg ccgaccugaa 240
guuccggauc aagcagaagg gcgaguaccu gccccugcug cagggcaagu cucugggcau 300
gaucuucgag aagcggagca cccggacccg gcugucuacc gagacaggau uugcccugcu 360
gggcggccac ccuugcuuuc ugaccaccca ggauauccac cugggcguga acgagagccu 420
gaccgacaca gccagagugc ugagcagcau ggccgaugcc gugcuggcca gaguguacaa 480
gcagagcgac cuggacaccc uggccaaaga ggccagcauc cccaucauca acggccuguc 540
cgaccuguac caccccaucc agauccuggc cgacuaccug acccugcagg aacacuacag 600
cucccugaag ggccugacac ugagcuggau cggcgacggc aacaacaucc ugcacucuau 660
caugaugagc gccgccaagu ucggcaugca ucugcaggcc gccacccccca agggcuauga 720 gccugaugcc agcgugacca agcuggccga gcaguacgcc aaagagaacg gcaccaagcu 780
gcugcugacc aacgacccuc uggaagccgc ccacggcggc aaugugcuga ucaccgauac 840
cuggaucagc augggccagg aagaggaaaa gaagaagcgg cugcaggccu uccagggcua 900
ccaagugacc augaagaccg ccaaagugcc cgccagcgac uggaccuucc ugcacugccu 960
gcccagaaag cccgaagagg uggacgacga gguguucuac agccccccggu cccugguguu 1020 ucccgaggcc gagaaccgga aguggaccau cauggcugug augguguucuc ugcugaccga 1080 cuacuccccc cagcugcaga agcccaaguu cugaccucgc cccggaccug cccucccgcc 1140
aggugcaccc accugcaaua aaugcagcga agccggga 1178

<210> SEQ ID NO 27
<211> LENGTH: 1079
<212> TYPE: RNA
<213> ORGANISM: Artificial Sequence
<220> FEATURE:
<223> OTHER INFORMATION: The following sequence (SEQ ID NO: 27) corresponds to a polyribonucleotide (e.g., RNA) sequence comprising a TISU + T element (SEQ ID NO: 16) and human codon-optimized OTC (SEQ ID NO: 4)

<400> SEQUENCE: 27
gggagacugc caagaugcug uucaaccugc ggauccugcu gaacaacgcc gccuuccgga 60
acggccacaa cuucauggug cgcaacuuca gaugcggcca gccccugcag aacaaggugc 120
agcugaaggg cagggaccug cugacccuga agaacuucac cggcgaagag aucaaguaca 180
ugcuguggcu gagcgccgac cugaaguucc ggaucaagca gaagggcgag uaccugcccc 240
ugcugcaggg caagucucug ggcaugaucu ucgagaagcg gagcacccgg acccggcugu 300
cuaccgagac aggauuugcc cugcugggcg gccacccuug cuuucugacc acccaggaua 360
uccaccuggg cgugaacgag agccugaccg acacagccag agugcugagc agcauggccg 420
augccgugcu ggccagagug uacaagcaga gcgaccugga cacccuggcc aaagaggcca 480
gcauccccau caucaacggc cuguccgacc uguaccaccc cauccagauc cuggccgacu 540
accugacccu gcaggaacac uacagcuccc ugaagggccu gacacugagc uggaucggcg 600
acggcaacaa cauccugcac ucuaucauga ugagcgccgc caaguucggc augcaucugc 660
aggccgccac ccccaagggc uaugagccug augccagcgu gaccaagcug gccgagcagu 720
acgccaaaga gaacggcacc aagcugcugc ugaccaacga cccucuggaa gccgcccacg 780
gcggcaaugu gcugaucacc gauaccugga ucagcauggg ccaggaagag gaaaagaaga 840
agcggcugca ggccuuccag ggcuaccaag ugaccaugaa gaccgccaaa guggccgcca 900
gcgacuggac cuuccugcac ugccugccca gaaagcccga agagguggac gacgaggugu 960
ucuacagccc ccggucccug guguuucccg aggccgagaa ccggaagugg accaucaugg 1020
cugugauggu gucucugcug accgacuacu ccccccagcu gcagaagccc aaguucuga 1079

<210> SEQ ID NO 28
<211> LENGTH: 66
<212> TYPE: RNA
<213> ORGANISM: Artificial Sequence
<220> FEATURE:
<223> OTHER INFORMATION: The following polyribonucleotide (e.g., RNA) sequence (SEQ ID NO: 28) corresponds to a 5' UTR derived from ?-globin 5' UTR, referred to as HBA2 (NM_000517.4) with the transcription start site at position 30

<400> SEQUENCE: 28
cauaaacccu ggcgcgcucg cgggccggca cucuucuggu ccccacagac ucagagagaa 60
cccacc 66

<210> SEQ ID NO 29
<211> LENGTH: 37
<212> TYPE: RNA
<213> ORGANISM: Artificial Sequence
<220> FEATURE:
<223> OTHER INFORMATION: The following polyribonucleotide (e.g., RNA) sequence (SEQ ID NO: 29) corresponds to a 5' UTR derived from ?-globin 5' UTR, referred to as ETH

<400> SEQUENCE: 29
cucuucuggu ccccacagac ucagagagaa cgccacc 37

<210> SEQ ID NO 30
<211> LENGTH: 100
<212> TYPE: RNA
<213> ORGANISM: Artificial Sequence
<220> FEATURE:
<223> OTHER INFORMATION: The following polyribonucleotide (e.g., RNA) sequence (SEQ ID NO: 30) corresponds to hGH 3' UTR, as disclosed in WO 2012/170930

<400> SEQUENCE: 30
cggguggcau cccugugacc ccuccccagu gccucuccug gcccuggaag uugccacucc 60
agugcccacc agccuugucc uaauaaaauu aaguugcauc 100

<210> SEQ ID NO 31
<211> LENGTH: 1671
<212> TYPE: DNA
<213> ORGANISM: Artificial Sequence
<220> FEATURE:
<223> OTHER INFORMATION: The following sequence (SEQ ID NO: 31) corresponds to a polynucleotide (e.g., DNA) sequence comprising the T7 promoter and the human wildtype OTC (SEQ ID NO: 1) together with its natural 5' and 3' UTR

<400> SEQUENCE: 31
taatacgact cactataggg agacagcggt ggagcttggc ataaagttca aatgctccta 60
caccctgccc tgcagtatct ctaaccaggg gactttgata aggaagctga agggtgatat 120
tacctttgct ccctcactgc aactgaacac atttcttagt ttttaggtgg cccccgctgg 180

-continued

```
ctaacttgct gtggagtttt caagggcata gaatcgtcct ttacacaatt aaaagaagat    240

gctgtttaat ctgaggatcc tgttaaacaa tgcagctttt agaaatggtc acaacttcat    300

ggttcgaaat tttcggtgtg gacaaccact acaaaataaa gtgcagctga agggccgtga    360

ccttctcact ctaaaaaact ttaccggaga agaaattaaa tatatgctat ggctatcagc    420

agatctgaaa tttaggataa aacagaaagg agagtatttg cctttattgc aagggaagtc    480

cttaggcatg atttttgaga aaagaagtac tcgaacaaga ttgtctacag aaacaggctt    540

tgcacttctg ggaggacatc cttgttttct taccacacaa gatattcatt tgggtgtgaa    600

tgaaagtctc acggacacgg cccgtgtatt gtctagcatg gcagatgcag tattggctcg    660

agtgtataaa caatcagatt tggacaccct ggctaaagaa gcatccatcc caattatcaa    720

tgggctgtca gatttgtacc atcctatcca gatcctggct gattacctca cgctccagga    780

acactatagc tctctgaaag gtcttaccct cagctggatc ggggatggga acaatatcct    840

gcactccatc atgatgagcg cagcgaaatt cggaatgcac cttcaggcag ctactccaaa    900

gggttatgag ccggatgcta gtgtaaccaa gttggcagag cagtatgcca aagagaatgg    960

taccaagctg ttgctgacaa atgatccatt ggaagcagcg catggaggca atgtattaat   1020

tacagacact tggataagca tgggacaaga agaggagaag aaaaagcggc tccaggcttt   1080

ccaaggttac caggttacaa tgaagactgc taaagttgct gcctctgact ggacattttt   1140

acactgcttg cccagaaagc cagaagaagt ggatgatgaa gtcttttatt ctcctcgatc   1200

actagtgttc ccagaggcag aaaacagaaa gtggacaatc atggctgtca tggtgtccct   1260

gctgacagat tactcacctc agctccagaa gcctaaattt tgatgttgtg ttacttgtca   1320

agaaagaagc aatgttcttc agtaacagaa tgagttggtt tatggggaaa agagaagaga   1380

atctaaaaaa taaacaaatc cctaacacgt ggtatgggtg aaccgtatga tatgctttgc   1440

cattgtgaaa ctttccttaa gcctttaatt taagtgctga tgcactgtaa tacgtgctta   1500

actttgctta aactctctaa ttcccaattt ctgagttaca tttagatatc atattaatta   1560

tcatatacat ttacttcaac ataaaatact gtgttcataa tgtataatgt ctaagccatt   1620

aagtgtaatc tatgcttatt acctaaataa attatcaccc atgctaattt a            1671
```

<210> SEQ ID NO 32
<211> LENGTH: 1095
<212> TYPE: DNA
<213> ORGANISM: Artificial Sequence
<220> FEATURE:
<223> OTHER INFORMATION: The following sequence (SEQ ID NO: 32) corresponds to a polynucleotide (e.g., DNA) sequence comprising the T7 promoter, Minimal UTR and human wildtype OTC (SEQ ID NO: 1)

<400> SEQUENCE: 32

```
taatacgact cactataggg agacgccacc atgctgttta atctgaggat cctgttaaac     60

aatgcagctt ttagaaatgg tcacaacttc atggttcgaa attttcggtg tggacaacca    120

ctacaaaata aagtgcagct gaagggccgt gaccttctca ctctaaaaaa ctttaccgga    180

gaagaaatta aatatatgct atggctatca gcagatctga aatttaggat aaaacagaaa    240

ggagagtatt tgcctttatt gcaagggaag tccttaggca tgatttttga gaaaagaagt    300

actcgaacaa gattgtctac agaaacaggc tttgcacttc tgggaggaca tccttgtttt    360

cttaccacac aagatattca tttgggtgtg aatgaaagtc tcacggacac ggcccgtgta    420

ttgtctagca tggcagatgc agtattggct cgagtgtata aacaatcaga tttggacacc    480

ctggctaaag aagcatccat cccaattatc aatgggctgt cagatttgta ccatcctatc    540
```

```
cagatcctgg ctgattacct cacgctccag gaacactata gctctctgaa aggtcttacc    600

ctcagctgga tcggggatgg gaacaatatc ctgcactcca tcatgatgag cgcagcgaaa    660

ttcggaatgc accttcaggc agctactcca aagggttatg agccggatgc tagtgtaacc    720

aagttggcag agcagtatgc caaagagaat ggtaccaagc tgttgctgac aaatgatcca    780

ttggaagcag cgcatggagg caatgtatta attacagaca cttggataag catgggacaa    840

gaagaggaga agaaaaagcg gctccaggct ttccaaggtt accaggttac aatgaagact    900

gctaaagttg ctgcctctga ctggacattt ttacactgct tgcccagaaa gccagaagaa    960

gtggatgatg aagtctttta ttctcctcga tcactagtgt tcccagaggc agaaaacaga   1020

aagtggacaa tcatggctgt catggtgtcc ctgctgacag attactcacc tcagctccag   1080

aagcctaaat tttga                                                     1095
```

<210> SEQ ID NO 33
<211> LENGTH: 1125
<212> TYPE: DNA
<213> ORGANISM: Artificial Sequence
<220> FEATURE:
<223> OTHER INFORMATION: The following sequence (SEQ ID NO: 33) corresponds to a polynucleotide (e.g., DNA) sequence comprising the T7 promoter, human alpha globin UTR and human wildtype OTC (SEQ ID NO: 1)

<400> SEQUENCE: 33

```
taatacgact cactataggg agactcttct ggtccccaca gactcagaga gaacgccacc     60

atgctgttta atctgaggat cctgttaaac aatgcagctt ttagaaatgg tcacaacttc    120

atggttcgaa attttcggtg tggacaacca ctacaaaata aagtgcagct gaagggccgt    180

gaccttctca ctctaaaaaa ctttaccgga gaagaaatta aatatatgct atggctatca    240

gcagatctga aatttaggat aaaacagaaa ggagagtatt tgcctttatt gcaagggaag    300

tccttaggca tgatttttga gaaaagaagt actcgaacaa gattgtctac agaaacaggc    360

tttgcacttc tgggaggaca tccttgtttt cttaccacac aagatattca tttgggtgtg    420

aatgaaagtc tcacggacac ggcccgtgta ttgtctagca tggcagatgc agtattggct    480

cgagtgtata aacaatcaga tttggacacc ctggctaaag aagcatccat cccaattatc    540

aatgggctgt cagatttgta ccatcctatc cagatcctgg ctgattacct cacgctccag    600

gaacactata gctctctgaa aggtcttacc ctcagctgga tcggggatgg gaacaatatc    660

ctgcactcca tcatgatgag cgcagcgaaa ttcggaatgc accttcaggc agctactcca    720

aagggttatg agccggatgc tagtgtaacc aagttggcag agcagtatgc caaagagaat    780

ggtaccaagc tgttgctgac aaatgatcca ttggaagcag cgcatggagg caatgtatta    840

attacagaca cttggataag catgggacaa gaagaggaga agaaaaagcg gctccaggct    900

ttccaaggtt accaggttac aatgaagact gctaaagttg ctgcctctga ctggacattt    960

ttacactgct tgcccagaaa gccagaagaa gtggatgatg aagtctttta ttctcctcga   1020

tcactagtgt tcccagaggc agaaaacaga aagtggacaa tcatggctgt catggtgtcc   1080

ctgctgacag attactcacc tcagctccag aagcctaaat tttga                   1125
```

<210> SEQ ID NO 34
<211> LENGTH: 1195
<212> TYPE: DNA
<213> ORGANISM: Artificial Sequence
<220> FEATURE:
<223> OTHER INFORMATION: The following sequence (SEQ ID NO: 34)

-continued corresponds to a polynucleotide (e.g., DNA) sequence comprising the T7 promoter, CYBA 5' UTR, human wildtype OTC (SEQ ID NO: 1) and CYBA 3' UTR

<400> SEQUENCE: 34

```
taatacgact cactataggg agaccgcgcc tagcagtgtc ccagccgggt tcgtgtcgcc      60
gccaccatgc tgtttaatct gaggatcctg ttaaacaatg cagcttttag aaatggtcac     120
aacttcatgg ttcgaaattt tcggtgtgga caaccactac aaaataaagt gcagctgaag     180
ggccgtgacc ttctcactct aaaaaacttt accggagaag aaattaaata tatgctatgg     240
ctatcagcag atctgaaatt taggataaaa cagaaaggag agtatttgcc tttattgcaa     300
gggaagtcct taggcatgat ttttgagaaa agaagtactc gaacaagatt gtctacagaa     360
acaggctttg cacttctggg aggacatcct tgttttctta ccacacaaga tattcatttg     420
ggtgtgaatg aaagtctcac ggacacggcc cgtgtattgt ctagcatggc agatgcagta     480
ttggctcgag tgtataaaca atcagatttg gacaccctgg ctaaagaagc atccatccca     540
attatcaatg ggctgtcaga tttgtaccat cctatccaga tcctggctga ttacctcacg     600
ctccaggaac actatagctc tctgaaaggt cttaccctca gctggatcgg ggatgggaac     660
aatatcctgc actccatcat gatgagcgca gcgaaattcg gaatgcacct tcaggcagct     720
actccaaagg gttatgagcc ggatgctagt gtaaccaagt tggcagagca gtatgccaaa     780
gagaatggta ccaagctgtt gctgacaaat gatccattgg aagcagcgca tggaggcaat     840
gtattaatta cagacacttg gataagcatg ggacaagaag aggagaagaa aaagcggctc     900
caggctttcc aaggttacca ggttacaatg aagactgcta aagttgctgc ctctgactgg     960
acatttttac actgcttgcc cagaaagcca gaagaagtgg atgatgaagt cttttattct    1020
cctcgatcac tagtgttccc agaggcagaa aacagaaagt ggacaatcat ggctgtcatg    1080
gtgtccctgc tgacagatta ctcacctcag ctccagaagc ctaaattttg acctcgcccc    1140
ggacctgccc tcccgccagg tgcacccacc tgcaataaat gcagcgaagc cggga         1195
```

<210> SEQ ID NO 35
<211> LENGTH: 1671
<212> TYPE: DNA
<213> ORGANISM: Artificial Sequence
<220> FEATURE:
<223> OTHER INFORMATION: The following sequence (SEQ ID NO: 35) corresponds to a polynucleotide (e.g., DNA) sequence comprising the T7 promoter and the human codon optimized OTC (SEQ ID NO: 4) together with its natural 5' and 3' UTR

<400> SEQUENCE: 35

```
taatacgact cactataggg agacagcggt ggagcttggc ataaagttca aatgctccta      60
caccctgccc tgcagtatct ctaaccaggg gactttgata aggaagctga agggtgatat     120
tacctttgct ccctcactgc aactgaacac atttcttagt ttttaggtgg cccccgctgg     180
ctaacttgct gtggagtttt caagggcata gaatcgtcct ttacacaatt aaaagaagat     240
gctgttcaac ctgcggatcc tgctgaacaa cgccgccttc cggaacggcc acaacttcat     300
ggtgcgcaac ttcagatgcg gccagcccct gcagaacaag gtgcagctga aaggccggga     360
cctgctgacc ctgaagaact tcaccggcga agagatcaag tacatgctgt ggctgagcgc     420
cgacctgaag ttccggatca agcagaaggg cgagtacctg cccctgctgc agggaaagtc     480
cctgggcatg atcttcgaga agcggagcac ccggacccgg ctgtctaccg agacaggatt     540
tgccctgctg ggcggccacc cttgctttct gaccacccag gatatccacc tgggcgtgaa     600
```

```
cgagagcctg accgacacag ccagagtgct gagcagcatg gccgatgccg tgctggccag    660

agtgtacaag cagagcgacc tggacaccct ggccaaagag gccagcatcc ccatcatcaa    720

cggcctgtcc gacctgtacc accccatcca gatcctggcc gactacctga ccctgcagga    780

acactacagc agcctgaagg gcctgacact gagctggatc ggcgacggca acaacatcct    840

gcactctatc atgatgagcg ccgccaagtt cggcatgcat ctgcaggccg ccacccccaa    900

gggctatgag cctgatgcca gcgtgaccaa gctggccgag cagtacgcca aagagaacgg    960

caccaagctg ctgctgacca acgaccctct ggaagccgcc cacggcggca atgtgctgat   1020

caccgatacc tggatcagca tgggccagga agaggaaaag aagaagcggc tgcaggcctt   1080

ccagggctac caagtgacca tgaagaccgc caaagtggcc gccagcgact ggaccttcct   1140

gcactgcctg cccagaaagc ccgaagaggt ggacgacgag gtgttctaca gcccccggtc   1200

cctggtgttt cccgaggccg agaaccggaa gtggaccatc atggctgtga tggtgtctct   1260

gctgaccgac tactcccccc agctgcagaa acccaagttc tgatgttgtg ttacttgtca   1320

agaaagaagc aatgttcttc agtaacagaa tgagttggtt tatggggaaa agagaagaga   1380

atctaaaaaa taaacaaatc cctaacacgt ggtatgggtg aaccgtatga tatgctttgc   1440

cattgtgaaa ctttccttaa gcctttaatt taagtgctga tgcactgtaa tacgtgctta   1500

actttgctta aactctctaa ttcccaattt ctgagttaca tttagatatc atattaatta   1560

tcatatacat ttacttcaac ataaaatact gtgttcataa tgtataatgt ctaagccatt   1620

aagtgtaatc tatgcttatt acctaaataa attatcaccc atgctaattt a            1671
```

<210> SEQ ID NO 36
<211> LENGTH: 1095
<212> TYPE: DNA
<213> ORGANISM: Artificial Sequence
<220> FEATURE:
<223> OTHER INFORMATION: The following sequence (SEQ ID NO: 36) corresponds to a polynucleotide (e.g., DNA) sequence comprising the T7 promoter, Minimal UTR and human codon-optimized OTC (SEQ ID NO: 4)

<400> SEQUENCE: 36

```
taatacgact cactataggg agacgccacc atgctgttca acctgcggat cctgctgaac     60

aacgccgcct tccggaacgg ccacaacttc atggtgcgca acttcagatg cggccagccc    120

ctgcagaaca aggtgcagct gaagggcagg gacctgctga ccctgaagaa cttcaccggc    180

gaagagatca agtacatgct gtggctgagc gccgacctga agttccggat caagcagaag    240

ggcgagtacc tgcccctgct gcagggcaag tctctgggca tgatcttcga gaagcggagc    300

acccggaccc ggctgtctac cgagacagga tttgccctgc tgggcggcca ccccttgcttt    360

ctgaccaccc aggatatcca cctgggcgtg aacgagagcc tgaccgacac agccagagtg    420

ctgagcagca tggccgatgc cgtgctggcc agagtgtaca agcagagcga cctggacacc    480

ctggccaaag aggccagcat ccccatcatc aacggcctgt ccgacctgta ccaccccatc    540

cagatcctgg ccgactacct gaccctgcag gaacactaca gctccctgaa gggcctgaca    600

ctgagctgga tcggcgacgg caacaacatc ctgcactcta tcatgatgag cgccgccaag    660

ttcggcatgc atctgcaggc cgccaccccc aagggctatg agcctgatgc cagcgtgacc    720

aagctggccg agcagtacgc caaagagaac ggcaccaagc tgctgctgac caacgaccct    780

ctggaagccg cccacggcgg caatgtgctg atcaccgata cctggatcag catgggccag    840

gaagaggaaa agaagaagcg gctgcaggcc ttccagggct accaagtgac catgaagacc    900
```

-continued

```
gccaaagtgg ccgccagcga ctggaccttc ctgcactgcc tgcccagaaa gcccgaagag    960

gtggacgacg aggtgttcta cagcccccgg tccctggtgt ttcccgaggc cgagaaccgg   1020

aagtggacca tcatggctgt gatggtgtct ctgctgaccg actactcccc ccagctgcag   1080

aagcccaagt tctga                                                    1095
```

<210> SEQ ID NO 37
<211> LENGTH: 1125
<212> TYPE: DNA
<213> ORGANISM: Artificial Sequence
<220> FEATURE:
<223> OTHER INFORMATION: The following sequence (SEQ ID NO: 37) corresponds to a polynucleotide (e.g., DNA) sequence comprising the T7 promoter, human alpha globin UTR (SEQ ID NO: 12) and human codon-optimized OTC (SEQ ID NO: 4)

<400> SEQUENCE: 37

```
taatacgact cactataggg agactcttct ggtccccaca gactcagaga gaacgccacc     60

atgctgttca acctgcggat cctgctgaac aacgccgcct tccggaacgg ccacaacttc    120

atggtgcgca acttcagatg cggccagccc ctgcagaaca aggtgcagct gaagggcagg    180

gacctgctga ccctgaagaa cttcaccggc gaagagatca agtacatgct gtggctgagc    240

gccgacctga agttccggat caagcagaag ggcgagtacc tgcccctgct gcagggcaag    300

tctctgggca tgatcttcga gaagcggagc acccggaccc ggctgtctac cgagacagga    360

tttgccctgc tgggcggcca ccccttgcttt ctgaccaccc aggatatcca cctgggcgtg    420

aacgagagcc tgaccgacac agccagagtg ctgagcagca tggccgatgc cgtgctggcc    480

agagtgtaca agcagagcga cctggacacc ctggccaaag aggccagcat ccccatcatc    540

aacggcctgt ccgacctgta ccaccccatc cagatcctgg ccgactacct gaccctgcag    600

gaacactaca gctccctgaa gggcctgaca ctgagctgga tcggcgacgg caacaacatc    660

ctgcactcta tcatgatgag cgccgccaag ttcggcatgc atctgcaggc cgccaccccc    720

aagggctatg agcctgatgc cagcgtgacc aagctggccg agcagtacgc caaagagaat    780

ggcaccaagc tgctgctgac caacgacccc ctggaagccg cccatggcgg caatgtgctg    840

atcaccgaca cctggatcag catgggccag gaagaggaaa agaagaagcg gctgcaggcc    900

ttccagggct accaagtgac catgaagacc gccaaagtgg ccgccagcga ctggaccttc    960

ctgcactgcc tgcccagaaa gcccgaagag gtggacgacg aggtgttcta cagcccccgg   1020

tccctggtgt ttcccgaggc cgagaaccgg aagtggacca tcatggctgt gatggtgtct   1080

ctgctgaccg actactcccc ccagctgcag aagcccaagt tctga                   1125
```

<210> SEQ ID NO 38
<211> LENGTH: 1195
<212> TYPE: DNA
<213> ORGANISM: Artificial Sequence
<220> FEATURE:
<223> OTHER INFORMATION: The following sequence (SEQ ID NO: 38) corresponds to a polynucleotide (e.g., DNA) sequence comprising the T7 promoter, CYBA 5' UTR, human codon-optimized OTC (SEQ ID NO: 4) and CYBA 3' UTR

<400> SEQUENCE: 38

```
taatacgact cactataggg agaccgcgcc tagcagtgtc ccagccgggt tcgtgtcgcc     60

gccaccatgc tgttcaacct gcggatcctg ctgaacaacg ccgccttccg gaacggccac    120

aacttcatgg tgcgcaactt cagatgcggc cagcccctgc agaacaaggt gcagctgaag    180

ggcagggacc tgctgaccct gaagaacttc accggcgaag agatcaagta catgctgtgg    240
```

ctgagcgccg acctgaagtt ccggatcaag cagaagggcg agtacctgcc cctgctgcag 300
ggcaagtctc tgggcatgat cttcgagaag cggagcaccc ggacccggct gtctaccgag 360
acaggatttg ccctgctggg cggccaccct tgctttctga ccacccagga tatccacctg 420
ggcgtgaacg agagcctgac cgacacagcc agagtgctga gcagcatggc cgatgccgtg 480
ctggccagag tgtacaagca gagcgacctg gacaccctgg ccaaagaggc cagcatcccc 540
atcatcaacg gcctgtccga cctgtaccac cccatccaga tcctggccga ctacctgacc 600
ctgcaggaac actacagctc cctgaagggc ctgacactga gctggatcgg cgacggcaac 660
aacatcctgc actctatcat gatgagcgcc gccaagttcg gcatgcatct gcaggccgcc 720
acccccaagg gctatgagcc tgatgccagc gtgaccaagc tggccgagca gtacgccaaa 780
gagaacggca ccaagctgct gctgaccaac gaccctctgg aagccgccca cggcggcaat 840
gtgctgatca ccgatacctg gatcagcatg ggccaggaag aggaaaagaa gaagcggctg 900
caggccttcc agggctacca agtgaccatg aagaccgcca aagtggccgc cagcgactgg 960
accttcctgc actgcctgcc cagaaagccc gaagaggtgg acgacgaggt gttctacagc 1020
ccccggtccc tggtgtttcc cgaggccgag aaccggaagt ggaccatcat ggctgtgatg 1080
gtgtctctgc tgaccgacta ctccccccag ctgcagaagc ccaagttctg acctcgcccc 1140
ggacctgccc tcccgccagg tgcacccacc tgcaataaat gcagcgaagc cggga 1195

<210> SEQ ID NO 39
<211> LENGTH: 1096
<212> TYPE: DNA
<213> ORGANISM: Artificial Sequence
<220> FEATURE:
<223> OTHER INFORMATION: The following sequence (SEQ ID NO: 39) corresponds to a polynucleotide (e.g., DNA) sequence comprising the T7 promoter, a TISU + T element and human codon-optimized OTC (SEQ ID NO: 4)

<400> SEQUENCE: 39
taatacgact cactataggg agactgccaa gatgctgttc aacctgcgga tcctgctgaa 60
caacgccgcc ttccggaacg gccacaactt catggtgcgc aacttcagat gcggccagcc 120
cctgcagaac aaggtgcagc tgaagggcag ggacctgctg accctgaaga acttcaccgg 180
cgaagagatc aagtacatgc tgtggctgag cgccgacctg aagttccgga tcaagcagaa 240
gggcgagtac ctgcccctgc tgcagggcaa gtctctgggc atgatcttcg agaagcggag 300
cacccggacc cggctgtcta ccgagacagg atttgccctg ctgggcggcc acccttgctt 360
tctgaccacc caggatatcc acctgggcgt gaacgagagc ctgaccgaca cagccagagt 420
gctgagcagc atggccgatg ccgtgctggc cagagtgtac aagcagagcg acctggacac 480
cctggccaaa gaggccagca tccccatcat caacggcctg tccgacctgt accaccccat 540
ccagatcctg gccgactacc tgaccctgca ggaacactac agctccctga agggcctgac 600
actgagctgg atcggcgacg gcaacaacat cctgcactct atcatgatga gcgccgccaa 660
gttcggcatg catctgcagg ccgccacccc caagggctat gagcctgatg ccagcgtgac 720
caagctggcc gagcagtacg ccaaagagaa cggcaccaag ctgctgctga ccaacgaccc 780
tctggaagcc gcccacggcg gcaatgtgct gatcaccgat acctggatca gcatgggcca 840
ggaagaggaa aagaagaagc ggctgcaggc cttccagggc taccaagtga ccatgaagac 900
cgccaaagtg gccgccagcg actggacctt cctgcactgc ctgcccagaa agcccgaaga 960
ggtggacgac gaggtgttct acagcccccg gtccctggtg tttcccgagg ccgagaaccg 1020
gaagtggacc atcatggctg tgatggtgtc tctgctgacc gactactccc cccagctgca 1080
gaagcccaag ttctga 1096

<210> SEQ ID NO 40
<211> LENGTH: 13
<212> TYPE: DNA
<213> ORGANISM: Artificial Sequence
<220> FEATURE:
<223> OTHER INFORMATION: The following polynucleotide (e.g., DNA) sequence (SEQ ID NO: 40) corresponds to a 5' UTR referred to as Minimal

<400> SEQUENCE: 40
gggagacgcc acc 13

<210> SEQ ID NO 41
<211> LENGTH: 43
<212> TYPE: DNA
<213> ORGANISM: Artificial Sequence
<220> FEATURE:
<223> OTHER INFORMATION: The following polynucleotide (e.g., DNA) sequence (SEQ ID NO: 41) corresponds to a 5' UTR referred to as hAg, a 5' UTR derived from human alpha globin

<400> SEQUENCE: 41
gggagactct tctggtcccc acagactcag agagaacgcc acc 43

<210> SEQ ID NO 42
<211> LENGTH: 13
<212> TYPE: DNA
<213> ORGANISM: Artificial Sequence
<220> FEATURE:
<223> OTHER INFORMATION: The following polynucleotide (e.g., DNA) sequence (SEQ ID NO: 42) corresponds to a 5' UTR referred to as TISU

<400> SEQUENCE: 42
gggagacgcc aag 13

<210> SEQ ID NO 43
<211> LENGTH: 14
<212> TYPE: DNA
<213> ORGANISM: Artificial Sequence
<220> FEATURE:
<223> OTHER INFORMATION: The following polynucleotide (e.g., DNA) sequence (SEQ ID NO: 43) corresponds to a 5' UTR referred to as TISU+T

<400> SEQUENCE: 43
gggagactgc caag 14

<210> SEQ ID NO 44
<211> LENGTH: 1125
<212> TYPE: DNA
<213> ORGANISM: Artificial Sequence
<220> FEATURE:
<223> OTHER INFORMATION: The following polynucleotide (e.g., DNA) sequence (SEQ ID NO: 44) shows the hOTC-STOP-RNA construct with the T7 promoter followed by a human alpha globin 5' UTR

<400> SEQUENCE: 44
taatacgact cactataggg agactcttct ggtccccaca gactcagaga gaaccgcccg 60
tgactgttca acctgcggat cctgctgaac aacgccgcct tccggaacgg ccacaacttc 120
tgagtgcgca acttcagtga cggccagccc ctgcagaaca aggtgcagct gaagggcagg 180

-continued

```
gacctgctga ccctgaagaa cttcaccggc gaagagatca agtactgact gtggctgagc    240

gccgacctga agttccggat caagcagaag ggcgagtacc tgcccctgct gcagggcaag    300

tctctgggct gaatcttcga gaagcggagc acccggaccc ggctgtctac cgagacagga    360

tttgccctgc tgggcggcca cccttgcttt ctgaccaccc aggatatcca cctgggcgtg    420

aacgagagcc tgaccgacac agccagagtg ctgagcagct gagccgtgac cgtgctggcc    480

agagtgtaca agcagagcga cctggacacc ctggccaaag aggccagcat ccccatcatc    540

aacggcctgt ccgacctgta ccaccccatc cagatcctgg ccgactacct gaccctgcag    600

gaacactaca gctccctgaa gggcctgaca ctgagctgga tcggcgacgg caacaacatc    660

ctgcactcta tctgatgaag cgccgccaag ttcggctgac atctgcaggc cgccaccccc    720

aagggcttga agcctgtgac cagcgtgacc aagctggccg agcagtacgc caaagagaac    780

ggcaccaagc tgctgctgac caacgaccct ctggaagccg cccacggcgg catgatgctg    840

atcaccgata cctggatcag ctgaggccag gaagaggaaa agaagaagcg gctgcaggcc    900

ttccagggct accaagtgac catgaagacc gccaaagtgg ccgccagcga ctggaccttc    960

ctgcactgcc tgcccagaaa gcccgaagag gtggacgacg aggtgttcta cagcccccgg   1020

tccctggtgt ttcccgaggc cgagaaccgg aagtggacca tctgagctgt gtgagtgtct   1080

ctgctgaccg actactcccc ccagctgcag aagcccaagt tctga                   1125
```

<210> SEQ ID NO 45
<211> LENGTH: 1095
<212> TYPE: DNA
<213> ORGANISM: Artificial Sequence
<220> FEATURE:
<223> OTHER INFORMATION: The following polynucleotide (e.g., DNA) sequence (SEQ ID NO: 45) corresponds to the codon optimized ORF from the murine OTC sequence (NM_008769.4) from NCBI Database flanked by a minimal 5' UTR (T7-mOTCORF(CO)

<400> SEQUENCE: 45

```
taatacgact cactataggg agacgccacc atgctgagca acctgagaat cctgctgaac     60

aacgccgccc tgagaaaggg ccacacaagc gtcgtgcggc acttttggtg cggcaagcct    120

gtgcagagcc aggtgcagct gaagggcagg gacctgctga ccctgaagaa cttcaccggc    180

gaagagatcc agtacatgct gtggctgagc gccgacctga agttcagaat caagcagaag    240

ggcgagtacc tgcccctgct gcagggcaag tctctgggca tgatcttcga gaagagaagc    300

accagaacca ggctgagcac cgagacaggc ttcgctctgc tgggcggcca ccctagcttt    360

ctgaccaccc aggatatcca cctgggcgtg aacgagagcc tgaccgacac agccagagtg    420

ctgagcagca tgaccgatgc cgtgctggcc agagtgtaca agcagtccga cctggacacc    480

ctggccaaag aggccagcat ccccatcgtg aacggcctga gcgacctgta ccaccccatc    540

cagatcctgg ccgactacct gaccctgcag gaacactacg gctccctgaa gggcctgaca    600

ctgagctgga tcggcgacgg caacaacatc ctgcactcta tcatgatgag cgccgccaag    660

ttcggcatgc atctgcaggc cgctaccccc aagggctacg agccagaccc caacatcgtg    720

aagctggccg agcagtacgc caaagagaac ggcaccaagc tgagcatgac caacgacccc    780

ctggaagccg ctagaggcgg caacgtgctg atcaccgaca cctggatcag catgggccag    840

gaagatgaga agaagaagag actgcaggcc ttccagggct accaagtgac catgaagacc    900

gccaaggtgg ccgctagcga ctggaccttc ctgcactgcc tgcccagaaa gcccgaagag    960

gtggacgacg aggtgttcta cagccctaga agcctggtgt tccccgaggc cgagaacaga   1020
```

```
aagtggacca tcatggctgt gatggtgtct ctgctgaccg actactcccc cgtgctgcag   1080

aagcccaagt tctga                                                     1095


<210> SEQ ID NO 46
<211> LENGTH: 1078
<212> TYPE: RNA
<213> ORGANISM: Artificial Sequence
<220> FEATURE:
<223> OTHER INFORMATION: The following polyribonucleotide (e.g., RNA)
      sequence (SEQ ID NO: 46) corresponds to the RNA sequence which
      results from transcription of the DNA sequence shown in SEQ ID NO:
      45 showing the codon optimized ORF from the murine OTC sequence
      (NM_008769.4) from NCBI Database flanked by a minimal 5' UTR
      (T7-mOTCORF(CO))

<400> SEQUENCE: 46

gggagacgcc accaugcuga gcaaccugag aauccugcug aacaacgccg cccugagaaa     60

gggccacaca agcgucgugc ggcacuuuug gugcggcaag ccugugcaga gccaggugca    120

gcugaagggc agggaccugc ugacccugaa gaacuucacc ggcgaagaga uccaguacau    180

gcuguggcug agcgccgacc ugaaguucag aaucaagcag aagggcgagu accugcccc    240

gcugcagggc aagucucugg gcaugaucuu cgagaagaga agcaccagaa ccaggcugag    300

caccgagaca ggcuucgcuc ugcugggcgg ccacccuagc uuucugacca cccaggauau    360

ccaccugggc gugaacgaga gccugaccga cacagccaga gugcugagca gcaugaccga    420

ugccgugcug gccagagugu acaagcaguc cgaccuggac acccuggcca aagaggccag    480

cauccccauc gugaacggcc ugagcgaccu guaccacccc auccagaucc uggccgacua    540

ccugacccug caggaacacu acggcucccu gaagggccug acacugagcu ggaucggcga    600

cggcaacaac auccugcacu cuaucaugau gagcgccgcc aaguucggca ugcaucugca    660

ggccgcuacc cccaagggcu acgagccaga ccccaacauc gugaagcugg ccgagcagua    720

cgccaaagag aacggcacca agcugagcau gaccaacgac ccccuggaag ccgcuagagg    780

cggcaacgug cugaucaccg acaccuggau cagcaugggc caggaagaug agaagaagaa    840

gagacugcag gccuuccagg gcuaccaagu gaccaugaag accgccaagg uggccgcuag    900

cgacuggacc uuccugcacu gccugcccag aaagcccgaa gagguggacg acgagguguu    960

cuacagcccu agaagccugg uguuccccga ggccgagaac agaaagugga ccaucauggc   1020

ugugauggug ucucugcuga ccgacuacuc ccccgugcug cagaagccca aguucuga     1078


<210> SEQ ID NO 47
<211> LENGTH: 49
<212> TYPE: DNA
<213> ORGANISM: Artificial Sequence
<220> FEATURE:
<223> OTHER INFORMATION: The following polynucleotide (e.g., DNA)
      sequence (SEQ ID NO: 47) corresponds to a 5' UTR referred to as
      CYBA

<400> SEQUENCE: 47

gggagaccgc gcctagcagt gtcccagccg ggttcgtgtc gccgccacc                 49


<210> SEQ ID NO 48
<211> LENGTH: 20
<212> TYPE: DNA
<213> ORGANISM: Artificial Sequence
<220> FEATURE:
<223> OTHER INFORMATION: huCSP1 (forward)

<400> SEQUENCE: 48
```

-continued caagttttgc agtggaatcg 20

<210> SEQ ID NO 49
<211> LENGTH: 20
<212> TYPE: DNA
<213> ORGANISM: Artificial Sequence
<220> FEATURE:
<223> OTHER INFORMATION: huCSP1 (reverse)

<400> SEQUENCE: 49
actgggtagc caatggtgtc 20

<210> SEQ ID NO 50
<211> LENGTH: 17
<212> TYPE: DNA
<213> ORGANISM: Artificial Sequence
<220> FEATURE:
<223> OTHER INFORMATION: huASL (forward)

<400> SEQUENCE: 50
acatggcctc ggagagt 17

<210> SEQ ID NO 51
<211> LENGTH: 20
<212> TYPE: DNA
<213> ORGANISM: Artificial Sequence
<220> FEATURE:
<223> OTHER INFORMATION: huASL (reverse)

<400> SEQUENCE: 51
atggacgcgt tgaacttctc 20

<210> SEQ ID NO 52
<211> LENGTH: 23
<212> TYPE: DNA
<213> ORGANISM: Artificial Sequence
<220> FEATURE:
<223> OTHER INFORMATION: huARG1 (forward)

<400> SEQUENCE: 52
cctcctgaag gaactaaaag gaa 23

<210> SEQ ID NO 53
<211> LENGTH: 22
<212> TYPE: DNA
<213> ORGANISM: Artificial Sequence
<220> FEATURE:
<223> OTHER INFORMATION: huARG1 (reverse)

<400> SEQUENCE: 53
ccttggcaga tatacaggga gt 22

<210> SEQ ID NO 54
<211> LENGTH: 22
<212> TYPE: DNA
<213> ORGANISM: Artificial Sequence
<220> FEATURE:
<223> OTHER INFORMATION: huASS1 (forward)

<400> SEQUENCE: 54
cctgtgctta taacctggga tg 22

<210> SEQ ID NO 55
<211> LENGTH: 20
<212> TYPE: DNA
<213> ORGANISM: Artificial Sequence
<220> FEATURE:
<223> OTHER INFORMATION: huASS1 (reverse)

<400> SEQUENCE: 55
gagcctttgc tggacatagc 20

<210> SEQ ID NO 56
<211> LENGTH: 20
<212> TYPE: DNA
<213> ORGANISM: Artificial Sequence
<220> FEATURE:
<223> OTHER INFORMATION: huOTC (forward)

<400> SEQUENCE: 56
ccagatcctg gctgattacc 20

<210> SEQ ID NO 57
<211> LENGTH: 20
<212> TYPE: DNA
<213> ORGANISM: Artificial Sequence
<220> FEATURE:
<223> OTHER INFORMATION: huOTC (reverse)

<400> SEQUENCE: 57
ccagctgagg gtaagacctt 20

<210> SEQ ID NO 58
<211> LENGTH: 20
<212> TYPE: DNA
<213> ORGANISM: Artificial Sequence
<220> FEATURE:
<223> OTHER INFORMATION: huOTCSNIM18#18 (forward)

<400> SEQUENCE: 58
ctcagagaga acgccaccat 20

<210> SEQ ID NO 59
<211> LENGTH: 19
<212> TYPE: DNA
<213> ORGANISM: Artificial Sequence
<220> FEATURE:
<223> OTHER INFORMATION: huOTCSNIM18#18 (reverse)

<400> SEQUENCE: 59
aagttgcgca ccatgaagt 19

<210> SEQ ID NO 60
<211> LENGTH: 19
<212> TYPE: DNA
<213> ORGANISM: Artificial Sequence
<220> FEATURE:
<223> OTHER INFORMATION: mOTCSNIM31#62 (forward)

<400> SEQUENCE: 60
tgagaaaggg ccacacaag 19

<210> SEQ ID NO 61
<211> LENGTH: 22
<212> TYPE: DNA
<213> ORGANISM: Artificial Sequence
<220> FEATURE:
<223> OTHER INFORMATION: mOTCSNIM31#62 (reverse)

<400> SEQUENCE: 61
cagcatgtac tggatctctt cg 22